US009908931B2

(12) United States Patent
Xu et al.

(10) Patent No.: US 9,908,931 B2
(45) Date of Patent: Mar. 6, 2018

(54) ANTI-HEMAGGLUTININ ANTIBODIES AND METHODS OF USE

(71) Applicant: Genentech, Inc., South San Francisco, CA (US)

(72) Inventors: Min Xu, Millbrae, CA (US); Mercedesz Balazs, Burlingame, CA (US); Ning Chai, Dublin, CA (US); Nancy Chiang, San Francisco, CA (US); Henry Chiu, San Francisco, CA (US); Zhaoyu Jin, Foster City, CA (US); Zhonghua Lin, San Francisco, CA (US); Patrick Lupardus, San Francisco, CA (US); Gerald r. Nakamura, San Francisco, CA (US); Hyunjoo Park, Alemada, CA (US); Lee Swem, Montara, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/042,436

(22) Filed: Feb. 12, 2016

(65) Prior Publication Data
US 2016/0168230 A1   Jun. 16, 2016

Related U.S. Application Data

(62) Division of application No. 14/077,414, filed on Nov. 12, 2013, now Pat. No. 9,284,365.

(60) Provisional application No. 61/725,859, filed on Nov. 13, 2012.

(51) Int. Cl.
| | |
|---|---|
| A61K 39/145 | (2006.01) |
| C07K 16/10 | (2006.01) |
| A61K 39/42 | (2006.01) |
| A61K 31/215 | (2006.01) |
| A61K 31/235 | (2006.01) |
| A61K 31/24 | (2006.01) |
| A61K 39/00 | (2006.01) |

(52) U.S. Cl.
CPC ........ *C07K 16/1018* (2013.01); *A61K 31/215* (2013.01); *A61K 31/235* (2013.01); *A61K 31/24* (2013.01); *A61K 39/42* (2013.01); *A61K 2039/505* (2013.01); *A61K 2039/507* (2013.01); *A61K 2039/545* (2013.01); *C07K 2317/21* (2013.01); *C07K 2317/33* (2013.01); *C07K 2317/56* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,589,174 A | 12/1996 | Okuno et al. | |
| 5,631,350 A | 5/1997 | Okuno et al. | |
| 2011/0274702 A1 | 11/2011 | Lanzavecchia | |

FOREIGN PATENT DOCUMENTS

| | | |
|---|---|---|
| WO | 02/46235 A1 | 6/2002 |
| WO | 2008/028946 A2 | 3/2008 |
| WO | 2008/028946 A3 | 3/2008 |
| WO | 2008/110937 A2 | 9/2008 |
| WO | 2008/110937 A3 | 9/2008 |
| WO | 2009/053604 A2 | 4/2009 |
| WO | 2009/053604 A3 | 4/2009 |
| WO | 2009/053604 A9 | 4/2009 |
| WO | 2009/115972 A1 | 9/2009 |
| WO | 2010/010466 A2 | 1/2010 |
| WO | 2010/010466 A3 | 1/2010 |
| WO | 2010/073647 A1 | 7/2010 |
| WO | 2010/130636 A1 | 11/2010 |
| WO | 2011/111966 A2 | 9/2011 |
| WO | 2011/111966 A3 | 9/2011 |
| WO | 2011/117848 A1 | 9/2011 |
| WO | 2011/160083 A1 | 12/2011 |
| WO | 2012/021786 A2 | 2/2012 |
| WO | 2012/021786 A3 | 2/2012 |
| WO | 2012/0058124 A1 | 8/2012 |
| WO | 2013/011347 A1 | 1/2013 |

OTHER PUBLICATIONS

Ekiert et al., "Antibody Recognition of a Highly Conserved Influenza Virus Epitope" Science 324:246-251 ( 2009).
Corti et al., "A Neutralizing Antibody Selected from Plasma Cells That Binds to Group 1 and Group 2 Influenza A Hemagglutinins" Science 333:850-856 (Aug. 2011).
PCT International Search Report and Written Opinion for PCT/US2013/069567.
Clementi et al., "A Human Monoclonal Antibody with Neutralizing Activity against Highly Divergent Influenza Subtypes" PLoS ONE 6(12) ( 2011).
Cui et al., "The Molecular Mechanism of Action of the CR6261-Azichromycin Combination Found through Computational Analysis" PLoS ONE 7(5) ( 2012).
Hu, "Fully human broadly neutralizing monoclonal antibodies against influenza A viruses generated from the memory B cells of a 2009 pandemic H1N1 influenza vaccine recipient" Virology 435:320-328 ( 2013).
Nakamura et al., "An in Vivo Human-Plasmablast Enrichment Technique Allows Rapid Identification of Therapeutic Influenza A Antibodies" Cell Host & Microbe 14:93-103 (Jul. 2013).
Dreyfus et al., "Highly Conserved Protective Epitopes on Influenza B Viruses" Science 337:1343-1348 ( 2012).
Ekiert et al., "A Highly Conserved Neutralizing Epitope on Group 2 Influenza A Viruses" Science 333:843-850 ( 2011).
Sui et al., "Structural and functional bases for broad-spectrum neutralization of avian and human influenza A viruses" Nature Structural & Molecular Biology 16(3):265-273 ( 2009).
2012/029997 A1 counterpart publication US2012/0058124A, Aug. 3, 2012, WO.

*Primary Examiner* — Agnieszka Boesen
(74) *Attorney, Agent, or Firm* — Anna M. Tan

(57) ABSTRACT

The present invention provides anti-hemagglutinin antibodies, compositions comprising anti-hemagglutinin antibodies, and methods of using the same.

19 Claims, 57 Drawing Sheets

| Influenza Strain | HA Subtype | 37.18 IC50 (nM) | 37.18 95% CI (nM) | 39.29 IC50 (nM) | 39.29 95% CI (nM) | 81.39 IC50 (nM) | 81.39 95% CI (nM) | 36.89 IC50 (nM) | 36.89 95% CI (nM) | mAb 9 IC50 (nM) | mAb 9 95% CI (nM) | mAb 23 IC50 (nM) | mAb 23 95% CI (nM) |
|---|---|---|---|---|---|---|---|---|---|---|---|---|---|
| A/CA/7/2009 | H1 | 1.1 | 0.75 - 1.6 | 2.5 | 2.0 - 3.1 | 2.1 | 1.1 - 3.8 | NA | NA | NA | NA | NA | NA |
| A/Brisbane/59/2007 | H1 | 2.3 | 1.8 - 3.0 | 1.9 | 1.2 - 2.9 | 0.65 | 0.46 - 0.94 | NA | NA | NA | NA | NA | NA |
| A/Solomon/3/2006 | H1 | 8.0 | 3.9 - 16.6 | 25.1 | 20.1 - 31.4 | 14.6a | 12.3 - 17.4 | NA | NA | NA | NA | NA | NA |
| A/New Caldonia/20/1999 | H1 | 3.1 | 1.3 - 7.4 | 9.2 | 5.7 - 15.0 | 6.1 | 4.7 - 7.9 | NA | NA | NA | NA | NA | NA |
| A/PR/8/1934 | H1 | 1.2 | 0.81 - 1.9 | 2.0 | 1.3 - 3.3 | 1.9 | 1.2 - 3.2 | NA | NA | NA | NA | NA | NA |
| A/Japan/305/1957 | H2 | 2.4 | 1.4 - 4.1 | 6.0 | 4.4 - 8.1 | 3.7 | 2.4 - 5.6 | NA | NA | NA | NA | NA | NA |
| A/Victoria/361/2011 | H3 | NA | NA | 3.4 | 2.4 - 4.8 | 3.6 | 2.4 - 5.3 | 9.7 | 8.0 - 11.9 | 41.0 | 26.3 - 64.1 | 12.0 | 7.2 - 20.2 |
| A/Perth/16/2009 | H3 | NA | NA | 3.0 | 2.4 - 3.8 | 1.6 | 1.2 - 2.0 | 1.1 | 0.86 - 1.5 | 13.5 | 10.4 - 17.5 | 4.2 | 3.3 - 5.4 |
| A/Brisbane/10/2007 | H3 | NA | NA | 2.3 | 2.0 - 2.7 | 1.9 | 1.7 - 2.2 | 1.9 | 1.5 - 2.4 | 26.1 | 18.2 - 37.4 | 6.3 | 4.6 - 8.0 |
| A/Wisconsin/67/2005 | H3 | NA | NA | 1.3 | 0.88 - 1.8 | 0.81 | 0.64 - 1.0 | 1.6 | 0.81 - 3.3 | 7.3 | 4.5 - 11.9 | 0.85 | 0.58 - 1.3 |
| A/Victoria/3/1975 | H3 | NA | NA | 2.5 | 1.9 - 3.4 | 2.8 | 2.2 - 3.7 | 2.2 | 0.94 - 5.0 | 17.2 | 9.3 - 31.9 | 3.7 | 2.3 - 6.0 |
| A/Port Chalmers/1/1973 | H3 | NA | NA | 2.2 | 1.6 - 3.1 | 1.5 | 1.1 - 1.9 | 1.9 | 0.75 - 4.6 | 18.4 | 12.5 - 26.9 | 2.4 | 1.5 - 3.8 |
| A/HK/8/1968 | H3 | NA | NA | 45.1 | 25.7 - 79.2 | 26.3 | 14.5 - 47.8 | 34.7 | 19.8 - 60.7 | 843 | 295 - 2406 | 336 | 240 - 470 |
| A/Aichi/2/1968 | H3 | NA | NA | 35.0 | 21.1 - 58.0 | 7.3 | 3.7 - 14.1 | 13.9 | 8.2 - 23.4 | 1172 | 589 - 2330 | 271 | 176 - 419 |

FIG. 3

```
                                         *                   *
H1N1  -------MKAILVVLLYTFATAN---ADTLCIGYHANNSTDTVDTVLEKNVTVTHSVNLLE 51
H2N2  ---------MAIIYLILLFTAVR---GDQICIGYHANNSTEMVDTILERNVTVTHAKDILE 49
H3N2  MKTIIALSYILCLVFAQKLPGNDNSTATLCLGHHAVPNGTIVKTITNDQIEVTNATELVQ 60
H5N1  --------MEKIVLLFAIVSLVK---SDQICIGYHANNSTEQVDTIMEKNVTVTHAQDILE 50
H7N4  MN------TRILILTLTAVIHTN---ADKICLGHHAVSNGTKVNTLTERGVEVVNATETVE 52

H1N1  DKHNGKLCKLRGVAPLHLGKCNIAGWILGNPECESLSTASSWSYIVETPSSDNGTCYPGD 111
H2N2  KTHNGKLCKLNGIPPLELGDCSIAGWLLGNPECDRLLSVPEWSYIMEKENPRDGLCYPGS 109
H3N2  SSSTGEICDS-PHQILDGKNCTLIDALLGDPQCDGFQNK-KWDLFVERSKA-YSNCYPYD 117
H5N1  KKHNGKLCDLDGVKPLILRDCSVAGWLLGNPMCDEFINVPEWSYIVEKANPVNDLCYPGD 110
H7N4  QMNIPRICTK-GKKAIDLGQCGLLGIVTGPPQCDQFLEF-TADLIIERREG-NDVCYPGK 109

H1N1  FIDYEELREQLSSVSSFERFEIFPKTSSWPNHDSNKGVTAACPHAGAKSFYKNLIWLVK- 170
H2N2  FNDYEELKHLLSSVKHFEKVKILPK-DRWTQHTTTGG-SRACAVSGNPSFFRNMVWLTK- 166
H3N2  VPDYASLRSLVASSGTLEFNNESFNWTGVTQN----GTSSACIRRSKNSFFSRLNWLTH- 172
H5N1  FNDYEELKHLLSRINHFEKIQIIPK-SSWSSHEASLGVSSACPYQGKSSFFRNVVWLIK- 168
H7N4  FVNEEALRQILRGSGGINKETTGFTYSGIRTN----GVTSACRR-SESSFYAEMKWLLSN 164

H1N1  -KGNSYPKLSKSYINDKGKEVLVLWGIHHPSTSADQQSLYQNADAYVFVGSSRYSKKFKP 229
H2N2  -KGSDYPVAKGSYNNTSGEQMLIIWGVHHPNDETEQRTLYQNVGTYVSVGTSTLNKRSTP 225
H3N2  -LNFKYPALNVTMPNNEQFDKLYIWGVHHPGTDKDQIFLYAQASGRITVSTKRSQQTVSP 231
H5N1  -KNSTYPTIKRSYNNTNQEDLLVLWGIHHPNDAAEQTKLYQNPTTYISVGTSTLNQRLVP 227
H7N4  TDNAAFPQMTKSYKNTRNEPALIVWGIHHSGSTTEQTKLYGSGSKLITVGSSNYQQSFVP 224

H1N1  EIAIRPKVRXXEGRMNYYWTLVEPGDKITFEATGNLVVPRYAFAMERNAGSGIIISDTPV 289
H2N2  EIATRLKVNGQGGRMEFSWTLLDMWDTINFESTGNLIAPEYGFKISKRGSSGIMKTEGTL 285
H3N2  NIGSRPRVRNIPSRISIYWTIVKPGDILLINSTGNLIAPRGYFKIRS-GKSSIMRSDAPI 290
H5N1  RIATRSKVNGQSGRMEFFWTILKPNDAINFESNGNFIAPEYAYKIVKKGDSTIMKSELEY 287
H7N4  SPGARPQVNGQSGRIDFHWLILNPNDTVTFSFNGAFVAP-DRVSFFK-GESTGIQSEVPV 282

*                                       *
H1N1  H-DCNTTCQTPKGAINTSLPFQNIHPITIGKCPKYVKSTKLRLATGLRNIPSIQ----SR 344
H2N2  E-NCETKCQTPLGAINTTLPFHNVHPLTIGECPKYVKSEKLVLATGLRNVPQIE----SR 340
H3N2  G-KCNSECITPNGSIPNDKPFQNVNRITYGACPRYVKQNTLKLATGMRNVPE----KQTR 345
H5N1  G-NCNTKCQTPMGAINSSMPFHNIHPLTIGECPKYVKSNRLVLATGLRNSPQRERRRKKR 346
H7N4  DANCEGECYHSGGTITSNLPFQNVNSRAVGKCPKYVKQKSLLLATGMKNVPEIPR-KRKR 341

****               *  **  *  **   *   ***
H1N1  GLFGAIAGFIEGGWTGMVDGWYGYHHQNEQGSGYAADLKSTQNAIDEITNKVNSVIEKMN 404
H2N2  GLFGAIAGFIEGGWQGMVDGWYGYHHSNDQGSGYAADKESTQKAFDGITNKVNSVIEKMN 400
H3N2  GIFGAIAGFIENGWEGMVDGWYGFRHQNSEGRGQAADLKSTQAAIDQINGKLNRLIGKTN 405
H5N1  GLFGAIAGFIEGGWQGMVDGWYGYHHSNEQGSGYAADKESTQKAIDGVTNKVNSIIDKMN 406
H7N4  GLFGAIAGFIENGWEGLVDGWYGFRHQNSQGEGTAADYKSTQSAIDQITGKLNRLIEKTN 401

H1N1  TQFTAVGKEFNHLEKRIENLNKKVDDGFLDIWTYNAELLVLLENERTLDYHDSNVKNLYE 464
H2N2  TQFEAVGKEFSNLERRLENLNKKMEDGFLDVWTYNAELLVLMENERTLDFHDSNVKNLYD 460
H3N2  EKFHQIEKEFSEVEGRIQDLEKYVEDTKIDLWSYNAELLVALENQHTIDLTDSEMNKLFE 465
H5N1  TQFEAVGREFNNLERRIENLNKKMEDGFLDVWTYNAELLVLMENERTLDFHDSNVKNLYD 466
H7N4  QQFELIDNEFNEVEKQIGNVINWTRDSITEVWSYNAELLVAMENQHTIDLADSEMNKLYE 461

H1N1  KVRSQLKNNAKEIGNGCFEFYHKCDNTCMESVKNGTYDYPKYSEEAKLNREEIDGVKLES 524
H2N2  KVRMQLRDNVKELGNGCFEFYHKCDDECMNSVKTGTYDYPKYEEESKLNRNEIKGVKLSS 520
H3N2  KTKKQLRENAEDMGNGCFKIYHKCDNACIGSIRNGTYDHDVYRDEALNNRFQIKGVELKS 525
H5N1  KVRLQLRDNAKELGNGCFEFYHKCDNECMESVRNGTYDYPQYSEEARLKREEISGVKLES 526
H7N4  RVRRQLRENAEEDGTGCFEIFHKCDDDCMASIRNNTYDHSTYREEAMQNRLKIDPVKLSS 521

H1N1  TRIYQILAIYSTVASSLVLVVSLGAISFWMCSNGSLQCRICI 566 (SEQ ID NO: 224)
H2N2  MGVYQILAIYATVAGSLSLAIMMAGISFWMCSNGSLQCRICI 562 (SEQ ID NO: 225)
H3N2  -GYKDWILWISFAISCFLLCVALLGFIMWACQKGNIRCNICI 566 (SEQ ID NO: 226)
H5N1  IGIYQILSIYSTVASSLALAIMVAGLSLWMCSNGSLQCRICI 568 (SEQ ID NO: 227)
H7N4  -GYKDVILWFSFGASCFLLLAIAMGLGFICVKNGNMRCTICI 562 (SEQ ID NO: 228)
```

Light Chain, Kappa

|  | 1 2 3 4 5 6 7 8 9 10 11 12 13 14 15 16 17 18 19 20 21 22 23 24 25 26 27 A B C D E F 28 29 30 31 32 33 34 35 36 |
|---|---|
| IGKV3-15*01 | E I V M T Q S P A T L S V S P G E R A T L S C R A S Q . . . . . . S V S S N L A W Y |
| 81.39 B1C1 | E I V [L] Q S P A T L S V S P G E R A T L S C R A S Q . . . . . . S V [D] S N L A W Y |

Kabat - CDR L1
Chothia - CDR L1
Contact - CDR L1

|  | 37 38 39 40 41 42 43 44 45 46 47 48 49 50 51 52 53 54 A B C D E 55 56 57 58 59 60 61 62 63 64 65 66 67 68 69 70 71 |
|---|---|
| IGKV3-15*01 | Q Q K P G Q A P R L L I Y G A S T R . . . . . A T G I P A R F S G S G S G T E F |
| 81.39 B1C1 | Q Q K P G Q A P R L L I [V] [S] A S T R . . . . . A T G I P A R F S G S G S G T E F |

Kabat - CDR L2
Chothia - CDR L2
Contact - CDR L2

|  | 72 73 74 75 76 77 78 79 80 81 82 83 84 85 86 87 88 89 90 91 92 93 94 95 A B C D E F 96 97 98 99 100 101 102 103 104 105 106 107 |
|---|---|
| IGKV3-15*01 | T L T I S S L Q S E D F A V Y Y C Q Q Y N N W P . . . . . . L T F G G G T K V E I K |
| 81.39 B1C1 | T L [A] I S S L Q S E D F A V Y Y C Q [H] Y [T] [N P R] . . . . . . L T F G G G T K V E I K |

Kabat - CDR L3
Chothia - CDR L3
Contact - CDR L3

IGKJ4

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 81.39 B1C1 | Q | V | Q | L | V | E | S | G | G | G | V | V | Q | P | G | R | S | L | R | L | S | C | A | A | S | G | F | A | F | H | N | R | A | M | H | . | . | W | V | R | Q | A | P | G | K |

Kabat - CDR H1 / Chothia - CDR H1 / Contact - CDR H1

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 B1C1 | G | L | E | W | V | A | L | I | V | F | . | . | D | G | S | K | Q | Y | Y | A | D | S | V | K | G | R | F | T | I | S | R | D | N | S | K | N | T | V | F | L | Q | M | N | S | L |

Kabat - CDR H2 / Chothia - CDR H2 / Contact - CDR H2

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 |  |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | Q | H | W | G | Q | G | T | L | V | T | V | S | S | IGHJ1*01 |
| 81.39 B1C1 | R | P | E | D | T | A | V | Y | Y | C | A | V | P | G | P | I | F | G | I | F | P | P | W | S | V | F | . | . | . | D | H | W | G | Q | G | T | L | V | T | V | S | S |  |

Kabat - CDR H3 / Chothia - CDR H3 / Contact - CDR H3

Light Chain, Kappa

```
                1  2  3  4  5  6  7  8  9 10 11 12 13 14 15 16 17 18 19 20 21 22 23   24 25 26 27 A  B  C  D  E  F 28 29 30 31 32 33 34 35 36
IGKV3-15*01     E  I  V  M  T  Q  S  P  A  T  L  S  V  S  P  G  E  R  A  T  L  S  C    R  A  S  Q  .  .  .  .  .  .  S  V  S  S  N  L  A  W  Y
81.39 SVSH-NYP  E  I  V  L  T  Q  S  P  A  T  L  S  V  S  P  G  E  R  A  T  L  S  C    R  A  S  Q  .  .  .  .  .  .  S  V  S  H  N  L  A  W  Y 37 38 39 40 41 42 43 44 45 46 47 48 49 50 51 52 53 54 A  B  C  D  E 55 56 57
IGKV3-15*01     Q  Q  K  P  G  Q  A  P  R  L  L  I  Y  G  A  S  T  R  .  .  .  .  . A  T  G
81.39 SVSH-NYP  Q  Q  K  P  G  Q  A  P  R  L  L  V  Y  S  A  S  T  R  .  .  .  .  . A  T  G 72 73 74 75 76 77 78 79 80 81 82 83 84 85 86 87 88 89 90 91 92 93 94 95 A  B  C  D  E  F 96 97 98 99 100 101 102 103 104 105 106 107
IGKV3-15*01     T  L  T  I  S  S  L  Q  S  E  D  F  A  V  Y  Y  C  Q  Q  Y  N  N  W  P  .  .  .  .  .  .  .  T  F  G  G  G   T   K   V   E   I   K
81.39 SVSH-NYP  T  L  T  I  A  S  L  Q  S  E  D  F  A  V  Y  Y  C  Q  H  Y  N  V  W  P  P  R  .  .  .  .  .  T  F  G  G  G   G   S   K   V   E   I   K   IGKJ4
```

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35A | 35B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 81.39 SVSH-NYP | V | Q | L | V | E | S | G | G | G | V | V | Q | P | G | R | S | L | R | L | S | C | A | A | S | G | F | A | F | H | N | R | A | M | H | . | . | W | V | R | Q | A | P | G | K | |

Kabat - CDR H1: 31–35B
Chothia - CDR H1: 26–32
Contact - CDR H1: 30–35B

| Kabat number | 44 | 45 | 46 | 47 | 48 | 49 | 50 | 51 | 52 | 52A | 52B | 52C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 82A | 82B | 82C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 SVSH-NYP | G | L | E | W | V | A | L | I | V | F | . | . | D | G | S | I | K | Q | Y | Y | A | D | S | V | K | G | R | F | T | I | S | R | D | N | S | K | N | T | V | F | L | Q | M | N | S | L |

Kabat - CDR H2: 50–65
Chothia - CDR H2: 52–56
Contact - CDR H2: 47–58

| Kabat number | 83 | 84 | 85 | 86 | 87 | 88 | 89 | 90 | 91 | 92 | 93 | 94 | 95 | 96 | 97 | 98 | 99 | 100 | 100A | 100B | 100C | 100D | 100E | 100F | 100G | 100H | 100I | 100J | 100K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | F | Q | H | W | G | Q | G | T | L | V | T | V | S | S | IGHJ1*01 | | | |
| 81.39 SVSH-NYP | R | F | E | D | T | A | V | Y | Y | C | A | V | P | I | F | G | I | P | P | W | S | V | . | . | . | F | D | H | W | G | Q | G | T | L | V | T | V | S | S | | | | |

Kabat - CDR H3: 95–102
Chothia - CDR H3: 95–102
Contact - CDR H3: 93–101

*FIG. 23B*

Light Chain, Kappa

|  | 1 2 3 4 5 6 7 8 9 10 11 12 13 14 15 16 17 18 19 20 21 22 23 | 24 25 26 27 A B C D E F 28 29 30 31 32 33 34 35 36 |
|---|---|---|
| IGKV3-15*01 | E I V M T Q S P A T L S V S P G E R A T L S C | R A S Q . . . . . S V S S N L A W Y |
| 81.39 B1F1 | E I V M T Q S P A T L S V S P G E R A T L S C | R A S Q . . . . . S V [D] S N L A W Y |

|  | 37 38 39 40 41 42 43 44 45 46 47 48 49 | 50 51 52 53 54 A B C D E 55 56 57 58 59 60 61 62 63 64 65 66 67 68 69 70 71 |
|---|---|---|
| IGKV3-15*01 | Q Q K P G Q A P R L L I Y | G A S T R . . . . . A T G I P A R F S G S G S G T E F |
| 81.39 B1F1 | Q Q K P G Q A P R L L I Y | [S] A S T R . . . . . A T G I P A R F S G S G S G T E F |

|  | 72 73 74 75 76 77 78 79 80 81 82 83 84 85 86 87 88 | 89 90 91 92 93 94 95 A B C D E F 96 | 97 98 99 100 101 102 103 104 105 106 107 |
|---|---|---|---|
| IGKV3-15*01 | T L T I S S L Q S E D F A V Y Y C | Q Q Y N N W P . . . . . . L T | F G G G T K V E I K |
| 81.39 B1F1 | T L [A] I S S L Q S E D F A V Y Y C | Q [H] Y [D] N W P [P R] . . . . L T | F G G G [S] K V E I K |

FIG. 24A

Heavy Chain

```
Kabat number   1  2  3  4  5  6  7  8  9 10 11 12 13 14 15 16 17 18 19 20 21 22 23 24 25 26 27 28 29 30 31 32 33 34 35 A  B  36 37 38 39 40 41 42 43
IGHV3-30*01    Q  V  Q  L  V  E  S  G  G  G  V  V  Q  P  G  R  S  L  R  L  S  C  A  A  S  G  F  T  F  S  S  Y  A  M  H  .  .  W  V  R  Q  A  P  G  K
81.39 B1F1     Q  V  Q  L  V  E  S  G  G  G  V  V  Q  P  G  R  S  L  R  L  S  C  A  A  S  G  F  A  F  H  N  R  A  M  H  .  .  W  V  R  Q  A  P  G  K
```
                                                                              Chothia - CDR H1
                                                                                 Kabat - CDR H1
                                                                              Contact - CDR H1

```
Kabat number  44 45 46 47 48 49 50 51 52 A  53 54 55 56 57 58 59 60 61 62 63 64 65 66 67 68 69 70 71 72 73 74 75 76 77 78 79 80 81 82 A  B  C
IGHV3-30*01    G  L  E  W  V  A  V  I  S  Y  .  .  D  G  S  N  K  Y  Y  A  D  S  V  K  G  R  F  T  I  S  R  D  N  S  K  N  T  L  Y  L  Q  M  N  S  L
81.39 B1F1     G  L  E  W  V  A  L  I  A  F  .  .  D  G  S  K  Q  Y  Y  A  D  S  V  K  G  R  F  T  I  S  R  D  N  S  K  N  T  V  F  L  Q  M  N  S  L
```
                                    Contact - CDR H2
                                       Chothia - CDR H2
                                          Kabat - CDR H2

```
Kabat number  83 84 85 86 87 88 89 90 91 92 93 94 95 96 97 98 99 100 A  B  C  D  E  F  G  H  I  J  K  101 102 103 104 105 106 107 108 109 110 111 112 113
IGHV3-30*01    R  A  E  D  T  A  V  Y  Y  C  A  R                                                                                                    IGHJ1*01
81.39 B1F1     R  P  E  D  T  A  V  Y  Y  C  A  V  P  G  P  I  F  G  I  F  P  P  W  S  V  .  .  F  Q  H  W  G  Q  G  T  L  V  T  V  S  S
                                                                                                    W  G  Q  G  T  L  V  T  V  S  S
```
                                          Kabat - CDR H3
                                             Chothia - CDR H3
                                                Contact - CDR H3

FIG. 24B

Light Chain, Kappa

```
              1  2  3  4  5  6  7  8  9  10 11 12 13 14 15 16 17 18 19 20 21 22 23 24 25 26 27  A  B  C  D  E  F 28 29 30 31 32 33 34 35 36
IGKV3-15*01   E  I  V  M  T  Q  S  P  A  T  L  S  V  S  P  G  E  R  A  T  L  S  C  R  A  S  Q  .  .  .  .  .  .  S  V  S  S  N  L  A  W  Y
81.39 SVDS    E  I  V  M  T  Q  S  P  A  T  L  S  V  S  P  G  E  R  A  T  L  S  C  R  A  S  Q  .  .  .  .  .  .  S  V  [D] S  N  L  A  W  Y 37 38 39 40 41 42 43 44 45 46 47 48 49 50 51 52 53 54  A  B  C  D  E 55 56 57 58 59 60 61 62 63 64 65 66 67 68 69 70 71
IGKV3-15*01   Q  Q  K  P  G  Q  A  P  R  L  L  I  Y  G  A  S  T  R   .  .  .  .  . A  T  G  I  P  A  R  F  S  G  S  G  S  G  T  E  F
81.39 SVDS    Q  Q  K  P  G  Q  A  P  R  L  L  I  Y  [V] A  S  T  R  .  .  .  .  . A  T  G  I  P  A  R  F  S  G  S  G  S  G  T  E  F 72 73 74 75 76 77 78 79 80 81 82 83 84 85 86 87 88 89 90 91 92 93 94 95  A  B  C  D  E  F 96 97 98 99 100 101 102 103 104 105 106 107
IGKV3-15*01   T  L  T  I  S  S  L  Q  S  E  D  F  A  V  Y  Y  C  Q  Q  Y  N  N  W  P   .  .  .  .  .  . L  T  F  G  G  G   T   K   V   E   I   K   IGKJ4
81.39 SVDS    T  L  T  I  [A] S  L  Q  S  E  D  F  A  V  Y  Y  C  Q  [H] [V] [N] N  W  [P] .  .  .  .  .  . L  T  F  G  G  G  [S]  K   V   E   I   K
```

Kabat - CDR L1
Chothia - CDR L1
Contact - CDR L1

Kabat - CDR L2
Chothia - CDR L2
Contact - CDR L2

Kabat - CDR L3
Chothia - CDR L3
Contact - CDR L3

*FIG. 25A*

Heavy Chain

| | Kabat number | | Sequence |
|---|---|---|---|
| | 1–43 | IGHV3-30*01 | Q V Q L V E S G G G V V Q P G R S L R L S C A A S G F T F S S Y A M H . . W V R Q A P G K |
| | | 81.39 SVDS | E V Q L V E S G G G V V Q P G R S L R L S C A A S G F A F H N R A M H . . W V R Q A P G K |

Kabat - CDR H1 (31–35B)
Chothia - CDR H1 (26–32)
Contact - CDR H1 (30–35B)

| | Kabat number | | Sequence |
|---|---|---|---|
| | 44–82C | IGHV3-30*01 | G L E W V A V I S Y . D G S N K Y Y A D S V K G R F T I S R D N S K N T L Y L Q M N S L |
| | | 81.39 SVDS | G L E W V A L I F . D G S K Q Y Y A D S V K G R F T I S R D N S K N T V F L Q M N S L |

Kabat - CDR H2 (50–65)
Chothia - CDR H2 (52–56)
Contact - CDR H2 (47–58)

| | Kabat number | | Sequence |
|---|---|---|---|
| | 83–113 | IGHV3-30*01 | R A E D T A V Y Y C A R . . . . . . . . . . . . . F Q H W G Q G T L V T V S S IGHJ1*01 |
| | | 81.39 SVDS | R P E D T A V Y Y C A V P G P I F G I F P P W S Y . F D H W G Q G T L V T V S S |

Kabat - CDR H3 (95–102)
Chothia - CDR H3 (95–102)
Contact - CDR H3 (93–101)

*FIG. 25B*

Light Chain, Kappa

```
                                                          Kabat - CDR L1
                                                          Chothia - CDR L1
                                                                    Contact - CDR L1
              1  2  3  4  5  6  7  8  9 10 11 12 13 14 15 16 17 18 19 20 21 22 23 24 25 26 27  A  B  C  D  E  F 28 29 30 31 32 33 34 35 36
IGKV3-15*01   E  I  V  M  T  Q  S  P  A  T  L  S  V  S  P  G  E  R  A  T  L  S  C  R  A  S  Q  .  .  .  .  .  .  S  V  S  S  N  L  A  W  Y
81.39 SVSS    E  I  V  L  T  Q  S  P  A  T  L  S  V  S  P  G  E  R  A  T  L  S  C  R  A  S  Q  .  .  .  .  .  .  S  V  S  S  N  L  A  W  Y Kabat - CDR L2
                                                          Chothia - CDR L2
                                                                    Contact - CDR L2
             37 38 39 40 41 42 43 44 45 46 47 48 49 50 51 52 53 54  A  B  C  D  E 55 56 57 58 59 60 61 62 63 64 65 66 67 68 69 70 71
IGKV3-15*01   Q  Q  K  P  G  Q  A  P  R  L  L  I  Y  G  A  S  T  R  .  .  .  .  .  A  T  G  I  P  A  R  F  S  G  S  G  S  G  T  E  F
81.39 SVSS    Q  Q  K  P  G  Q  A  P  R  L  L  I  Y  S  A  S  T  R  .  .  .  .  .  A  T  G  I  P  A  R  F  S  G  S  G  S  G  T  E  F Kabat - CDR L3
                                                          Chothia - CDR L3
                                                                    Contact - CDR L3
             72 73 74 75 76 77 78 79 80 81 82 83 84 85 86 87 88 89 90 91 92 93 94 95  A  B  C  D  E  F 96 97 98 99 100 101 102 103 104 105 106 107  IGKJ4
IGKV3-15*01   T  L  T  I  S  S  L  Q  S  E  D  F  A  V  Y  Y  C  Q  Q  Y  N  N  W  P  .  .  .  .  .  .  L  T  F  G  G   G   T   K   V   E   I   K
81.39 SVSS    T  L  T  I  A  S  L  Q  S  E  D  F  A  V  Y  Y  C  Q  H  Y  T  N  W  P  P  R  .  .  .  .  L  T  F  G  G   G   S   K   V   E   I   K
```

*FIG. 26A*

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 81.39 SVSS | E | V | Q | L | V | E | S | G | G | G | V | V | Q | P | G | R | S | L | R | L | S | C | A | A | S | G | F | T | F | A | E | N | R | A | M | H | . | . | W | V | R | Q | A | P | G | K |

Kabat - CDR H1
Chothia - CDR H1
Contact - CDR H1

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 SVSS | G | L | E | W | V | A | L | I | V | F | . | . | D | G | S | K | Q | Y | Y | A | D | S | V | K | G | R | F | T | I | S | R | D | N | S | K | N | T | V | F | L | Q | M | N | S | L |

Kabat - CDR H2
Chothia - CDR H2
Contact - CDR H2

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | Q | H | W | G | Q | G | T | L | V | T | V | S | S | IGHJ1*01 |
| 81.39 SVSS | R | P | E | D | T | A | V | Y | Y | C | A | R | V | P | G | P | I | F | G | I | F | P | P | M | S | V | . | . | F | D | H | W | G | Q | G | T | H | V | T | V | S | S | |

Kabat - CDR H3
Chothia - CDR H3
Contact - CDR H3

*FIG. 26B*

Light Chain, Kappa

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 81.39 SVDH | E | I | V | L | T | Q | S | P | A | T | L | S | V | S | P | G | E | R | A | T | L | S | C | R | A | S | Q | . | . | . | . | . | . | S | V | D | H | N | L | A | W | Y |

Kabat - CDR L1 / Chothia - CDR L1 / Contact - CDR L1

|  | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G | I | P | A | R | F | S | G | S | G | S | G | T | E | F |
| 81.39 SVDH | Q | Q | K | P | G | Q | A | P | R | L | L | I | Y | V | A | S | T | R | . | . | . | . | . | A | T | G | I | P | A | R | F | S | G | S | G | S | G | T | E | F |

Kabat - CDR L2 / Chothia - CDR L2 / Contact - CDR L2

|  | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |  |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | L | T | F | G | G | G | T | K | V | E | I | K | IGKJ4 |
| 81.39 SVDH | T | L | T | I | S | L | Q | S | E | D | F | A | V | Y | Y | C | Q | H | V | H | N | W | P | P | R | . | . | . | . | . | L | T | F | G | G | G | S | K | V | E | I | K |  |

Kabat - CDR L3 / Chothia - CDR L3 / Contact - CDR L3

Light Chain, Kappa

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 81.39 SVSH | E | I | V | . | T | Q | S | P | A | T | L | S | V | S | P | G | E | R | A | T | L | S | C | R | A | S | Q | . | . | . | . | . | . | S | V | S | . | H | N | L | A | W | Y |

Kabat - CDR L1: positions 24-34
Chothia - CDR L1: positions 24-34
Contact - CDR L1: positions 30-36

|  | 37 | 38 | 39 | 40 | 41 | 42 | 43 | 44 | 45 | 46 | 47 | 48 | 49 | 50 | 51 | 52 | 53 | 54 | A | B | C | D | E | 55 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G | I | P | A | R | F | S | G | S | G | S | G | T | E | F |
| 81.39 SVSH | Q | Q | K | P | G | Q | A | P | R | L | L | I | Y | . | S | A | S | T | R | . | . | . | . | . | A | T | G | I | P | A | R | F | S | G | S | G | S | G | T | E | F |

Kabat - CDR L2: positions 50-56
Chothia - CDR L2: positions 50-56
Contact - CDR L2: positions 46-55

|  | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | L | T | F | G | G | G | T | K | V | E | I | K |
| 81.39 SVSH | T | L | T | I | S | . | A | I | S | L | Q | S | E | D | F | A | V | Y | Y | C | Q | . | H | N | W | P | P | R | . | . | L | T | F | G | G | G | . | S | K | V | E | I | K |

Kabat - CDR L3: positions 89-97
Chothia - CDR L3: positions 89-97
Contact - CDR L3: positions 89-96

IGKJ4

Light Chain, Kappa

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 81.39 SVSH.NFP | E | I | V | T | Q | S | P | A | T | L | S | V | S | P | G | E | R | A | T | L | S | C | R | A | S | Q | . | . | . | . | . | . | S | V | S | H | N | L | A | W | Y |  |

Kabat - CDR L1 / Chothia - CDR L1 (positions 24–34) ; Contact - CDR L1 (positions 30–36)

|  | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 |
|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G |
| 81.39 SVSH.NFP | Q | Q | K | P | G | Q | A | P | R | L | L | I | Y | V | A | S | T | R | . | . | . | . | . | A | T | G |

Kabat - CDR L2 / Chothia - CDR L2 (positions 50–56) ; Contact - CDR L2 (positions 46–55)

|  | 58 | 59 | 60 | 61 | 62 | 63 | 64 | 65 | 66 | 67 | 68 | 69 | 70 | 71 |
|---|---|---|---|---|---|---|---|---|---|---|---|---|---|---|
| IGKV3-15*01 | I | P | A | R | F | S | G | S | G | S | G | T | E | F |
| 81.39 SVSH.NFP | I | P | A | R | F | S | G | S | G | S | G | T | E | F |

|  | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | L | T | F | G | G | G | T | K | V | E | I | K |
| 81.39 SVSH.NFP | T | L | A | I | S | S | L | Q | S | E | D | F | A | V | Y | Y | C | Q | H | Y | N | N | A | P | . | . | . | P | R | . | L | T | F | G | G | G | T | K | V | E | I | K |

Kabat - CDR L3 / Chothia - CDR L3 / Contact - CDR L3 (positions 89–97) ; IGKJ4

FIG. 29A

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H |   |   | W | V | R | Q | A | P | G | K |
| 81.39 SVSH.NFP | E | V | Q | L | V | E | S | G | G | G | V | V | Q | P | G | R | S | L | R | L | S | C | A | A | S | G | F | T | F | S | S | H | N | R | A | M | H |   | W | V | R | Q | A | P | G | K |

(Chothia - CDR H1: 26–32; Kabat - CDR H1: 31–35B; Contact - CDR H1: 30–35B)

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 SVSH.NFP | G | L | E | W | V | A | L | I | V | A | F | . | . | D | G | S | K | Q | Y | Y | A | D | S | V | K | G | R | F | T | I | S | R | D | N | S | K | N | T | V | F | L | Q | M | N | S | L |

(Kabat - CDR H2: 50–65; Chothia - CDR H2: 52–56; Contact - CDR H2: 47–58)

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | IGHJ1*01 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | Q | H | W | G | Q | G | T | L | V | T | V | S | S |
| 81.39 SVSH.NFP | R | P | E | D | T | A | V | Y | Y | C | A | V | P | G | P | I | F | G | I | P | P | W | S | Y | . | . | . | . | . | F | D | H | W | G | Q | G | T | L | V | T | V | S | S |

(Kabat - CDR H3: 95–102; Chothia - CDR H3: 95–102; Contact - CDR H3: 93–101)

*FIG. 29B*

Light Chain, Kappa

```
              1  2  3  4  5  6  7  8  9 10 11 12 13 14 15 16 17 18 19 20 21 22 23 24 25 26 27 A  B  C  D  E  F 28 29 30 31 32 33 34 35 36
IGKV3-15*01   E  I  V  M  T  Q  S  P  A  T  L  S  V  S  P  G  E  R  A  T  L  S  C  R  A  S  Q  .  .  .  .  .  .  S  V  S  S  N  L  A  W  Y
81.39 SVDS.F  E  I  V  L  T  Q  S  P  A  T  L  S  V  S  P  G  E  R  A  T  L  S  C  R  A  S  Q  .  .  .  .  .  .  S  V  D  S  N  L  A  W  Y 37 38 39 40 41 42 43 44 45 46 47 48 49 50 51 52 53 54 A  B  C  D  E 55 56 57 58 59 60 61 62 63 64 65 66 67 68 69 70 71
IGKV3-15*01   Q  Q  K  P  G  Q  A  P  R  L  L  I  Y  G  A  S  T  R  .  .  .  .  .  A  T  G  I  P  A  R  F  S  G  S  G  S  G  T  E  F
81.39 SVDS.F  Q  Q  K  P  G  Q  A  P  R  L  L  I  Y  V  A  S  T  R  .  .  .  .  .  A  T  G  I  P  A  R  F  S  G  S  G  S  G  T  E  F 72 73 74 75 76 77 78 79 80 81 82 83 84 85 86 87 88 89 90 91 92 93 94 95 A  B  C  D  E  F 96 97 98 99 100 101 102 103 104 105 106 107
IGKV3-15*01   T  L  T  I  S  S  L  Q  S  E  D  F  A  V  Y  Y  C  Q  Q  Y  N  N  W  P  .  .  .  .  .  .  L  T  F  G  G   G   T   K   V   E   I   K
81.39 SVDS.F  T  L  T  I  S  S  L  Q  S  E  D  F  A  V  Y  Y  C  Q  H  V  D  N  F  P  P  R  .  .  .  .  L  T  F  G  G   G   S   K   V   E   I   K   IGKJ4
```

FIG. 30A

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 81.39 SVDS.F | V | V | Q | L | V | E | S | G | G | G | V | V | Q | P | G | R | S | L | R | L | S | C | A | A | S | G | F | A | F | H | N | R | A | M | H | . | . | W | V | R | Q | A | P | G | K |

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 SVDS.F | G | L | E | W | V | A | L | I | F | . | . | . | D | G | S | K | Q | Y | Y | A | D | S | V | K | G | R | F | T | I | S | R | D | N | S | K | N | T | V | F | L | Q | M | N | S | L |

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | D | H | W | G | Q | G | T | L | V | T | V | S | S |
| 81.39 SVDS.F | R | P | E | D | T | A | V | Y | Y | C | A | V | P | G | P | I | F | G | I | F | P | P | M | S | Y | . | . | . | . | F | D | H | W | G | Q | G | T | L | V | T | V | S | S |

IGHJ1*01

FIG. 30B

Light Chain, Kappa

```
            1  2  3  4  5  6  7  8  9 10 11 12 13 14 15 16 17 18 19 20 21 22 23 24 25 26 27  A  B  C  D  E  F 28 29 30 31 32 33 34 35 36
                                                                                         Kabat - CDR L1
                                                                              Chothia - CDR L1
                                                                                                              Contact - CDR L1
IGKV3-15*01 E  I  V  M  T  Q  S  P  A  T  L  S  V  S  P  G  E  R  A  T  L  S  C  R  A  S  Q  .  .  .  .  .  S  V  S  S  N  L  A  W  Y
81.39 SVDS.Y E  I  V  L  T  Q  S  P  A  T  L  S  V  S  P  G  E  R  A  T  L  S  C  R  A  S  Q  .  .  .  .  .  S  V  D  S  N  L  A  W  Y 37 38 39 40 41 42 43 44 45 46 47 48 49 50 51 52 53 54  A  B  C  D  E 55 56 57 58 59 60 61 62 63 64 65 66 67 68 69 70 71
                                                  Kabat - CDR L2
                                       Chothia - CDR L2
                                                        Contact - CDR L2
IGKV3-15*01 Q  Q  K  P  G  Q  A  P  R  L  L  I  Y  G  A  S  T  R  .  .  .  .  .  A  T  G  I  P  A  R  F  S  G  S  G  S  G  T  E  F
81.39 SVDS.Y Q  Q  K  P  G  Q  A  P  R  L  L  I  Y  V  A  S  T  R  .  .  .  .  .  A  T  G  I  P  A  R  F  S  G  S  G  S  G  T  E  F 72 73 74 75 76 77 78 79 80 81 82 83 84 85 86 87 88 89 90 91 92 93 94 95  A  B  C  D  E  F 96 97 98 99 100 101 102 103 104 105 106 107
                                                                  Kabat - CDR L3
                                                                  Chothia - CDR L3
                                                                     Contact - CDR L3
IGKV3-15*01 T  L  T  I  S  S  L  Q  S  E  D  F  A  V  Y  Y  C  Q  Q  Y  N  N  W  P  .  .  .  .  .  .  L  T  F  G  G  G  T  K  V  E  I  K  IGKJ4
81.39 SVDS.Y T  L  T  I  H  I  S  Q  S  E  D  F  A  V  Y  Y  C  Q  H  Y  S  N  W  P  .  .  P  R  .  .  L  T  F  G  G  G  S  K  V  E  I  K
```

FIG. 31A

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 81.39 SVDS.Y | E | V | Q | L | V | E | S | G | G | G | V | V | Q | P | G | R | S | L | R | L | S | C | A | A | S | G | F | A | N | R | A | M | H | . | . | W | V | R | Q | A | P | G | K | |

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 81.39 SVDS.Y | G | L | E | W | V | A | L | I | Y | F | . | . | D | G | S | K | Q | Y | Y | A | D | S | V | K | G | R | F | T | I | S | R | D | N | S | K | N | T | V | F | L | Q | M | N | S | L |

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | | IGHJ1*01 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | Q | H | W | G | Q | G | T | L | V | T | V | S | S | | |
| 81.39 SVDS.Y | R | E | D | T | A | V | Y | Y | C | A | V | P | G | P | I | F | G | I | F | P | P | W | S | Y | . | . | . | . | . | F | D | H | W | G | Q | G | T | L | V | T | V | S | S | | |

FIG. 31B

Light Chain, Kappa

```
              1  2  3  4  5  6  7  8  9  10 11 12 13 14 15 16 17 18 19 20 21 22 23 24 25 26 27 A  B  C  D  E  F  28 29 30 31 32 33 34 35 36
IGKV3-15*01   E  I  V  M  T  Q  S  P  A  T  L  S  V  S  P  G  E  R  A  T  L  S  C  R  A  S  Q  .  .  .  .  .  .  S  V  S  S  N  L  A  W  Y
39.29D2C4     E  T  T  L  T  Q  S  P  A  T  L  S  V  S  P  G  E  R  A  T  L  S  C  R  A  S  Q  .  .  .  .  .  .  V  T  S  H  N  L  A  W  Y 37 38 39 40 41 42 43 44 45 46 47 48 49 50 51 52 53 54 A  B  C  D  E  55 56 57 58 59 60 61 62 63 64 65 66 67 68 69 70 71
IGKV3-15*01   Q  Q  K  P  G  Q  A  P  R  L  L  I  Y  G  A  S  T  R  .  .  .  .  .  A  T  G  I  P  A  R  F  S  G  S  G  S  G  T  E  F
39.29D2C4     Q  Q  K  P  G  Q  A  P  R  L  L  I  Y  G  A  S  T  R  .  .  .  .  .  A  S  G  I  P  A  R  F  S  G  S  G  S  G  T  D  Y 72 73 74 75 76 77 78 79 80 81 82 83 84 85 86 87 88 89 90 91 92 93 94 95 A  B  C  D  E  F  96 97 98 99 100 101 102 103 104 105 106 107
IGKV3-15*01   T  L  T  I  S  S  L  Q  S  E  D  F  A  V  Y  Y  C  Q  Q  Y  N  N  W  P  .  .  .  .  .  .  L  T  F  G  G  G  T  K  V  E  I  K
39.29D2C4     T  L  T  I  S  S  L  Q  S  E  D  F  A  V  Y  Y  C  Q  Q  S  H  S  N  W  P  P  R  .  .  .  .  L  T  F  G  G  G  T  K  V  E  I  K   IGKJ4
```

FIG. 32A

Heavy Chain

```
Kabat number   1  2  3  4  5  6  7  8  9 10 11 12 13 14 15 16 17 18 19 20 21 22 23 24 25 26 27 28 29 30 31 32 33 34 35 A  B  36 37 38 39 40 41 42 43
IGHV3-30*01    Q  V  Q  L  V  E  S  G  G  G  V  V  Q  P  G  R  S  L  R  L  S  C  A  A  S  G  F  T  F  S  S  Y  A  M  H  .  .  W  V  R  Q  A  P  G  K
39.29D2C4      E  V  Q  L  V  Q  S  G  G  G  V  V  Q  P  G  Q  S  L  R  L  S  C  A  A  S  G  L  T  F  S  S  Y  A  V  H  .  .  W  V  R  Q  A  P  G  K
                                                                                        Chothia - CDR H1
                                                                                     Kabat - CDR H1
                                                                                        Contact - CDR H1

Kabat number  44 45 46 47 48 49 50 51 52 A  B  C  53 54 55 56 57 58 59 60 61 62 63 64 65 66 67 68 69 70 71 72 73 74 75 76 77 78 79 80 81 82 A  B  C
IGHV3-30*01    G  L  E  W  V  A  V  I  S  Y  .  .  D  G  S  N  K  Y  Y  A  D  S  V  K  G  R  F  T  I  S  R  D  N  S  K  N  T  L  Y  L  Q  M  N  S  L
39.29D2C4      G  L  E  W  V  T  I  I  S  Y  .  .  D  G  A  N  Q  Y  Y  A  D  S  V  K  G  R  F  T  I  S  R  D  N  S  K  N  T  V  Y  L  Q  M  N  S  L
                                       Kabat - CDR H2
                                           Chothia - CDR H2
                                              Contact - CDR H2

Kabat number  83 84 85 86 87 88 89 90 91 92 93 94 95 96 97 98 99 100 A  B  C  D  E  F  G  H  I  J  K  101 102 103 104 105 106 107 108 109 110 111 112 113
IGHV3-30*01    R  A  E  D  T  A  V  Y  Y  C  A  R  .
39.29D2C4      R  P  E  D  T  A  V  Y  Y  C  A  V  P  G  P  V  F  G  I  F  P  P  W  S  V  .  .  F  D  Y  W  G  Q  G  T  L  V  T  V  S  S        IGHJ4
                                              Kabat - CDR H3
                                           Chothia - CDR H3
                                              Contact - CDR H3
```

FIG. 32B

Light Chain, Kappa

```
            1  2  3  4  5  6  7  8  9  10 11 12 13 14 15 16 17 18 19 20 21 22 23 24 25 26 27 A  B  C  D  E  F  28 29 30 31 32 33 34 35 36
IGKV3-15*01 E  I  V  M  T  Q  S  P  A  T  L  S  V  S  P  G  E  R  A  T  L  S  C  R  A  S  Q  .  .  .  .  .  .  S  V  S  S  N  L  A  W  Y
39.29D8C2   E  I  V  L  T  Q  S  P  A  T  L  S  V  S  P  G  E  R  A  T  L  S  C  R  A  S  Q  .  .  .  .  .  .  V  I  S  H  M  L  A  W  Y
```

Kabat - CDR L1
            Chothia - CDR L1
                                     Contact - CDR L1

```
            37 38 39 40 41 42 43 44 45 46 47 48 49 50 51 52 53 54 A  B  C  D  E  55 56 57 58 59 60 61 62 63 64 65 66 67 68 69 70 71
IGKV3-15*01 Q  Q  K  P  G  Q  A  P  R  L  L  I  Y  G  A  S  T  R  .  .  .  .  .  A  T  G  I  P  A  R  F  S  G  S  G  S  G  T  E  F
39.29D8C2   Q  Q  K  P  G  Q  A  P  R  L  L  I  Y  G  A  S  T  R  .  .  .  .  .  A  S  G  I  P  A  R  F  S  G  S  G  S  G  T  D  Y
```

Kabat - CDR L2
            Chothia - CDR L2
                                     Contact - CDR L2

```
            72 73 74 75 76 77 78 79 80 81 82 83 84 85 86 87 88 89 90 91 92 93 94 95 A  B  C  D  E  F  96 97 98 99 100 101 102 103 104 105 106 107
IGKV3-15*01 T  L  T  I  S  S  L  Q  S  E  D  F  A  V  Y  Y  C  Q  Q  Y  N  N  W  P  .  .  .  .  .  .  L  T  F  G  G   G   T   K   V   E   I   K
39.29D8C2   T  L  T  I  S  H  L  Q  S  E  D  F  A  V  Y  Y  C  Q  H  Y  S  N  W  P  P  R  .  .  .  .  L  T  F  G  G   G   T   K   V   E   I   K   IGKJ4
```

Kabat - CDR L3
            Chothia - CDR L3
                                     Contact - CDR L3

*FIG. 33A*

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 39.29D8C2 | Q | V | Q | L | V | Q | S | G | G | G | V | V | Q | P | G | K | S | L | R | L | S | C | A | A | S | G | L | T | F | S | S | Y | A | V | H | . | . | W | V | R | Q | A | P | G | K |

Kabat - CDR H1: 31–35B
Chothia - CDR H1: 26–32
Contact - CDR H1: 30–35B

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 39.29D8C2 | G | L | E | W | V | T | L | I | S | Y | . | . | D | G | A | N | Y | Y | A | D | S | V | K | G | R | F | T | I | S | R | D | N | S | K | N | T | V | Y | L | Q | M | N | S | L | |

Kabat - CDR H2: 50–65
Chothia - CDR H2: 52–56
Contact - CDR H2: 47–58

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | D | Y | W | G | Q | G | T | L | V | T | V | S | S | IGHJ4 |
| 39.29D8C2 | R | P | E | D | T | A | V | Y | Y | C | A | V | P | G | P | V | F | G | I | P | P | W | S | Y | . | . | . | . | . | F | D | N | W | G | Q | G | T | L | V | T | V | S | S | |

Kabat - CDR H3: 95–102
Chothia - CDR H3: 95–102
Contact - CDR H3: 93–101

FIG. 33B

Light Chain, Kappa

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 39.29NCv1   | E | I | V | L | T | Q | S | P | A | T | L | S | V | S | P | G | E | R | A | T | L | S | C | R | A | S | Q | . | . | . | . | . | . | V | I | S | H | N | L | A | W | Y |

|  | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G | I | P | A | R | F | S | G | S | G | S | G | T | E | F |
| 39.29NCv1   | Q | Q | K | P | G | Q | A | P | R | L | L | I | Y | G | A | S | T | R | . | . | . | . | . | A | S | G | I | P | A | R | F | S | G | S | G | S | G | T | D | Y |

|  | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | L | T | F | G | G | G | T | K | V | E | I | K |
| 39.29NCv1   | T | L | T | I | Q | L | Q | P | D | F | A | V | Y | Y | C | Q | Y | S | N | W | P | P | R | . | . | . | . | . | . | L | T | F | G | G | G | T | K | V | E | I | K | |

Light Chain, Kappa

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 39.29D8E7 | E | I | V | M | T | Q | S | P | A | T | L | S | V | S | P | G | E | R | A | T | L | S | C | R | A | S | Q | . | . | . | . | . | . | V | I | S | H | N | L | A | W | Y |

Kabat - CDR L1: positions 24–34
Chothia - CDR L1
Contact - CDR L1

| | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G | I | P | A | R | F | S | G | S | G | S | G | T | E | F |
| 39.29D8E7 | Q | Q | K | P | G | Q | A | P | R | L | L | I | Y | G | A | S | T | R | . | . | . | . | . | A | S | G | I | P | A | R | F | S | G | S | G | S | G | T | D | Y |

Kabat - CDR L2
Chothia - CDR L2
Contact - CDR L2

| | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | L | T | F | G | G | G | T | K | V | E | I | K | IGKJ4 |
| 39.29D8E7 | T | L | T | I | S | D | L | Q | S | E | D | F | A | V | Y | Y | C | Q | Q | Y | H | N | W | P | P | R | . | . | . | . | L | T | F | G | G | G | T | K | V | E | I | K | |

Kabat - CDR L3
Chothia - CDR L3
Contact - CDR L3

*FIG. 35A*

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | | | W | V | R | Q | A | P | G | K |
| 39.29D8E7 | Q | V | Q | L | V | Q | S | G | G | G | V | V | Q | P | G | R | S | L | R | L | S | C | A | A | S | G | L | T | F | S | S | Y | A | V | H | | | W | V | R | Q | A | P | G | K |

Kabat - CDR H1: 31-35B  
Chothia - CDR H1: 26-32  
Contact - CDR H1: 30-35B

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 39.29D8E7 | G | L | E | W | V | T | L | I | S | Y | . | . | D | G | A | N | Q | Y | Y | A | D | S | V | K | G | R | F | T | I | S | R | D | N | S | K | N | T | V | Y | L | Q | M | N | S | L |

Kabat - CDR H2: 50-65  
Chothia - CDR H2: 52-56  
Contact - CDR H2: 47-58

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | F | D | Y | W | G | Q | G | T | L | V | T | V | S | S | IGHJ4 |
| 39.29D8E7 | R | P | E | D | T | A | V | Y | Y | C | A | V | P | V | F | G | I | P | P | W | S | Y | . | . | . | . | . | . | . | F | D | N | W | G | Q | G | L | L | V | T | V | S | S | |

Kabat - CDR H3: 95-102  
Chothia - CDR H3: 95-102  
Contact - CDR H3: 93-101

FIG. 35B

Light Chain, Kappa

```
                 1  2  3  4  5  6  7  8  9 10 11 12 13 14 15 16 17 18 19 20 21 22 23 24 25 26 27   A  B  C  D  E  F 28 29 30 31 32 33 34 35 36
IGKV3-15*01      E  I  V  M  T  Q  S  P  A  T  L  S  V  S  P  G  E  R  A  T  L  S  C  R  A  S  Q   .  .  .  .  .  .  S  V  S  S  N  L  A  W  Y
39.29.NFPP       E  I  V  L  T  Q  S  P  A  T  L  S  V  S  P  G  E  R  A  T  L  S  C  R  A  S  Q   .  .  .  .  .  .  V  I  S  H  N  L  A  W  Y
                                                                                                                   └─────────────┘
                                                                                                                   Kabat - CDR L1
                                                                                                                   Chothia - CDR L1
                                                                                                                        Contact - CDR L1

37 38 39 40 41 42 43 44 45 46 47 48 49 50 51 52 53 54  A  B  C  D  E 55 56 57 58 59 60 61 62 63 64 65 66 67 68 69 70 71
IGKV3-15*01      Q  Q  K  P  G  Q  A  P  R  L  L  I  Y  G  A  S  T  R   .  .  .  .  . A  T  G  I  P  A  R  F  S  G  S  G  S  G  T  E  F
39.29.NFPP       Q  Q  K  P  G  Q  A  P  R  L  L  I  Y  G  A  S  T  R   .  .  .  .  . A  S  G  I  P  A  R  F  S  G  S  G  S  G  T  D  Y
                                                           └──────────┘
                                                           Kabat - CDR L2
                                                           Chothia - CDR L2
                                                             Contact - CDR L2

72 73 74 75 76 77 78 79 80 81 82 83 84 85 86 87 88 89 90 91 92 93 94 95  A  B  C  D  E  F 96 97 98 99 100 101 102 103 104 105 106 107
IGKV3-15*01      T  L  T  I  S  S  L  Q  S  E  D  F  A  V  Y  Y  C  Q  Q  Y  N  N  W  P   .  .  .  .  .  . L  T  F  G  G  G   T   K   V   E   I   K   IGKJ4
39.29.NFPP       T  L  T  I  T  L  Q  S  E  D  F  A  V  Y  Y  C  Q  H  Y  S  N  F  P  R   .  .  .  .  .  . L  T  F  G  G  G   T   K   V   E   I   K
                                                                         └──────────────────────────────┘
                                                                         Kabat - CDR L3
                                                                         Chothia - CDR L3
                                                                           Contact - CDR L3
```

FIG. 36A

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | Q | V | Q | L | V | E | S | G | G | G | V | V | Q | P | G | R | S | L | R | L | S | C | A | A | S | G | F | T | F | S | S | Y | A | M | H | . | . | W | V | R | Q | A | P | G | K |
| 39.29.NFPP | E | V | Q | L | V | Q | S | G | G | G | V | V | Q | P | G | K | S | L | R | L | S | C | A | A | S | G | L | T | F | S | S | Y | A | V | H | . | . | W | V | R | Q | A | P | G | K |

Kabat - CDR H1
Chothia - CDR H1
Contact - CDR H1

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C | 
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 39.29.NFPP | G | L | E | W | V | T | L | I | S | V | . | . | D | G | T | N | K | Y | Y | A | D | S | V | K | G | R | F | T | I | S | R | D | N | S | K | N | T | V | Y | L | Q | M | N | S | L |

Kabat - CDR H2
Chothia - CDR H2
Contact - CDR H2

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | . | . | . | . | . | . | . | . | . | . | . | . | . | . | . | . | . | . | . | . | . | . | . | . | . | . | . | . | . | |
| 39.29.NFPP | R | P | E | D | T | A | V | Y | Y | C | A | V | P | G | P | V | F | G | I | F | P | P | W | S | V | . | . | . | . | F | D | Y | W | G | Q | G | T | L | V | T | V | S | S | IGHJ4 |

Kabat - CDR H3
Chothia - CDR H3
Contact - CDR H3

FIG. 36B

Light Chain, Kappa

```
              1  2  3  4  5  6  7  8  9 10 11 12 13 14 15 16 17 18 19 20 21 22 23 24 25 26 27 A  B  C  D  E  F 28 29 30 31 32 33 34 35 36
IGKV3-15*01   E  I  V  M  T  Q  S  P  A  T  L  S  V  S  P  G  E  R  A  T  L  S  C  R  A  S  Q  .  .  .  .  .  .  S  V  S  S  N  L  A  W  Y
39.29.NYPP    E  I  V  L  T  Q  S  P  A  T  L  S  V  S  P  G  E  R  A  T  L  S  C  R  A  S  Q  .  .  .  .  .  .  V  I  S  H  N  L  A  W  Y
```

Kabat - CDR L1
Chothia - CDR L1
Contact - CDR L1

```
             37 38 39 40 41 42 43 44 45 46 47 48 49 50 51 52 53 54 A  B  C  D  E 55 56 57 58 59 60 61 62 63 64 65 66 67 68 69 70 71
IGKV3-15*01   Q  Q  K  P  G  Q  A  P  R  L  L  I  Y  G  A  S  T  R  .  .  .  .  .  A  T  G  I  P  A  R  F  S  G  S  G  T  E  F
39.29.NYPP    Q  Q  K  P  G  Q  A  P  R  L  L  I  Y  G  A  S  T  R  .  .  .  .  .  A  S  G  I  P  A  R  F  S  G  S  G  T  D  Y
```

Kabat - CDR L2
Chothia - CDR L2
Contact - CDR L2

```
             72 73 74 75 76 77 78 79 80 81 82 83 84 85 86 87 88 89 90 91 92 93 94 95 A  B  C  D  E  F 96 97 98 99 100 101 102 103 104 105 106 107
IGKV3-15*01   T  L  T  I  S  S  L  Q  S  E  D  F  A  V  Y  Y  C  Q  Q  Y  N  N  W  P  .  .  .  .  .  .  L  T  F  G  G   G   T   K   V   E   I   K
39.29.NYPP    T  L  T  I  S  L  Q  S  E  D  F  A  V  Y  Y  C  Q  H  Y  S  N  V  P  P  R  .  .  .  .  .  .  L  T  F  G  G   G   T   K   V   E   I   K
```

Kabat - CDR L3
Chothia - CDR L3
Contact - CDR L3

IGKJ4

*FIG. 37A*

Heavy Chain

| | Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | | Q | V | Q | L | V | E | S | G | G | G | V | V | Q | P | G | R | S | L | R | L | S | C | A | A | S | G | F | T | F | S | S | Y | A | M | H | | | W | V | R | Q | A | P | G | K |
| 39.29.NYPP | | V | Q | L | V | Q | S | G | G | G | V | V | Q | P | G | K | S | L | R | L | S | C | A | A | S | G | T | T | F | S | S | Y | A | V | H | | | W | V | R | Q | A | P | G | K |

Kabat - CDR H1
Chothia - CDR H1
Contact - CDR H1

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | G | L | E | W | V | A | V | I | S | Y | . | . | D | G | S | N | K | Y | Y | A | D | S | V | K | G | R | F | T | I | S | R | D | N | S | K | N | T | L | Y | L | Q | M | N | S | L |
| 39.29.NYPP | G | L | E | W | V | T | I | T | S | Y | . | . | D | G | A | N | Y | Y | Y | A | D | S | V | K | G | R | F | T | I | S | R | D | N | S | K | N | T | V | Y | L | Q | M | N | S | L |

Kabat - CDR H2
Chothia - CDR H2
Contact - CDR H2

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV3-30*01 | R | A | E | D | T | A | V | Y | Y | C | A | R | . | | | | | | | | | | | | | | | | | F | D | Y | W | G | Q | G | T | L | V | T | V | S | S | |
| 39.29.NYPP | R | E | E | D | T | A | V | Y | Y | C | A | R | A | V | P | G | P | V | F | G | I | F | P | P | W | S | Y | . | . | F | D | N | W | G | Q | G | I | L | V | T | V | S | S | IGHJ4 |

Kabat - CDR H3
Chothia - CDR H3
Contact - CDR H3

*FIG. 37B*

Light Chain, Kappa

```
                                                          Kabat - CDR L1
                                                          Chothia - CDR L1
                                                                   Contact - CDR L1
             1  2  3  4  5  6  7  8  9 10 11 12 13 14 15 16 17 18 19 20 21 22 23 24 25 26 27  A  B  C  D  E  F 28 29 30 31 32 33 34 35 36
IGKV3-15*01  E  I  V  M  T  Q  S  P  A  T  L  S  V  S  P  G  E  R  A  T  L  S  C  R  A  S  Q  .  .  .  .  .  .  S  V  S  S  N  L  A  W  Y
39.29.NWPP   E  I  V  L  T  Q  S  P  A  T  L  S  V  S  P  G  E  R  A  T  L  S  C  R  A  S  Q  .  .  .  .  .  .  V  I  S  H  N  L  A  W  Y Kabat - CDR L2
                                                          Chothia - CDR L2
                                                                   Contact - CDR L2
             37 38 39 40 41 42 43 44 45 46 47 48 49 50 51 52 53 54  A  B  C  D  E 55 56 57 58 59 60 61 62 63 64 65 66 67 68 69 70 71
IGKV3-15*01  Q  Q  K  P  G  Q  A  P  R  L  L  I  Y  G  A  S  T  R  .  .  .  .  .  A  T  G  I  P  A  R  F  S  G  S  G  S  G  T  E  F
39.29.NWPP   Q  Q  K  P  G  Q  A  P  R  L  L  I  Y  G  A  S  T  R  .  .  .  .  .  A  S  G  I  P  A  R  F  S  G  S  G  S  G  T  D  Y Kabat - CDR L3
                                                          Chothia - CDR L3
                                                                   Contact - CDR L3
             72 73 74 75 76 77 78 79 80 81 82 83 84 85 86 87 88 89 90 91 92 93 94 95  A  B  C  D  E  F 96 97 98 99 100 101 102 103 104 105 106 107   IGKJ4
IGKV3-15*01  T  L  T  I  S  S  L  Q  S  E  D  F  A  V  Y  Y  C  Q  Q  Y  N  N  W  P  .  .  .  .  .  .  L  T  F  G  G   G   T   K   V   E   I   K
39.29.NWPP   T  L  T  I  H  S  L  Q  S  E  D  F  A  V  Y  Y  C  Q  H  Y  S  N  W  P  P  R  .  .  .  .  L  T  F  G  G   G   T   K   V   E   I   K
```

*FIG. 38A*

Heavy Chain

```
Kabat number    1  2  3  4  5  6  7  8  9 10 11 12 13 14 15 16 17 18 19 20 21 22 23 24 25 26 27 28 29 30 31 32 33 34 35 A  B 36 37 38 39 40 41 42 43
IGHV3-30*01     Q  V  Q  L  V  E  S  G  G  G  V  V  Q  P  G  R  S  L  R  L  S  C  A  A  S  G  F  T  F  S  S  Y  A  M  H  .  .  W  V  R  Q  A  P  G  K
39.29.NWPP      V  Q  L  V  Q  S  G  G  G  V  V  Q  P  G  K  S  L  R  L  S  C  A  A  S  G  L  T  F  S  S  Y  A  V  H  .  .  W  V  R  Q  A  P  G  K
                                                                                     Chothia - CDR H1
                                                                                        Kabat - CDR H1
                                                                                        Contact - CDR H1

Kabat number   44 45 46 47 48 49 50 51 52 A  B  C 53 54 55 56 57 58 59 60 61 62 63 64 65 66 67 68 69 70 71 72 73 74 75 76 77 78 79 80 81 82 A  B  C
IGHV3-30*01     G  L  E  W  V  A  V  I  S  Y  .  .  D  G  S  N  K  Y  Y  A  D  S  V  K  G  R  F  T  I  S  R  D  N  S  K  N  T  L  Y  L  Q  M  N  S  L
39.29.NWPP      G  L  E  W  V  H  I  S  Y  .  .  D  G  A  N  I  Q  Y  A  D  S  V  K  G  R  F  T  I  S  R  D  N  S  K  N  T  V  Y  L  Q  M  N  S  L
                             Kabat - CDR H2
                                Chothia - CDR H2
                             Contact - CDR H2

Kabat number   83 84 85 86 87 88 89 90 91 92 93 94 95 96 97 98 99 100 A  B  C  D  E  F  G  H  I  J  K 101 102 103 104 105 106 107 108 109 110 111 112 113
IGHV3-30*01     R  A  E  D  T  A  V  Y  Y  C  A  R  .  .  .  .  .  .  .  .  .  .  .  .  .  .  .  .  .  F  D  Y  W  G  Q  G  T  L  V  T  V  S  S
39.29.NWPP      R  B  E  D  T  A  V  Y  Y  C  A  V  P  G  P  V  F  G  I  F  P  P  M  S  V  .  .  .  .  F  D  N  W  G  Q  G  T  L  H  V  T  V  S  S     IGHJ4
                                              Kabat - CDR H3
                                                Chothia - CDR H3
                                                Contact - CDR H3
```

FIG. 38B

Light Chain, Kappa

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | |
| IGKV3-15*01 | E | I | V | M | T | Q | S | P | A | T | L | S | V | S | P | G | E | R | A | T | L | S | C | R | A | S | Q | . | . | . | . | . | . | S | V | S | S | N | L | A | W | Y |
| 39.18B11 | E | I | V | L | T | Q | S | P | A | T | L | S | V | S | P | G | E | R | V | T | L | S | C | R | A | S | Q | . | . | . | . | . | . | S | V | A | N | N | L | A | W | Y |

Kabat - CDR L1 / Chothia - CDR L1 / Contact - CDR L1

|  | 37 | 38 | 39 | 40 | 41 | 42 | 43 | 44 | 45 | 46 | 47 | 48 | 49 | 50 | 51 | 52 | 53 | 54 | A | B | C | D | E | 55 | 56 | 57 | 58 | 59 | 60 | 61 | 62 | 63 | 64 | 65 | 66 | 67 | 68 | 69 | 70 | 71 |
|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | Q | Q | K | P | G | Q | A | P | R | L | L | I | Y | G | A | S | T | R | . | . | . | . | . | A | T | G | I | P | A | R | F | S | G | S | G | S | G | T | E | F |
| 39.18B11 | Q | Q | K | P | G | Q | S | P | R | L | L | I | Y | G | A | S | T | R | . | . | . | . | . | D | T | G | I | P | A | R | F | S | G | S | G | S | G | T | E | F |

Kabat - CDR L2 / Chothia - CDR L2 / Contact - CDR L2

|  | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGKV3-15*01 | T | L | T | I | S | S | L | Q | S | E | D | F | A | V | Y | Y | C | Q | Q | Y | N | N | W | P | . | . | . | . | . | . | Y | T | F | G | Q | G | T | K | V | E | I | K |
| 39.18B11 | T | L | T | I | S | S | L | Q | S | E | D | F | A | V | Y | Y | C | Q | Q | Y | N | N | W | P | . | . | . | . | . | . | Y | T | F | G | Q | G | T | K | V | E | I | K |

Kabat - CDR L3 / Chothia - CDR L3 / Contact - CDR L3 ... IGKJ2

FIG. 39A

Heavy Chain

```
Kabat number  1  2  3  4  5  6  7  8  9  10 11 12 13 14 15 16 17 18 19 20 21 22 23 24 25 26 27 28 29 30 31 32 33 34 35 A  B  36 37 38 39 40 41 42 43
IGHV1-69*01   Q  V  Q  L  V  Q  S  G  A  E  V  K  K  P  G  S  S  V  K  V  S  C  K  A  S  G  G  T  F  S  S  Y  A  I  S  .  .  W  V  R  Q  A  P  G  Q
39.18B11      E  V  Q  L  V  Q  S  G  A  E  V  K  K  P  G  S  S  M  K  V  S  C  K  A  S  G  S  I  F  S  N  Y  G  I  S  .  .  W  V  R  Q  A  P  G  Q
                                                                                    Chothia - CDR H1
                                                                                       Kabat - CDR H1
                                                                                       Contact - CDR H1

Kabat number  44 45 46 47 48 49 50 51 52 A  B  C  53 54 55 56 57 58 59 60 61 62 63 64 65 66 67 68 69 70 71 72 73 74 75 76 77 78 79 80 81 82 A  B  C
IGHV1-69*01   G  L  E  W  M  G  G  I  I  P  .  .  I  F  G  T  A  N  Y  A  Q  K  F  Q  G  R  V  T  I  T  A  D  E  S  T  S  T  A  Y  M  E  L  S  S  L
39.18B11      G  L  E  W  M  G  G  I  I  P  .  .  I  F  G  A  A  N  Y  A  Q  K  F  Q  G  R  V  T  I  T  A  D  E  S  T  S  T  V  Y  M  E  V  R  S  L
                                   Contact - CDR H2
                                   Chothia - CDR H2
                                      Kabat - CDR H2

Kabat number  83 84 85 86 87 88 89 90 91 92 93 94 95 96 97 98 99 100 A  B  C  D  E  F  G  H  I  J  K  101 102 103 104 105 106 107 108 109 110 111 112 113
IGHV1-69*01   R  S  E  D  T  A  V  Y  Y  C  A  R                                                    F  Q  H                W  G  Q  G  T  L  V  T  V  S  S  IGHJ1*01
39.18B11      R  S  E  D  T  A  V  Y  Y  C  A  R  R  Q  Q  H  Y  K  G  Y                            V  H  H                W  G  Q  G  T  L  V  T  V  S  S
                                                     Contact - CDR H3
                                                     Chothia - CDR H3
                                                     Kabat - CDR H3
```

FIG. 39B

Light Chain, Kappa

```
                     1  2  3  4  5  6  7  8  9 10 11 12 13 14 15 16 17 18 19 20 21 22 23 24 25 26 27  A  B  C  D  E  F 28 29 30 31 32 33 34 35 36
                                                                                                                                  Kabat - CDR L1
                                                                                                                                Chothia - CDR L1
                                                                                                                                  Contact - CDR L1
IGKV3-15*01          E  I  V  M  T  Q  S  P  A  T  L  S  V  S  P  G  E  R  A  T  L  S  C  R  A  S  Q  .  .  .  .  S  V  S  S  N  L  A  W  Y
39.18.E12            E  I  V  L  T  Q  S  P  A  T  L  S  V  S  P  G  E  R  V  T  L  S  C  R  A  S  Q  .  .  .  .  S  V  N  N  L  A  W  Y 37 38 39 40 41 42 43 44 45 46 47 48 49 50 51 52 53 54  A  B  C  D  E 55 56 57 58 59 60 61 62 63 64 65 66 67 68 69 70 71
                                                            Kabat - CDR L2
                                                          Chothia - CDR L2
                                                           Contact - CDR L2
IGKV3-15*01          Q  Q  K  P  G  Q  A  P  R  L  L  I  Y  G  A  S  T  R  .  .  .  .  A  T  G  I  P  A  R  F  S  G  S  G  S  G  T  E  F
39.18.E12            Q  Q  K  P  G  Q  S  P  R  L  L  I  Y  G  A  S  T  R  .  .  .  .  D  T  G  I  P  A  R  F  S  G  S  G  S  G  T  E  F 72 73 74 75 76 77 78 79 80 81 82 83 84 85 86 87 88 89 90 91 92 93 94 95  A  B  C  D  E  F 96 97 98 99 100 101 102 103 104 105 106 107
                                                                                    Kabat - CDR L3
                                                                                  Chothia - CDR L3
                                                                                   Contact - CDR L3                                             IGKJ2
IGKV3-15*01          T  L  T  I  S  S  L  Q  S  E  D  F  A  V  Y  Y  C  Q  Q  Y  N  N  W  P  .  .  .  .  .  .  Y  T  F  G  Q  G  T  K  V  E  I  K
39.18.E12            T  L  T  I  S  S  L  Q  S  E  D  F  A  V  Y  Y  C  Q  Q  Y  N  N  W  P  P  M  .  .  .  .  Y  T  F  G  Q  G  T  K  V  E  I  K
```

*FIG. 40A*

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-69*01 | Q | V | Q | L | V | Q | S | G | A | E | V | K | K | P | G | S | S | V | K | V | S | C | K | A | S | G | G | T | F | S | S | Y | A | I | S | | | W | V | R | Q | A | P | G | Q |
| 39.18.E12 | Q | V | Q | L | V | Q | S | G | A | G | V | K | K | P | G | S | S | M | K | V | S | C | K | A | S | G | S | I | F | S | N | Y | G | I | S | | | W | V | R | Q | A | P | G | Q |

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C | L |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-69*01 | G | L | E | W | M | G | G | I | I | P | . | . | I | F | G | T | A | N | Y | A | Q | K | F | Q | G | R | V | T | I | T | A | D | E | S | T | S | T | A | Y | M | E | L | S | S | L | |
| 39.18.E12 | G | L | E | W | M | G | G | I | I | P | . | . | I | F | G | A | A | N | Y | A | Q | K | F | Q | G | R | V | T | I | T | A | D | E | S | T | S | T | V | Y | M | E | V | R | S | L | L |

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-69*01 | R | S | E | D | T | A | V | Y | Y | C | A | R | . | . | . | . | . | . | . | . | . | . | . | . | . | . | . | . | . | F | Q | H | W | G | Q | G | T | L | V | T | V | S | S | IGHJ1*01 |
| 39.18.E12 | R | S | E | D | T | A | V | Y | Y | C | A | R | R | Q | L | V | K | G | Y | . | . | . | . | . | . | . | . | . | . | V | A | H | W | G | Q | G | T | L | V | T | V | S | S | |

FIG. 40B

Light Chain, Kappa

```
                    1  2  3  4  5  6  7  8  9 10 11 12 13 14 15 16 17 18 19 20 21 22 23 24 25 26 27 A  B  C  D  E  F 28 29 30 31 32 33 34 35 36
IGKV1-5*03          D  I  Q  M  T  Q  S  P  S  T  L  S  A  S  V  G  D  R  V  T  I  T  C  R  A  S  Q  .  .  .  .  .  .  S  I  S  S  W  L  A  W  Y
36.89               D  I  V  M  T  Q  S  P  S  T  L  S  A  S  V  G  D  R  V  T  I  T  C  R  A  S  Q  .  .  .  .  .  .  S  I  G  N  W  L  A  W  Y
```

Kabat - CDR L1
Chothia - CDR L1
Contact - CDR L1

```
                   37 38 39 40 41 42 43 44 45 46 47 48 49 50 51 52 53 54 A  B  C  D  E 55 56 57 58 59 60 61 62 63 64 65 66 67 68 69 70 71
IGKV1-5*03          Q  Q  K  P  G  K  A  P  K  L  L  I  Y  K  A  S  S  L  .  .  .  .  .  E  S  G  V  P  S  R  F  S  G  S  G  S  G  T  E  F
36.89               Q  Q  K  P  G  K  A  P  K  L  L  I  Y  K  V  S  T  L  .  .  .  .  .  E  S  G  V  P  S  R  F  S  G  S  G  S  G  T  E  F
```

Kabat - CDR L2
Chothia - CDR L2
Contact - CDR L2

```
                   72 73 74 75 76 77 78 79 80 81 82 83 84 85 86 87 88 89 90 91 92 93 94 95 A  B  C  D  E  F 96 97 98 99 100 101 102 103 104 105 106 107
IGKV1-5*03          T  L  T  I  S  S  L  Q  P  D  D  F  A  T  Y  Y  C  Q  Q  Y  N  S  Y  S  .  .  .  .  .  .  Y  T  F  G  Q  G  T  K  L  E  I  K  IGKJ2
36.89               T  L  T  I  N  S  L  Q  P  D  D  F  A  T  Y  Y  C  Q  R  Y  T  S  N  S  L  Q  G  .  .  .  F  T  F  G  Q  G  T  K  L  E  I  K
```

Kabat - CDR L3
Chothia - CDR L3
Contact - CDR L3

*FIG. 41A*

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-18*01 | Q | V | Q | L | V | Q | S | G | A | E | V | K | K | P | G | A | S | V | K | V | S | C | K | A | S | G | Y | T | F | T | S | Y | G | I | S | . | . | W | V | R | Q | A | P | G | Q |
| 36.89 | Q | V | Q | L | V | Q | S | G | A | E | L | K | R | P | G | A | S | V | K | V | S | C | K | T | S | G | Y | S | F | N | N | Y | G | I | N | . | . | W | V | R | Q | A | P | G | Q |

Kabat - CDR H1: 31–35B
Chothia - CDR H1: 26–32
Contact - CDR H1: 30–35B

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-18*01 | G | L | E | W | M | G | W | I | S | A | . | . | Y | N | G | N | T | N | Y | A | Q | K | L | Q | G | R | V | T | M | T | T | D | T | S | T | S | T | A | Y | M | E | L | R | S | L |
| 36.89 | G | L | E | W | M | G | W | I | S | A | . | . | Y | T | G | N | T | H | Y | A | K | N | F | E | G | R | V | T | L | T | T | D | T | S | T | S | T | A | Y | M | E | V | V | R | S | L |

Kabat - CDR H2: 50–65
Chothia - CDR H2: 52–56
Contact - CDR H2: 47–58

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-18*01 | R | S | D | D | T | A | V | Y | Y | C | A | R | . | . | . | . | . | . | . | . | . | . | . | . | . | . | . | . | . | F | Q | H | W | G | Q | G | T | L | V | T | V | S | S IGHJ1*01 |
| 36.89 | R | S | D | D | S | A | V | Y | F | C | A | R | A | M | T | Q | G | V | V | L | V | L | R | P | G | . | . | . | . | D | Y | W | G | Q | G | T | L | V | T | V | S | S |

Kabat - CDR H3: 95–102
Chothia - CDR H3: 95–102
Contact - CDR H3: 93–101

FIG. 41B

Light Chain, Lambda

```
                                                                    ┌─ Kabat - CDR L1 ──┐
                                                                    ┌─ Chothia - CDR L1 ┐
                                                                    │ ┌ Contact - CDR L1 ┐
Kabat number  1  2  3  4  5  6  7  8  9 10 11 12 13 14 15 16 17 18 19 20 21 22 23 24 25 26 27 A  B  C  D  E  F 28 29 30 31 32 33 34 35 36
IGLV1-44*01   Q  S  V  L  T  Q  P  P  S  .  A  S  G  T  P  G  Q  R  V  T  I  S  C  S  G  S  S  S  N  .  .  .  I  G  S  N  T  V  N  W  Y
9.01F3        Q  S  S  E  L  T  Q  P  P  S  .  A  S  G  T  P  G  Q  R  V  T  I  S  C  S  G  S  T  S  N  .  .  .  I  G  Y  N  P  V  S  W  Y ┌─ Kabat - CDR L2 ─┐
                                                                 ┌─ Chothia - CDR L2 ┐
                                                                 │ ┌ Contact - CDR L2
Kabat number 37 38 39 40 41 42 43 44 45 46 47 48 49 50 51 52 53 54 A  B  C  D  E 55 56 57 58 59 60 61 62 63 64 65 66 A  B 67 68 69 70 71
IGLV1-44*01  Q  Q  L  P  G  T  A  P  K  L  L  I  Y  S  N  N  Q  R  .  .  .  .  .  P  S  G  V  P  D  R  F  S  G  S  K  .  .  S  G  T  S  A
9.01F3       Q  Q  V  P  G  T  A  P  K  L  L  I  Y  S  N  T  E  R  .  .  .  .  .  P  S  G  V  P  D  R  F  S  G  S  K  .  .  S  G  T  S  A ┌─ Kabat - CDR L3 ──┐
                                                                                     ┌─ Chothia - CDR L3 ┐
                                                                                     │ ┌ Contact - CDR L3
Kabat number 72 73 74 75 76 77 78 79 80 81 82 83 84 85 86 87 88 89 90 91 92 93 94 95 A  B  C  D  E  F 96 97 98 99 100 101 102 103 104 105 106 107
IGLV1-44*01  S  L  A  I  S  G  L  Q  S  E  D  E  A  D  Y  Y  C  A  A  W  D  D  S  L  N  G  .  .  .  .  Y  V  F  G  T   G   T   K   V   T   V   L    IGLJ1
9.01F3       S  L  A  I  S  G  L  Q  S  E  D  E  A  D  Y  Y  C  A  A  W  D  D  I  L  N  G  .  .  .  .  P  V  F  G  G   G   T   K   V   T   V   L
```

Heavy Chain

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-2*02 | Q | V | Q | L | V | Q | S | G | A | E | V | K | K | P | G | A | S | V | K | V | S | C | K | A | S | G | Y | T | F | T | G | Y | Y | M | H | | | W | V | R | Q | A | P | G | Q |
| 9.01F3 | Q | V | Q | L | V | Q | S | G | A | E | V | K | K | P | G | A | S | V | K | V | S | C | K | A | S | G | Y | T | F | N | A | Y | Y | I | H | | | W | V | R | Q | A | P | G | Q |

Kabat - CDR H1 / Chothia - CDR H1 / Contact - CDR H1

| Kabat number | 44 | 45 | 46 | 47 | 48 | 49 | 50 | 51 | 52 | A | B | C | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | A | B | C |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-2*02 | G | L | E | W | M | G | W | I | N | P | . | . | N | S | G | G | T | N | Y | A | Q | K | F | Q | G | R | V | T | M | T | R | D | T | S | I | S | T | A | Y | M | E | L | S | R | L |
| 9.01F3 | G | L | E | W | M | G | W | I | N | P | . | . | N | G | G | T | H | Y | A | R | K | F | Q | G | R | V | T | M | T | R | D | A | S | T | N | T | A | Y | M | E | L | D | R | L |

Kabat - CDR H2 / Chothia - CDR H2 / Contact - CDR H2

| Kabat number | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 | 110 | 111 | 112 | 113 | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| IGHV1-2*02 | R | S | D | D | T | A | V | Y | Y | C | A | R | . | . | . | . | . | . | . | . | . | . | . | . | . | . | . | . | . | M | D | V | W | G | Q | G | T | T | V | T | V | S | S | IGHJ6* |
| 9.01F3 | R | S | D | D | T | A | V | Y | Y | C | V | R | W | R | A | A | A | V | I | M | D | Q | F | Y | K | . | . | . | . | M | D | V | W | G | Q | G | T | L | V | T | V | S | S | 01/02/04 |

Kabat - CDR H3 / Chothia - CDR H3 / Contact - CDR H3

Human Germlines

Light Chain, Kappa

FIG. 43A

Heavy Chain

Kabat number: 1 2 3 4 5 6 7 8 9 10 11 12 13 14 15 16 17 18 19 20 21 22 23 24 25 26 27 28 29 30 31 32 33 34 35 A B 36 37 38 39 40 41 42 43

IGHV4-39*01:  Q L Q L Q E S G P G L V K P S E T L S L T C T V S G G S I S S S Y Y W G W I R Q P P G K
23.06C2:      Q V Q L Q E S G P G L V K P S E T L S L T C T V S G G S L G T A G S Y Y W G W I R Q T P G K

Kabat - CDR H1
Chothia - CDR H1
Contact - CDR H1

Kabat number: 44 45 46 47 48 49 50 51 52 A B C 53 54 55 56 57 58 59 60 61 62 63 64 65 66 67 68 69 70 71 72 73 74 75 76 77 78 79 80 81 82 A B C IGHV4-39*01:  G L E W I G S I Y . . . Y S G S T Y Y N P S L K S R V T I S V D T S K N Q F S L K L S S
23.06C2:      G M E W I G S I S . . Y S G S T Y Y H P S L K S R V T I S D D T S K N Q L F L K L R S V Kabat - CDR H2
Chothia - CDR H2
Contact - CDR H2

Kabat number: 83 84 85 86 87 88 89 90 91 92 93 94 95 96 97 98 99 100 A B C D E F G H I J K 101 102 103 104 105 106 107 108 109 110 111 112 113

IGHV4-39*01:  T A A D T A V Y Y C A R                              IGHJ2*01
23.06C2:      T A A D T A V Y Y C A R Y N W G I R Y . . . F D L W G R G T L V T V S S

Kabat - CDR H3
Chothia - CDR H3
Contact - CDR H3

Human Germlines

*FIG. 43B*

ANTI-HEMAGGLUTININ ANTIBODIES AND METHODS OF USE

RELATED APPLICATIONS

This application is a divisional of U.S. patent application Ser. No. 14/077,414, filed on 12 Nov. 2013, which claims the benefit of U.S. Provisional Application No. 61/725,859, filed on 13 Nov. 2012, the disclosures of each of which are hereby incorporated by reference in their entireties for all purposes.

SEQUENCE LISTING

This application contains a Sequence Listing which has been submitted electronically in ASCII format and is hereby incorporated by reference in its entirety. Said ASCII copy, created 27 Jan. 2016, is named P4982R1D1_SL.txt and is 222,667 bytes in size.

FIELD OF THE INVENTION

The present invention provides anti-hemagglutinin antibodies, compositions comprising anti-hemagglutinin antibodies, and methods of using the same.

BACKGROUND

Influenza virus infection causes between three and five million cases of severe illness and between 250,000 and 500,000 deaths every year around the world. In the United States alone, 5% to 20% of the population becomes infected with influenza virus each year, with the majority of these infections caused by the influenza A virus. (See, e.g., Dushoff et al., (2006) Am J Epidemiology 163:181-187; Thompson et al., (2004) JAMA 292:1333-1340; Thompson et al., (2003) JAMA 289:179-186.) Approximately 200,000 people in the United States become hospitalized with influenza-related complications every year, resulting in 7,000 to 30,000 deaths annually. The burden associated with influenza virus infection on health care costs and lost productivity is extensive. Hospitalization and deaths mainly occur in high-risk groups, such as the elderly, children, and chronically ill.

Influenza viruses are segmented membrane-enveloped negative-strand RNA viruses belonging to the Orthomyxoviridae family. Influenza A virus consists of 9 structural proteins and 1 non-structural protein, which include three virus surface proteins: hemagglutinin (HA or H), neuraminidase (NA or N), and matrix protein 2 (M2). The segmented nature of the influenza viral genome allows the mechanism of genetic reassortment (i.e., exchange of genome segments) to take place during mixed infection of a cell with different influenza viral strains. Annual epidemics of influenza occur when the antigenic properties of the viral surface proteins hemagglutinin and neuraminidase are altered. The mechanism of altered antigenicity is twofold: antigenic shift, caused by genetic rearrangement between human and animal viruses after co-infection of host cells with at least two viral subtypes, which can cause a pandemic; and antigenic drift, caused by small changes in the hemagglutinin and neuraminidase proteins on the virus surface, which can cause influenza epidemics.

Influenza A viruses may be further classified into various subtypes depending on the different hemagglutinin and neuraminidase viral proteins displayed on their surface. Each influenza A virus subtype is identified by the combination of its hemagglutinin and neuraminidase proteins. There are 16 known HA subtypes (H1-H16) and 9 known NA subtypes (N1-N9). The 16 hemagglutinin subtypes are further classified into two phylogenetic groups: Group1 includes hemagglutinin H1, H2, H5, H6, H8, H9, H11, H12, H13, and H16 subtypes; Group2 includes hemagglutinin H3, H4, H7, H10, H14, and H15 subtypes.

Hemagglutinin promotes viral attachment and entry into the host cell; neuraminidase is required for viral budding from the infected cell. The hemagglutinin of influenza A virus comprises two structurally distinct regions—a globular head region and a stalk or stem region. The globular head region contains a receptor binding site which is responsible for virus attachment to a target cell. The stalk (or stem) region of hemagglutinin contains a fusion peptide which is necessary for membrane fusion between the viral envelope and an endosomal membrane of the infected cell. (See, e.g., Bouvier and Palese (2008) Vaccine 26 Suppl 4: D49-53; Wiley et al., (1987) Ann Rev Biochem 556:365-394.)

Current treatment for influenza virus infection includes neuraminidase inhibitors, such as oseltamivir and zanamivir. Oseltamivir is a widely used prophylactic and early therapeutic treatment option for influenza A virus infection. (See, e.g., Kandel and Hartshorn (2001) BioDrugs: Clinical Immunotherapy, Biopharmaceuticals and Gene Therapy 15:303-323; Nicholson et al., (2000) Lancet 355:1845-1850; Treanor et al., (2000) JAMA 283:1016-1024; and Welliver et al., (2001) JAMA 285:748-754.) However, oseltamivir treatment must begin within 48 hours of symptom onset to provide a significant clinical benefit. (See, e.g., Aoki et al (2003) J Antimicrobial Chemotherapy 51:123-129.) This liability compromises oseltamivir's ability to treat severely ill patients, who are typically beyond the optimal 48-hour treatment window at the time of seeking treatment. Therefore, significant focus has recently been placed on identifying influenza virus therapeutics to treat hospitalized influenza virus infected patients. One strategy has focused on development of human monoclonal antibodies (mAbs) that target a highly conserved epitope on the stalk of influenza A virus hemagglutinin. (See, e.g., Corti et al., (2011) Science 333:850-856; Ekiert et al., (2009) Science 324:246-251; Ekiert et al., (2011) Science 333:843-850; Sui et al., (2009) Nature Structural & Molecular Biology 16:265-273; Dreyfus et al., (2012) Science 337:1343-1348; Wu et al., (2012) J Virology 2012.09.034; Clementi et al., (2011) PLoS One 6:1-10. See also International Patent Application Publication Nos: WO2009/115972, WO2011/117848, WO2008/110937, WO2010/010466, WO2008/028946, WO2010/130636, WO2012/021786, WO2010/073647, WO2011/160083, WO2011/111966, WO2002/46235, and WO2009/053604; U.S. Pat. Nos. 5,631,350 and 5,589,174.)

Several reports have described monoclonal antibodies (mAb) that bind hemagglutinin and broadly neutralize influenza A virus. For example, Corti et al. (supra) described antibody FI6v3, which was cloned from a human plasma cell and shown to neutralize human influenza A viruses belonging to both Group1 and Group2 hemagglutinin subtypes. The FI6v3 mAb was discovered as a result of a heroic effort of analyzing approximately 104,000 human plasma cells. Additionally, Dreyfus et al. (supra) recently described the identification of antibody CR9114 by phage display panning; antibody CR9114 was shown to bind to a highly conserved stalk epitope shared between influenza A virus and influenza B virus hemagglutinin.

Despite these reports, a need still exists in the art for novel influenza A virus therapies effective against Group1 and Group2 influenza A virus subtypes. The present invention

SUMMARY OF THE INVENTION

The present invention provides anti-hemagglutinin antibodies, compositions comprising anti-hemagglutinin antibodies, and methods of using the same.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
 (a) HVR-H1 comprises the amino acid sequence of SEQ ID NO:178;
 (b) HVR-H2 comprises the amino acid sequence of SEQ ID NO:179;
 (c) HVR-H3 comprises an amino acid sequence selected from the group consisting of SEQ ID NOs:180 and 181;
 (d) HVR-L1 comprises an amino acid sequence selected from the group consisting of SEQ ID NOs:182, 183, 184, 185, and 186;
 (e) HVR-L2 comprises the amino acid sequence of SEQ ID NO:187; and
 (f) HVR-L3 comprises an amino acid sequence selected from the group consisting of SEQ ID NOs:188, 189, and 190.

In some embodiments, the invention provides an isolated anti-hemagglutinin antibody comprising: at least one, two, three, four, five and/or six hypervariable region (HVR) sequences, wherein:
 (a) HVR-H1 comprises the amino acid sequence of SEQ ID NO:178;
 (b) HVR-H2 comprises the amino acid sequence of SEQ ID NO:179;
 (c) HVR-H3 comprises an amino acid sequence selected from the group consisting of SEQ ID NOs:180 and 181;
 (d) HVR-L1 comprises an amino acid sequence selected from the group consisting of SEQ ID NOs:182, 183, 184, 185, and 186;
 (e) HVR-L2 comprises the amino acid sequence of SEQ ID NO:187; and
 (f) HVR-L3 comprises an amino acid sequence selected from the group consisting of SEQ ID NOs:188, 189, and 190.

In some embodiments, the invention provides an isolated anti-hemagglutinin antibody comprising three light chain hypervariable regions (HVR-L1, HVR-L2, and LVR-L3), wherein:
 (a) HVR-L1 comprises an amino acid sequence selected from the group consisting of SEQ ID NOs:182, 183, 184, 185, and 186;
 (b) HVR-L2 comprises the amino acid sequence of SEQ ID NO:187; and
 (c) HVR-L3 comprises an amino acid sequence selected from the group consisting of SEQ ID NOs:188, 189, and 190.

In some embodiments, the invention provides an isolated anti-hemagglutinin antibody comprising three heavy chain hypervariable regions (HVR-H1, HVR-H2, and HVR-H3), wherein:
 (a) HVR-H1 comprises the amino acid sequence of SEQ ID NO:178;
 (b) HVR-H2 comprises the amino acid sequence of SEQ ID NO:179; and
 (c) HVR-H3 comprises an amino acid sequence selected from the group consisting of SEQ ID NOs:180 and 181.

In some embodiments, the invention provides an isolated anti-hemagglutinin antibody comprising: at least one, two, and/or three light chain hypervariable region (HVR) sequences, wherein:
 (a) HVR-L1 comprises an amino acid sequence selected from the group consisting of SEQ ID NOs:182, 183, 184, 185, and 186;
 (b) HVR-L2 comprises the amino acid sequence of SEQ ID NO:187; and
 (c) HVR-L3 comprises an amino acid sequence selected from the group consisting of SEQ ID NOs:188, 189, and 190.

In some embodiments, the invention provides an isolated anti-hemagglutinin antibody comprising: at least one, two, and/or three heavy chain hypervariable region (HVR) sequences, wherein:
 (a) HVR-H1 comprises the amino acid sequence of SEQ ID NO:178;
 (b) HVR-H2 comprises the amino acid sequence of SEQ ID NO:179; and
 (c) HVR-H3 comprises an amino acid sequence selected from the group consisting of SEQ ID NOs:180 and 181.

In some embodiments, an isolated anti-hemagglutinin antibody of the present invention comprises a heavy chain variable region and a light chain variable region, wherein the heavy chain variable region comprises an amino acid sequence selected from the group consisting of SEQ ID NOs:111 and 115, and the light chain variable region comprises an amino acid sequence selected from the group consisting of SEQ ID NOs:113, 117, 119, 122, 124, 126, 128, 130, and 132.

In some embodiments, an isolated anti-hemagglutinin antibody of the present invention comprises a light chain variable region comprising an amino acid sequence selected from the group consisting of SEQ ID NOs:113, 117, 119, 122, 124, 126, 128, 130, and 132.

In some embodiments, an isolated anti-hemagglutinin antibody of the present invention comprises a heavy chain variable region comprises an amino acid sequence selected from the group consisting of SEQ ID NOs:111 and 115.

In some embodiments, an isolated anti-hemagglutinin antibody of the present invention comprises a heavy chain and a light chain, wherein the heavy chain comprises an amino acid sequence selected from the group consisting of SEQ ID NOs:110, 114, and 120, and the light chain comprises an amino acid sequence selected from the group consisting of SEQ ID NOs:112, 116, 118, 121, 123, 125, 127, 129, and 131.

In some embodiments, an isolated anti-hemagglutinin antibody of the present invention comprises a light chain comprising an amino acid sequence selected from the group consisting of SEQ ID NOs:112, 116, 118, 121, 123, 125, 127, 129, and 131.

In some embodiments, an isolated anti-hemagglutinin antibody of the present invention comprises a heavy chain comprising an amino acid sequence selected from the group consisting of SEQ ID NOs:110, 114, and 120.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
 (a) HVR-H1 comprises an amino acid sequence selected from the group consisting of SEQ ID NOs:191 and 192;
 (b) HVR-H2 comprises the amino acid sequence of SEQ ID NO:193;

(c) HVR-H3 comprises the amino acid sequence of SEQ ID NO:194;
(d) HVR-L1 comprises the amino acid sequence of SEQ ID NO:195;
(e) HVR-L2 comprises the amino acid sequence of SEQ ID NO:196; and
(f) HVR-L3 comprises an amino acid sequence selected from the group consisting of SEQ ID NOs:197, 198, and 199.

In some embodiments, the invention provides an isolated anti-hemagglutinin antibody comprising: at least one, two, three, four, five and/or six hypervariable region (HVR) sequences, wherein:
(a) HVR-H1 comprises an amino acid sequence selected from the group consisting of SEQ ID NOs:191 and 192;
(b) HVR-H2 comprises the amino acid sequence of SEQ ID NO:193;
(c) HVR-H3 comprises the amino acid sequence of SEQ ID NO:194;
(d) HVR-L1 comprises the amino acid sequence of SEQ ID NO:195;
(e) HVR-L2 comprises the amino acid sequence of SEQ ID NO:196; and
(f) HVR-L3 comprises an amino acid sequence selected from the group consisting of SEQ ID NOs:197, 198, and 199.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:195;
(b) HVR-L2 comprises the amino acid sequence of SEQ ID NO:196; and
(c) HVR-L3 comprises an amino acid sequence selected from the group consisting of SEQ ID NOs:197, 198, and 199.

In some embodiments, the invention provides an isolated anti-hemagglutinin antibody comprising three heavy chain hypervariable regions (HVR-H1, HVR-H2, and HVR-H3), wherein:
(a) HVR-H1 comprises an amino acid sequence selected from the group consisting of SEQ ID NOs:191 and 192;
(b) HVR-H2 comprises the amino acid sequence of SEQ ID NO:193; and
(c) HVR-H3 comprises the amino acid sequence of SEQ ID NO:194.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:195;
(b) HVR-L2 comprises the amino acid sequence of SEQ ID NO:196; and
(c) HVR-L3 comprises an amino acid sequence selected from the group consisting of SEQ ID NOs:197, 198, and 199.

In some embodiments, the invention provides an isolated anti-hemagglutinin antibody comprising: at least one, two, and/or three heavy chain hypervariable region (HVR) sequences, wherein:
(a) HVR-H1 comprises an amino acid sequence selected from the group consisting of SEQ ID NOs:191 and 192;
(b) HVR-H2 comprises the amino acid sequence of SEQ ID NO:193; and
(c) HVR-H3 comprises the amino acid sequence of SEQ ID NO:194.

In some embodiments, an isolated anti-hemagglutinin antibody of the present invention comprises a heavy chain variable region and a light chain variable region, wherein the heavy chain variable region comprises an amino acid sequence selected from the group consisting of SEQ ID NOs:134, 138, 142, 148, and 234, and the light chain variable region comprises an amino acid sequence selected from the group consisting of SEQ ID NOs:136, 140, 144, 146, 150, 152, and 235.

In some embodiments, an isolated anti-hemagglutinin antibody of the present invention comprises a light chain variable region comprising an amino acid sequence selected from the group consisting of SEQ ID NOs: 136, 140, 144, 146, 150, 152, and 235.

In some embodiments, an isolated anti-hemagglutinin antibody of the present invention comprises a heavy chain variable region comprises an amino acid sequence selected from the group consisting of SEQ ID NOs: 134, 138, 142, 148, and 234.

In some embodiments, an isolated anti-hemagglutinin antibody of the present invention comprises a heavy chain and a light chain, wherein the heavy chain comprises an amino acid sequence selected from the group consisting of SEQ ID NOs:133, 137, 141, and 147, and the light chain comprises an amino acid sequence selected from the group consisting of SEQ ID NOs:135, 139, 143, 145, 149, and 151.

In some embodiments, an isolated anti-hemagglutinin antibody of the present invention comprises a light chain comprising an amino acid sequence selected from the group consisting of SEQ ID NOs: 135, 139, 143, 145, 149, and 151.

In some embodiments, an isolated anti-hemagglutinin antibody of the present invention comprises a heavy chain comprising an amino acid sequence selected from the group consisting of SEQ ID NOs: 133, 137, 141, and 147.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:200;
(b) HVR-H2 comprises the amino acid sequence of SEQ ID NO:201;
(c) HVR-H3 comprises the amino acid sequence of SEQ ID NO:202;
(d) HVR-L1 comprises the amino acid sequence of SEQ ID NO:203;
(e) HVR-L2 comprises the amino acid sequence of SEQ ID NO:204; and
(f) HVR-L3 comprises the amino acid sequence of SEQ ID NO:205.

In some embodiments, the invention provides an isolated anti-hemagglutinin antibody comprising: at least one, two, three, four, five and/or six hypervariable region (HVR) sequences, wherein:
(a) HVR-H1 comprises the amino acid sequence of SEQ ID NO:200;
(b) HVR-H2 comprises the amino acid sequence of SEQ ID NO:201;
(c) HVR-H3 comprises the amino acid sequence of SEQ ID NO:202;
(d) HVR-L1 comprises the amino acid sequence of SEQ ID NO:203;

(e) HVR-L2 comprises the amino acid sequence of SEQ ID NO:204; and
(f) HVR-L3 comprises the amino acid sequence of SEQ ID NO:205.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:203;
(b) HVR-L2 comprises the amino acid sequence of SEQ ID NO:204; and
(c) HVR-L3 comprises the amino acid sequence of SEQ ID NO:205.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:200;
(b) HVR-H2 comprises the amino acid sequence of SEQ ID NO:201; and
(c) HVR-H3 comprises the amino acid sequence of SEQ ID NO:202.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:203;
(b) HVR-L2 comprises the amino acid sequence of SEQ ID NO:204; and
(c) HVR-L3 comprises the amino acid sequence of SEQ ID NO:205.

In some embodiments, the invention provides an isolated anti-hemagglutinin antibody comprising: at least one, two, and/or three heavy chain hypervariable region (HVR) sequences, wherein:
(a) HVR-H1 comprises the amino acid sequence of SEQ ID NO:200;
(b) HVR-H2 comprises the amino acid sequence of SEQ ID NO:201; and
(c) HVR-H3 comprises the amino acid sequence of SEQ ID NO:202.

In some embodiments, an isolated anti-hemagglutinin antibody of the present invention comprises a heavy chain variable region and a light chain variable region, wherein the heavy chain variable region comprises an amino acid sequence selected from the group consisting of SEQ ID NOs:154 and 158, and the light chain variable region comprises the amino acid sequence of SEQ ID NO:156.

In some embodiments, an isolated anti-hemagglutinin antibody of the present invention comprises a light chain variable region comprising the amino acid sequence of SEQ ID NO:156.

In some embodiments, an isolated anti-hemagglutinin antibody of the present invention comprises a heavy chain variable region comprises an amino acid sequence selected from the group consisting of SEQ ID NOs: 154 and 158.

In some embodiments, an isolated anti-hemagglutinin antibody of the present invention comprises a heavy chain and a light chain, wherein the heavy chain comprises an amino acid sequence selected from the group consisting of SEQ ID NOs:153 and 157, and the light chain comprises the amino acid sequence of SEQ ID NO:155.

In some embodiments, an isolated anti-hemagglutinin antibody of the present invention comprises a light chain comprising the amino acid sequence of SEQ ID NO:155.

In some embodiments, an isolated anti-hemagglutinin antibody of the present invention comprises a heavy chain comprising an amino acid sequence selected from the group consisting of SEQ ID NOs:153 and 157.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:206;
(b) HVR-H2 comprises the amino acid sequence of SEQ ID NO:207;
(c) HVR-H3 comprises the amino acid sequence of SEQ ID NO:208;
(d) HVR-L1 comprises the amino acid sequence of SEQ ID NO:209;
(e) HVR-L2 comprises the amino acid sequence of SEQ ID NO:210; and
(f) HVR-L3 comprises the amino acid sequence of SEQ ID NO:211.

In some embodiments, the invention provides an isolated anti-hemagglutinin antibody comprising: at least one, two, three, four, five and/or six hypervariable region (HVR) sequences, wherein:
(a) HVR-H1 comprises the amino acid sequence of SEQ ID NO:206;
(b) HVR-H2 comprises the amino acid sequence of SEQ ID NO:207;
(c) HVR-H3 comprises the amino acid sequence of SEQ ID NO:208;
(d) HVR-L1 comprises the amino acid sequence of SEQ ID NO:209;
(e) HVR-L2 comprises the amino acid sequence of SEQ ID NO:210; and
(f) HVR-L3 comprises the amino acid sequence of SEQ ID NO:211.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:209;
(b) HVR-L2 comprises the amino acid sequence of SEQ ID NO:210; and
(c) HVR-L3 comprises the amino acid sequence of SEQ ID NO:211.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:206;
(b) HVR-H2 comprises the amino acid sequence of SEQ ID NO:207; and
(c) HVR-H3 comprises the amino acid sequence of SEQ ID NO:208.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:209;

(b) HVR-L2 comprises the amino acid sequence of SEQ ID NO:210; and
(c) HVR-L3 comprises the amino acid sequence of SEQ ID NO:211.

In some embodiments, the invention provides an isolated anti-hemagglutinin antibody comprising: at least one, two, and/or three heavy chain hypervariable region (HVR) sequences, wherein:
(a) HVR-H1 comprises the amino acid sequence of SEQ ID NO:206;
(b) HVR-H2 comprises the amino acid sequence of SEQ ID NO:207; and
(c) HVR-H3 comprises the amino acid sequence of SEQ ID NO:208.

In some embodiments, an isolated anti-hemagglutinin antibody of the present invention comprises a heavy chain variable region and a light chain variable region, wherein the heavy chain variable region comprises the amino acid sequence of SEQ ID NO:160, and the light chain variable region comprises the amino acid sequence of SEQ ID NO:162.

In some embodiments, an isolated anti-hemagglutinin antibody of the present invention comprises a light chain variable region comprising the amino acid sequence of SEQ ID NO:162.

In some embodiments, an isolated anti-hemagglutinin antibody of the present invention comprises a heavy chain variable region comprises the amino acid sequence of SEQ ID NO: 160.

In some embodiments, an isolated anti-hemagglutinin antibody of the present invention comprises a heavy chain and a light chain, wherein the heavy chain comprises the amino acid sequence of SEQ ID NO:159, and the light chain comprises the amino acid sequence of SEQ ID NO:161.

In some embodiments, an isolated anti-hemagglutinin antibody of the present invention comprises a light chain comprising the amino acid sequence of SEQ ID NO:161.

In some embodiments, an isolated anti-hemagglutinin antibody of the present invention comprises a heavy chain comprising the amino acid sequence of SEQ ID NO:159.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
(a) HVR-H1 comprises the amino acid sequence of SEQ ID NO:212;
(b) HVR-H2 comprises the amino acid sequence of SEQ ID NO:213;
(c) HVR-H3 comprises the amino acid sequence of SEQ ID NO:214;
(d) HVR-L1 comprises the amino acid sequence of SEQ ID NO:215;
(e) HVR-L2 comprises the amino acid sequence of SEQ ID NO:216; and
(f) HVR-L3 comprises the amino acid sequence of SEQ ID NO:217.

In some embodiments, the invention provides an isolated anti-hemagglutinin antibody comprising: at least one, two, three, four, five and/or six hypervariable region (HVR) sequences, wherein:
(a) HVR-H1 comprises the amino acid sequence of SEQ ID NO:212;
(b) HVR-H2 comprises the amino acid sequence of SEQ ID NO:213;
(c) HVR-H3 comprises the amino acid sequence of SEQ ID NO:214;
(d) HVR-L1 comprises the amino acid sequence of SEQ ID NO:215;
(e) HVR-L2 comprises the amino acid sequence of SEQ ID NO:216; and
(f) HVR-L3 comprises the amino acid sequence of SEQ ID NO:217.

In some embodiments, the invention provides an isolated anti-hemagglutinin antibody comprising three light chain hypervariable regions (HVR-L1, HVR-L2, and LVR-L3), wherein:
(a) HVR-L1 comprises the amino acid sequence of SEQ ID NO:215;
(b) HVR-L2 comprises the amino acid sequence of SEQ ID NO:216; and
(c) HVR-L3 comprises the amino acid sequence of SEQ ID NO:217.

In some embodiments, the invention provides an isolated anti-hemagglutinin antibody comprising three heavy chain hypervariable regions (HVR-H1, HVR-H2, and HVR-H3), wherein:
(a) HVR-H1 comprises the amino acid sequence of SEQ ID NO:212;
(b) HVR-H2 comprises the amino acid sequence of SEQ ID NO:213; and
(c) HVR-H3 comprises the amino acid sequence of SEQ ID NO:214.

In some embodiments, the invention provides an isolated anti-hemagglutinin antibody comprising: at least one, two, and/or three light chain hypervariable region (HVR) sequences, wherein:
(a) HVR-L1 comprises the amino acid sequence of SEQ ID NO:215;
(b) HVR-L2 comprises the amino acid sequence of SEQ ID NO:216; and
(c) HVR-L3 comprises the amino acid sequence of SEQ ID NO:217.

In some embodiments, the invention provides an isolated anti-hemagglutinin antibody comprising: at least one, two, and/or three heavy chain hypervariable region (HVR) sequences, wherein:
(a) HVR-H1 comprises the amino acid sequence of SEQ ID NO:212;
(b) HVR-H2 comprises the amino acid sequence of SEQ ID NO:213; and
(c) HVR-H3 comprises the amino acid sequence of SEQ ID NO:214.

In some embodiments, an isolated anti-hemagglutinin antibody of the present invention comprises a heavy chain variable region and a light chain variable region, wherein the heavy chain variable region comprises the amino acid sequence of SEQ ID NO:164, and the light chain variable region comprises the amino acid sequence of SEQ ID NO:166.

In some embodiments, an isolated anti-hemagglutinin antibody of the present invention comprises a light chain variable region comprising the amino acid sequence of SEQ ID NO:166.

In some embodiments, an isolated anti-hemagglutinin antibody of the present invention comprises a heavy chain variable region comprises the amino acid sequence of SEQ ID NO: 164.

In some embodiments, an isolated anti-hemagglutinin antibody of the present invention comprises a heavy chain and a light chain, wherein the heavy chain comprises the amino acid sequence of SEQ ID NO:163, and the light chain comprises the amino acid sequence of SEQ ID NO:165.

In some embodiments, an isolated anti-hemagglutinin antibody of the present invention comprises a light chain comprising the amino acid sequence of SEQ ID NO:165.

In some embodiments, an isolated anti-hemagglutinin antibody of the present invention comprises a heavy chain comprising the amino acid sequence of SEQ ID NO:163.

In some embodiments, an isolated anti-hemagglutinin antibody of the present invention comprises three heavy chain hypervariable regions (HVR-H1, HVR-H2, and HVR-H3) and three light chain hypervariable regions (HVR-L1, HVR-L2, and HVR-L3), wherein:
  (a) HVR-H1 comprises the amino acid sequence of SEQ ID NO:218;
  (b) HVR-H2 comprises the amino acid sequence of SEQ ID NO:219;
  (c) HVR-H3 comprises the amino acid sequence of SEQ ID NO:220;
  (d) HVR-L1 comprises the amino acid sequence of SEQ ID NO:221;
  (e) HVR-L2 comprises the amino acid sequence of SEQ ID NO:222; and
  (f) HVR-L3 comprises the amino acid sequence of SEQ ID NO:223.

In some embodiments, the invention provides an isolated anti-hemagglutinin antibody comprising: at least one, two, three, four, five and/or six hypervariable region (HVR) sequences, wherein:
  (a) HVR-H1 comprises the amino acid sequence of SEQ ID NO:218;
  (b) HVR-H2 comprises the amino acid sequence of SEQ ID NO:219;
  (c) HVR-H3 comprises the amino acid sequence of SEQ ID NO:220;
  (d) HVR-L1 comprises the amino acid sequence of SEQ ID NO:221;
  (e) HVR-L2 comprises the amino acid sequence of SEQ ID NO:222; and
  (f) HVR-L3 comprises the amino acid sequence of SEQ ID NO:223.

In some embodiments, the invention provides an isolated anti-hemagglutinin antibody comprising three light chain hypervariable regions (HVR-L1, HVR-L2, and LVR-L3), wherein:
  (a) HVR-L1 comprises the amino acid sequence of SEQ ID NO:221;
  (b) HVR-L2 comprises the amino acid sequence of SEQ ID NO:222; and
  (c) HVR-L3 comprises the amino acid sequence of SEQ ID NO:223.

In some embodiments, the invention provides an isolated anti-hemagglutinin antibody comprising three heavy chain hypervariable regions (HVR-H1, HVR-H2, and HVR-H3), wherein:
  (a) HVR-H1 comprises the amino acid sequence of SEQ ID NO:218;
  (b) HVR-H2 comprises the amino acid sequence of SEQ ID NO:219; and
  (c) HVR-H3 comprises the amino acid sequence of SEQ ID NO:220.

In some embodiments, the invention provides an isolated anti-hemagglutinin antibody comprising: at least one, two, and/or three light chain hypervariable region (HVR) sequences, wherein:
  (a) HVR-L1 comprises the amino acid sequence of SEQ ID NO:221;
  (b) HVR-L2 comprises the amino acid sequence of SEQ ID NO:222; and
  (c) HVR-L3 comprises the amino acid sequence of SEQ ID NO:223.

In some embodiments, the invention provides an isolated anti-hemagglutinin antibody comprising: at least one, two, and/or three heavy chain hypervariable region (HVR) sequences, wherein:
  (a) HVR-H1 comprises the amino acid sequence of SEQ ID NO:218;
  (b) HVR-H2 comprises the amino acid sequence of SEQ ID NO:219; and
  (c) HVR-H3 comprises the amino acid sequence of SEQ ID NO:220.

In some embodiments, an isolated anti-hemagglutinin antibody of the present invention comprises a heavy chain variable region and a light chain variable region, wherein the heavy chain variable region comprises the amino acid sequence of SEQ ID NO:168, and the light chain variable region comprises the amino acid sequence of SEQ ID NO:170.

In some embodiments, an isolated anti-hemagglutinin antibody of the present invention comprises a light chain variable region comprising the amino acid sequence of SEQ ID NO:170.

In some embodiments, an isolated anti-hemagglutinin antibody of the present invention comprises a heavy chain variable region comprises the amino acid sequence of SEQ ID NO: 168.

In some embodiments, an isolated anti-hemagglutinin antibody of the present invention comprises a heavy chain and a light chain, wherein the heavy chain comprises the amino acid sequence of SEQ ID NO:167, and the light chain comprises the amino acid sequence of SEQ ID NO:169.

In some embodiments, an isolated anti-hemagglutinin antibody of the present invention comprises a light chain comprising the amino acid sequence of SEQ ID NO:169.

In some embodiments, an isolated anti-hemagglutinin antibody of the present invention comprises a heavy chain comprising the amino acid sequence of SEQ ID NO:167.

The invention also provides isolated nucleic acids encoding an anti-hemagglutinin antibody of the present invention. The invention also provides vectors comprising a nucleic acid encoding an anti-hemagglutinin antibody of the present invention. The invention also provides host cells comprising a nucleic acid or a vector of the present invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example, a mammalian cell, such as a Chinese Hamster Ovary (CHO) cell.

The invention further provides a method of producing an anti-hemagglutinin antibody of the present invention. For example, the invention provides methods for making an anti-hemagglutinin antibody (which, as defined herein, includes full length antibody and fragments thereof), the method comprising expressing in a suitable host cell a recombinant vector of the invention encoding the anti-hemagglutinin antibody or fragments thereof so that the antibody or fragments thereof are produced. In some embodiments, the method comprises culturing a host cell comprising nucleic acid encoding an anti-hemagglutinin antibody of the present invention (or fragments thereof) so that the nucleic acid is expressed. The method may further comprise recovering the anti-hemagglutinin antibody or fragments thereof from the host cell culture or the host cell culture medium.

The invention also provides a pharmaceutical formulation comprising an anti-hemagglutinin antibody of the present invention and a pharmaceutically acceptable carrier. The pharmaceutical formulation may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides compositions comprising an anti-hemagglutinin antibody of the present invention. The composition may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides a composition comprising an anti-hemagglutinin antibody of the present invention for use in preventing influenza A virus infection. In some embodiments, the invention provides a pharmaceutical composition comprising an anti-hemagglutinin antibody of the present invention for use in preventing influenza A virus infection. The invention further provides a composition comprising an anti-hemagglutinin antibody of the present invention for use in treating influenza A virus infection. In some embodiments, the invention provides a pharmaceutical composition comprising an anti-hemagglutinin antibody of the present invention for use in treating influenza A virus infection. The invention further provides a composition comprising an anti-hemagglutinin antibody of the present invention for use in inhibiting influenza A virus infection. In some embodiments, the invention provides a pharmaceutical composition comprising an anti-hemagglutinin antibody of the present invention for use in inhibiting influenza A virus infection.

Compositions comprising an anti-hemagglutinin antibody of the present invention may also be used in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

The invention also provides a method for inhibiting influenza A virus infection, the method comprising administering to a patient in need thereof an effective amount of a composition comprising an anti-hemagglutinin antibody of the present invention, thereby inhibiting influenza A virus infection. The invention also provides a method for treating influenza A virus infection, the method comprising administering to a patient in need thereof an effective amount of a composition comprising an anti-hemagglutinin antibody of the present invention, thereby treating influenza A virus infection. The invention also provides a method for preventing influenza A virus infection, the method comprising administering to a patient in need thereof an effective amount of a composition comprising an anti-hemagglutinin antibody of the present invention, thereby preventing influenza A virus infection.

The invention also provides a method for inhibiting, treating, or preventing influenza A virus infection, the method comprising administering to a patient in need thereof an effective amount of a composition comprising an anti-hemagglutinin antibody of the present invention, and administering to the patient an effective amount of an additional therapeutic agent, thereby inhibiting, treating, or preventing influenza A virus infection. In some embodiments, the additional therapeutic agent is a neuraminidase inhibitor, such as oseltamivir or zanamivir. In other embodiments, the additional therapeutic agent is another anti-hemagglutinin antibody. In yet other embodiments, the additional therapeutic agent is an anti-M2 antibody. In various aspects of such combination treatments, the therapeutic agents are administered at about the same time, are administered together, or are administered sequentially or consecutively. In particular embodiments, an anti-neuraminidase inhibitor is administered prior to the administration of an anti-hemagglutinin antibody of the present invention.

In another aspect, the invention provides use of an anti-hemagglutinin antibody of the present invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a nucleic acid of the invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of an expression vector of the invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a host cell of the invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of an article of manufacture of the invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In another aspect, the invention provides use of a kit of the invention in the manufacture of a medicament. The medicament may be for use in the inhibition, treatment, or prevention of influenza A virus infection. In certain embodiments, the medicament may further comprise an additional therapeutic agent (e.g., a neuraminidase inhibitor, such as oseltamivir or zanamivir; another antibody, such as another anti-hemagglutinin antibody or an anti-M2 antibody; etc).

In various aspects, an anti-hemagglutinin antibody of the present invention binds hemagglutinin. In some aspects, an anti-hemagglutinin antibody of the present invention binds Group1 hemagglutinin, binds Group2 hemagglutinin, or binds Group1 and Group2 hemagglutinin. In other aspects, an anti-hemagglutinin antibody of the present invention binds hemagglutinin and neutralizes influenza A virus. In some embodiments, an anti-hemagglutinin antibody of the present invention neutralizes influenza A virus in vitro, in vivo, or in vitro and in vivo.

BRIEF DESCRIPTION OF THE FIGURES

FIG. 3 sets for data showing in vitro neutralization of various influenza A Group1 and Group2 virus strains by anti-hemagglutinin antibodies of the present invention.

FIG. 20 shows an amino acid sequence alignment of hemagglutinin amino acid sequences from hemagglutinin H1, H2, H3, H5 and H7, showing hemagglutinin contact residues (shaded) of monoclonal antibody 39.29NCv1 and the hemagglutinin binding epitope.

FIGS. 22A and 22B show an amino acid sequence alignment of the light chain variable region and the heavy chain variable region of monoclonal antibody 81.39 B1C1 (SEQ ID NOs:113 and 111, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 23A and 23B show an amino acid sequence alignment of the light chain variable region and the heavy chain variable region of monoclonal antibody 81.39 SVSH-NYP ("SVSH" disclosed as SEQ ID NO: 171) (SEQ ID NOs:117 and 115, respectively) with immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 24A and 24B show an amino acid sequence alignment of the light chain variable region and the heavy chain variable region of monoclonal antibody 81.39 B1F1 (SEQ ID NOs:119 and 111, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 25A and 25B show an amino acid sequence alignment of the light chain variable region and the heavy chain variable region of monoclonal antibody 81.39 SVDS ("SVDS" disclosed as SEQ ID NO: 172) (SEQ ID NOs:113 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 26A and 26B show an amino acid sequence alignment of the light chain variable region and the heavy chain variable region of monoclonal antibody 81.39 SVSS ("SVSS" disclosed as SEQ ID NO: 173) (SEQ ID NOs:122 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

Figure 27B:
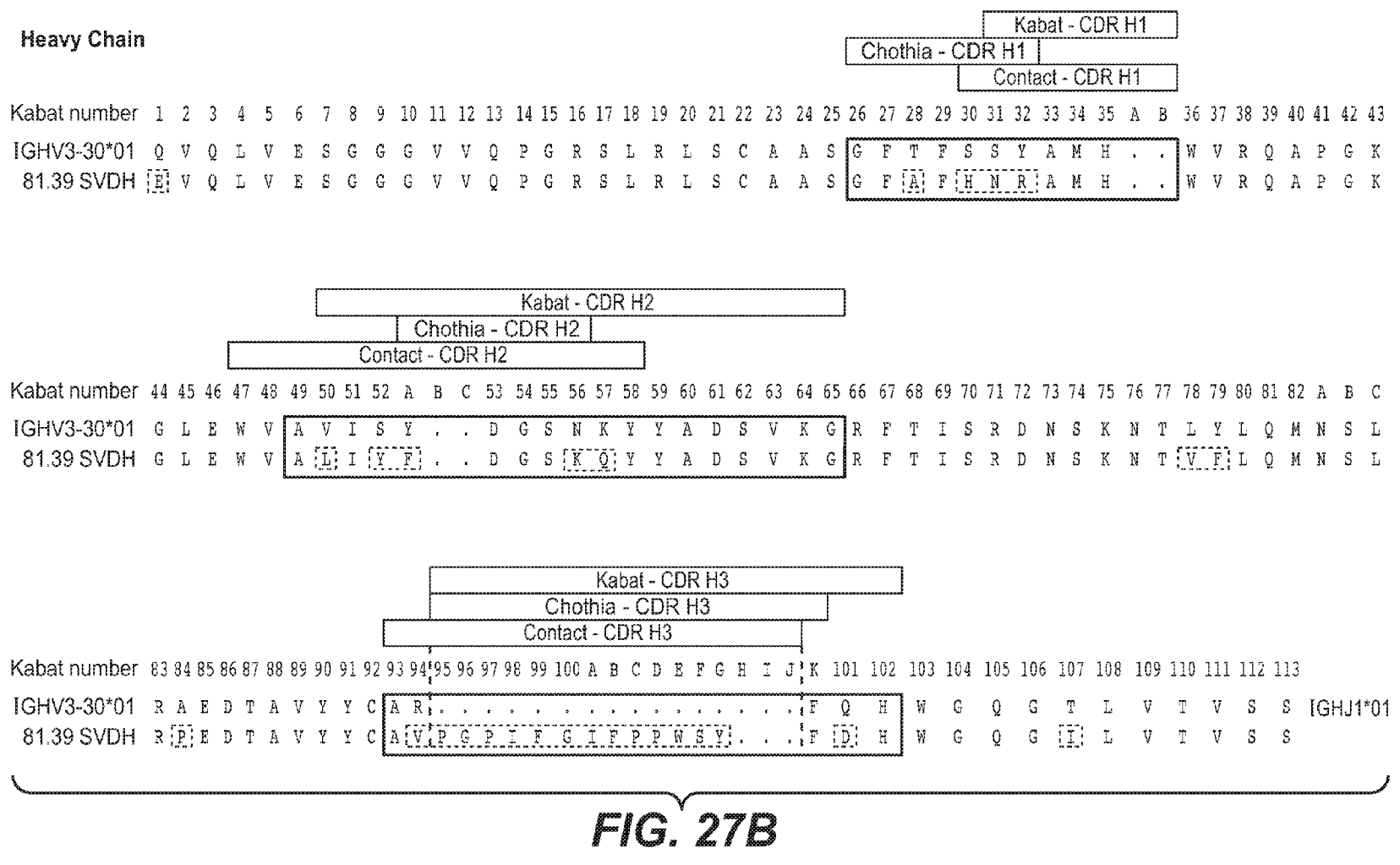

FIGS. 27A and 27B show an amino acid sequence alignment of the light chain variable region and the heavy chain variable region of monoclonal antibody 81.39 SVDH ("SVDH" disclosed as SEQ ID NO: 174) (SEQ ID NOs:124 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

Figure 28B:
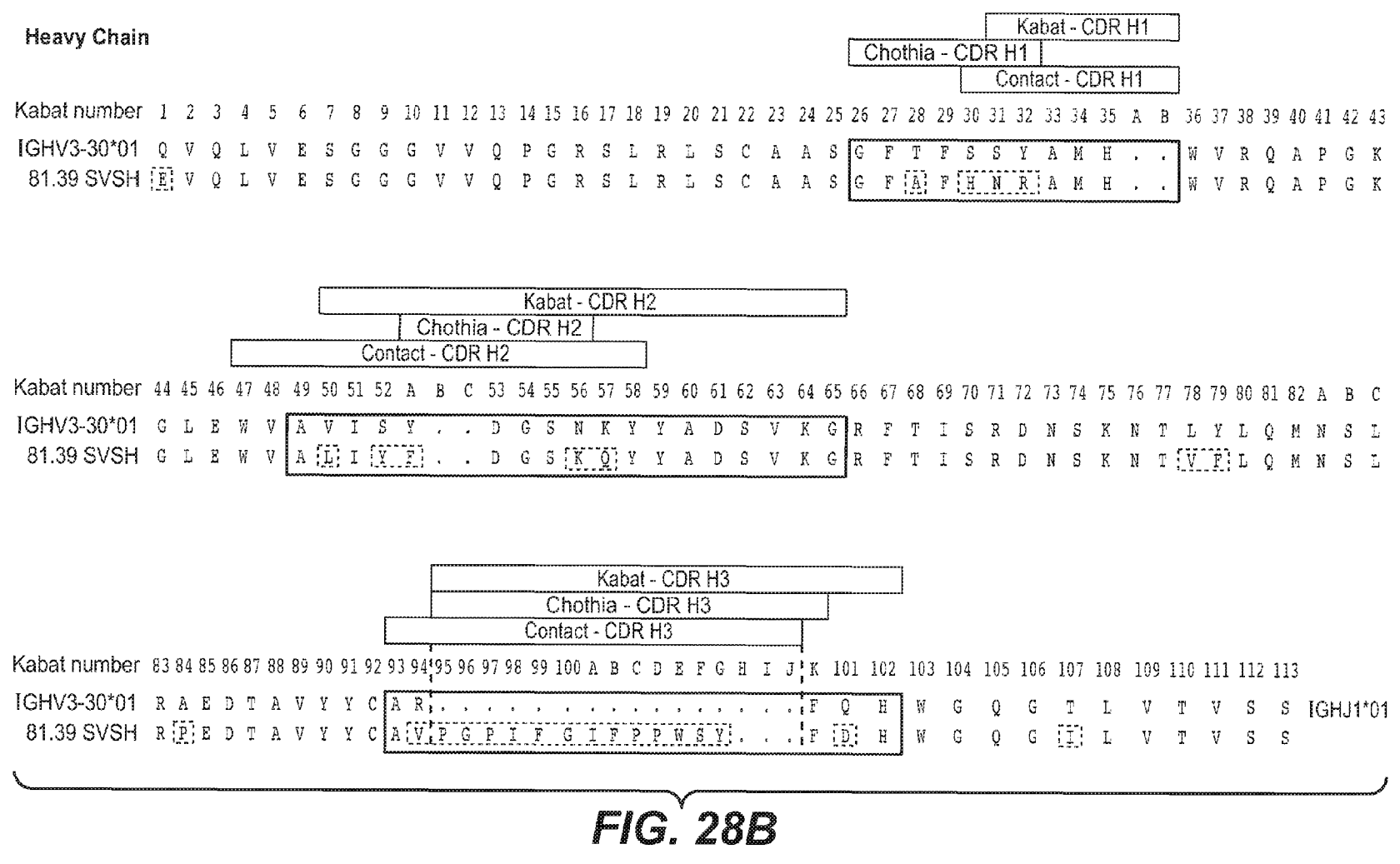

FIGS. 28A and 28B show an amino acid sequence alignment of the light chain variable region and the heavy chain variable region of mAb 81.39 SVSH ("SVSH" disclosed as SEQ ID NO: 171) (SEQ ID NOs:126 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 29A and 29B show an amino acid sequence alignment of the light chain variable region and the heavy chain variable region of monoclonal antibody 81.39 SVSH.NFP ("SVSH" disclosed as SEQ ID NO: 171) (SEQ ID NOs:128 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 30A and 30B show an amino acid sequence alignment of the light chain variable region and the heavy chain variable region of monoclonal antibody 81.39 SVDS.F ("SVDS" disclosed as SEQ ID NO: 172) (SEQ ID NOs:130 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 31A and 31B show an amino acid sequence alignment of the light chain variable region and the heavy chain variable region of monoclonal antibody 81.39 SVDS.Y ("SVDS" disclosed as SEQ ID NO: 172) (SEQ ID NOs:132 and 115, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 237, respectively). The amino acids are numbers according to Kabat numbering. The Kabat, Chothia, and Contact CDRs are indicated.

FIGS. 32A and 32B show an amino acid sequence alignment of the light chain variable region and the heavy chain variable region of monoclonal antibody 39.29 D2C4 (SEQ ID NOs:136 and 134, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 33A and 33B show an amino acid sequence alignment of the light chain variable region and the heavy chain variable region of monoclonal antibody 39.29 D8C2 (SEQ ID NOs:140 and 138, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

Figure 34B:
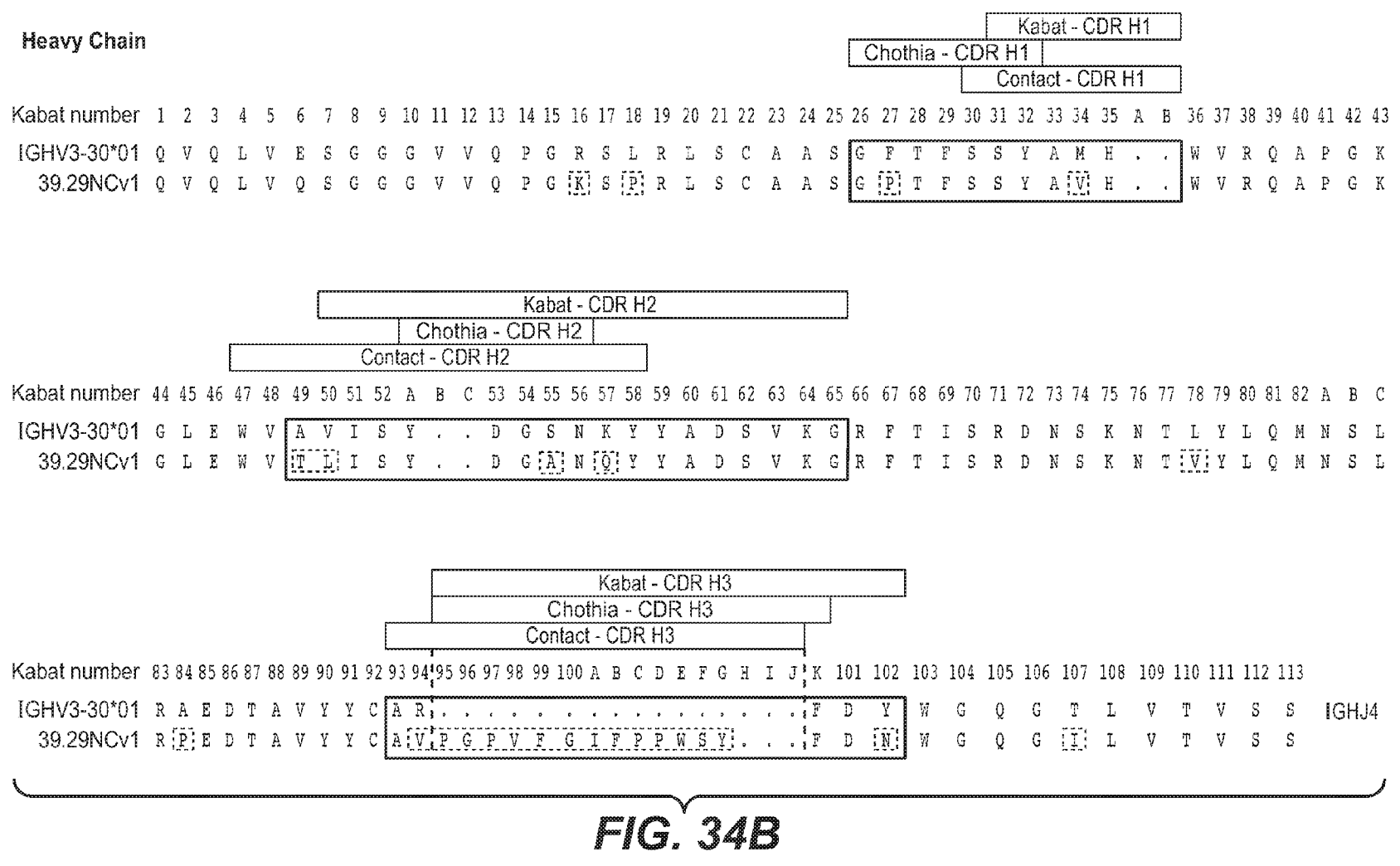

FIGS. 34A and 34B show an amino acid sequence alignment of the light chain variable region and the heavy chain variable region of monoclonal antibody 39.29 NCv1 (SEQ ID NOs:144 and 142, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 35A and 35B show an amino acid sequence alignment of the light chain variable region and the heavy chain variable region of monoclonal antibody 39.29 D8E7 (SEQ ID NOs:146 and 138, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 36A and 36B show an amino acid sequence alignment of the light chain variable region and the heavy chain variable region of monoclonal antibody 39.29 NFPP ("NFPP" disclosed as SEQ ID NO: 175) (SEQ ID NOs:150 and 148, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 37A and 37B show an amino acid sequence alignment of the light chain variable region and the heavy chain variable region of monoclonal antibody 39.29 NYPP ("NYPP" disclosed as SEQ ID NO: 176) (SEQ ID NOs:152 and 148, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 38A and 38B show an amino acid sequence alignment of the light chain variable region and the heavy chain variable region of monoclonal antibody 39.29 NWPP ("NWPP" disclosed as SEQ ID NO: 177) (SEQ ID NOs:235 and 234, respectively) with the immunoglobulin kappa variable 3-15*01 germ-line (IGKV3-15*01) and the immunoglobulin heavy chain variable 3-30*01 germ-line (IGHV3-30*01) (SEQ ID NOs:236 and 245, respectively). The amino acids are numbers according to Kabat numbering. The Kabat, Chothia, and Contact CDRs are indicated.

FIGS. 39A and 39B show an amino acid sequence alignment of the light chain variable region and the heavy chain variable region of monoclonal antibody 39.18 B11 (SEQ ID NOs:156 and 154, respectively) with the immunoglobulin kappa variable 3-15*01 germ-line (IGKV3-15*01) and the immunoglobulin heavy chain variable 1-69*01 germ-line (IGHV1-69*01) (SEQ ID NOs:236 and 238, respectively). The amino acids are numbers according to Kabat numbering. The Kabat, Chothia, and Contact CDRs are indicated.

FIGS. 40A and 40B show an amino acid sequence alignment of the light chain variable region and the heavy chain variable region of monoclonal antibody 39.18 E12 (SEQ ID NOs:156 and 158, respectively) with the immunoglobulin kappa variable 3-15*01 germ-line (IGKV3-15*01) and the immunoglobulin heavy chain variable 1-69*01 germ-line (IGHV1-69*01) (SEQ ID NOs:236 and 238, respectively). The amino acids are numbers according to Kabat numbering. The Kabat, Chothia, and Contact CDRs are indicated.

FIGS. 41A and 41B show an amino acid sequence alignment of the light chain variable region and the heavy chain variable region of monoclonal antibody 36.89 (SEQ ID NOs:162 and 160, respectively) with the immunoglobulin kappa variable 1-5*03 germ-line (IGKV1-5*03) and the immunoglobulin heavy chain variable 1-18*01 germ-line (IGHV1-18*01) (SEQ ID NOs:239 and 240, respectively). The amino acids are numbers according to Kabat numbering. The Kabat, Chothia, and Contact CDRs are indicated.

FIGS. 42A and 42B show an amino acid sequence alignment of the light chain variable region and the heavy chain variable region of monoclonal antibody 9.01F3 (SEQ ID NOs:166 and 164, respectively) with the immunoglobulin light variable 1-44*01 germ-line (IGKV1-44*01) and the immunoglobulin heavy chain variable 1-2*02*01 germ-line (IGHV1-2*02) (SEQ ID NOs:241 and 242, respectively). The amino acids are numbers according to Kabat numbering. The Kabat, Chothia, and Contact CDRs are indicated.

Figure 43A:
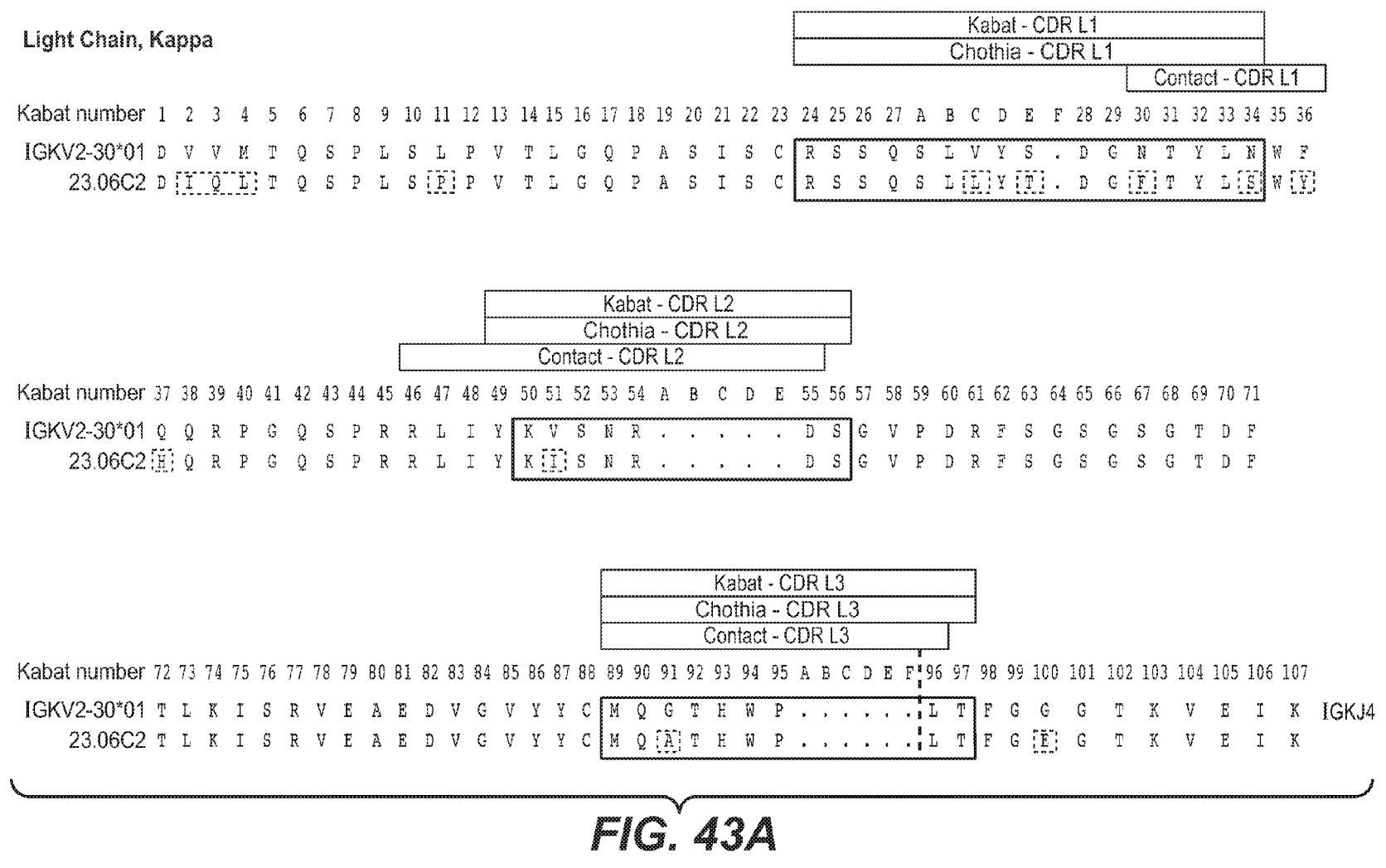

FIGS. 43A and 43B show an amino acid sequence alignment of the light chain variable region and the heavy chain variable region of monoclonal antibody 23.06C2 (SEQ ID NOs:170 and 168, respectively) with the immunoglobulin kappa variable 2-30*01 germ-line (IGKV2-30*01) and the immunoglobulin heavy chain variable 4-39*01 germ-line (IGHV4-39*01) (SEQ ID NOs:243 and 244, respectively). The amino acids are numbers according to Kabat numbering. The Kabat, Chothia, and Contact CDRs are indicated.

DETAILED DESCRIPTION OF EMBODIMENTS OF THE INVENTION

I. Definitions

Figure 1A:
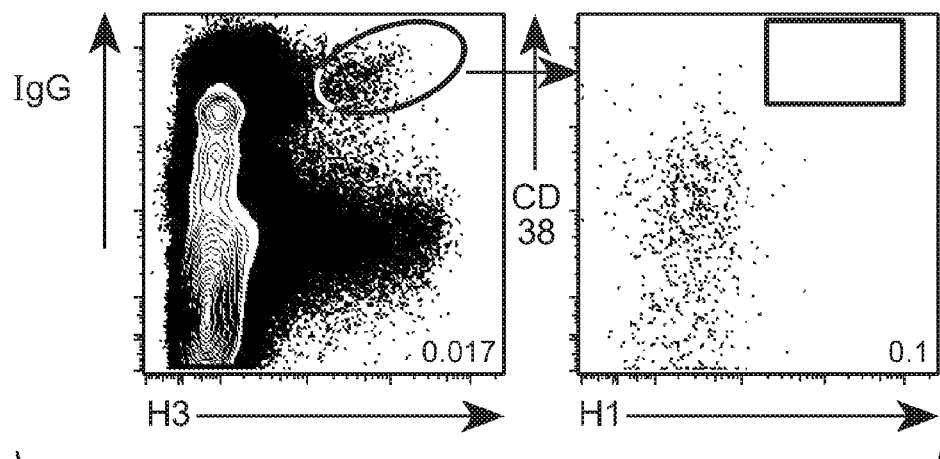
FIGS. 1A and 1B sets forth data showing FACS analysis of anti-hemagglutinin-positive (hemagglutinin H3+ and hemagglutinin H1+) plasmablasts from day 7 post-vaccinated human peripheral blood mononuclear cells (PBMCs) prior to SCID/beige mouse enrichment (FIG. 1A) and day 8 post-intrasplenic implantation after SCID/beige mouse enrichment with and without antigen premix (FIG. 1B) in the upper and lower panels, respectively.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-hemagglutinin antibody" and "an antibody that binds to hemagglutinin" refer to an antibody that binds hemagglutinin with sufficient affinity such that the antibody is useful as a diagnostic and/or therapeutic agent in targeting hemagglutinin, including targeting hemagglutinin of influenza virus. In one embodiment, the extent of binding of an anti-hemagglutinin antibody to an unrelated, non-hemagglutinin protein is less than about 10% of the binding of the antibody to hemagglutinin as measured, e.g., by a radioimmunoassay (MA). In certain embodiments, an antibody that binds to hemagglutinin has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$ M, e.g., from $10^{-9}$M to $10^{-13}$ M). In certain embodiments, an anti-hemagglutinin antibody binds to an epitope of hemagglutinin that is conserved among hemagglutinin from different strains, subtypes, and isolates of influenza A viruses.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. An antibody fragment also refers to a molecule other than an intact antibody that comprises a portion of an intact antibody that binds hemagglutinin and neutralizes influenza A virus. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-hemagglutinin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "hemagglutinin," as used herein, refers to any native hemagglutinin from any influenza virus source, unless otherwise indicated. The term encompasses "full-length," unprocessed hemagglutinin as well as any form of hemagglutinin that results from processing in an influenza virus or an influenza virus-infected cell. The term also encompasses naturally occurring variants of hemagglutinin, e.g., splice variants or allelic variants. The amino acid sequences of exemplary hemagglutinin proteins from various influenza A virus strains are shown in SEQ ID NOs:225 (H2 from A/Japan/305/1957), 226 (H3 from A/Perth/16/2009), 227 (H5 from A/Vietnam/1203/2004), 228 (H7 from A/chicken/NSW/1/1997), 229 (H1 from A/California/07/2009), 230 (H1 from A/NSW/1933), 231 (H3 from A/Hong Kong/8/1968), 232 (H7 from A/Netherlands/219/2003), and 233 (A/South Carolina/1918).

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease (e.g., preventing occurrence or recurrence of influenza A virus infection), reduction (e.g., reducing) or alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on anti-hemagglutinin antibodies and uses thereof. In certain embodiments, antibodies that bind to hemagglutinin are provided. Antibodies of the invention are useful, e.g., for the diagnosis, treatment, or prevention of influenza A virus infection.

A. Exemplary Anti-Hemagglutinin Antibodies

In one aspect, the invention provides isolated antibodies that bind to hemagglutinin. In certain embodiments, an anti-hemagglutinin antibody of the present invention binds hemagglutinin, binds Group1 hemagglutinins, binds Group2 hemagglutinins, or binds Group1 and Group2 hemagglutinins. In other embodiments, an anti-hemagglutinin antibody of the present invention neutralizes influenza A virus in vitro. In other embodiments, an anti-hemagglutinin antibody of the present invention neutralizes influenza A virus in vivo. In yet other embodiments, an anti-hemagglutinin antibody of the present invention reduces influenza A virus infection, prevents influenza A virus infection, inhibits influenza A virus infection, or treats influenza A virus infection. In some embodiments, an anti-hemagglutinin antibody of the present invention prevents, inhibits, or reduces hemagglutinin-mediated fusion between influenza virus membrane and infected cell endosomal membranes (thus preventing, inhibiting, or reducing viral RNA entry into the infected cell cytoplasm, thus preventing, inhibiting, or reducing further propagation of influenza virus infection.)

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:180; (d) HVR-L1 comprising the amino acid sequence of SEQ ID NO:182; (e) HVR-L2 comprising the amino acid sequence of SEQ ID NO:187; and (f) HVR-L3 comprising the amino acid sequence of SEQ ID NO:188.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising the amino acid sequence of SEQ ID NO:189.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:182; (e) HVR-L2 comprising the amino acid sequence of SEQ ID NO:187; and (f) HVR-L3 comprising the amino acid sequence of SEQ ID NO:188.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:184; (e) HVR-L2 comprising the amino acid sequence of SEQ ID NO:187; and (f) HVR-L3 comprising the amino acid sequence of SEQ ID NO:188.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:185; (e) HVR-L2 comprising the amino acid sequence of SEQ ID NO:187; and (f) HVR-L3 comprising the amino acid sequence of SEQ ID NO:188.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising the amino acid sequence of SEQ ID NO:188.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising the amino acid sequence of SEQ ID NO:190.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:182; (e) HVR-L2 comprising the amino acid sequence of SEQ ID NO:187; and (f) HVR-L3 comprising the amino acid sequence of SEQ ID NO:190.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:186; (e) HVR-L2 comprising the amino acid sequence of SEQ ID NO:187; and (f) HVR-L3 comprising the amino acid sequence of SEQ ID NO:189.

In one aspect, the invention provides an anti-hemagglutinin antibody comprising at least one, two, three, four, five, or six HVRs selected from (a) HVR-H1 comprising the amino acid sequence of SEQ ID NO:178; (b) HVR-H2 comprising the amino acid sequence of SEQ ID NO:179; (c) HVR-H3 comprising an amino acid sequence selected from the group consisting of SEQ ID NOs:180 and 181; (d) HVR-L1 comprising an amino acid sequence selected from the group consisting of SEQ ID NOs:182, 183, 184, 185, and 186; (e) HVR-L2 comprising the amino acid sequence of SEQ ID NO:187; and (f) HVR-L3 comprising an amino acid sequence selected from the group consisting of SEQ ID NOs:188, 189, and 190.

In one aspect, the invention provides an antibody comprising at least one, at least two, or all three VH HVR sequences selected from (a) HVR-H1 comprising the amino acid sequence of SEQ ID NO:178; (b) HVR-H2 comprising the amino acid sequence of SEQ ID NO:179; and (c) HVR-H3 comprising an amino acid sequence selected from the group consisting of SEQ ID NOs:180 and 181.

In another aspect, the invention provides an antibody comprising at least one, at least two, or all three VL HVR sequences selected from (a) HVR-L1 comprising an amino acid sequence selected from the group consisting of SEQ ID NOs:182, 183, 184, 185, and 186; (b) HVR-L2 comprising the amino acid sequence of SEQ ID NO:187; and (c) HVR-L3 comprising an amino acid sequence selected from the group consisting of SEQ ID NOs:188, 189, and 190.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:180; (d) HVR-L1 comprising the amino acid sequence of SEQ ID NO:182; (e) HVR-L2 comprising the amino acid sequence of SEQ ID NO:187; and (f) HVR-L3 comprising an amino acid sequence selected from SEQ ID NO:188.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising an amino acid sequence selected from SEQ ID NO:189.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:182; (e) HVR-L2 comprising the amino acid sequence of SEQ ID NO:187; and (f) HVR-L3 comprising an amino acid sequence selected from SEQ ID NO:188.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:184; (e) HVR-L2 comprising the amino acid sequence of SEQ ID NO:187; and (f) HVR-L3 comprising an amino acid sequence selected from SEQ ID NO:188.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:185; (e) HVR-L2 comprising the amino acid sequence of SEQ ID NO:187; and (f) HVR-L3 comprising an amino acid sequence selected from SEQ ID NO:188.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising an amino acid sequence selected from SEQ ID NO:188.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:183; (e) HVR-L2 comprising the amino acid sequence of SEQ ID NO:187; and (f) HVR-L3 comprising an amino acid sequence selected from SEQ ID NO:190.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:182; (e) HVR-L2 comprising the amino acid sequence of SEQ ID NO:187; and (f) HVR-L3 comprising an amino acid sequence selected from SEQ ID NO:190.

In another aspect, the invention provides an antibody comprising (a) HVR-H1 comprising the amino acid sequence of SEQ ID NO:178; (b) HVR-H2 comprising the amino acid sequence of SEQ ID NO:179; (c) HVR-H3 comprising the amino acid sequence of SEQ ID NO:181; (d) HVR-L1 comprising the amino acid sequence of SEQ ID NO:186; (e) HVR-L2 comprising the amino acid sequence of SEQ ID NO:187; and (f) HVR-L3 comprising an amino acid sequence selected from SEQ ID NO:189.

In another aspect, the invention provides an antibody comprising a heavy chain variable region comprising an amino acid sequence selected from the group consisting of SEQ ID NOs:111 and 115.

In another aspect, the invention provides an antibody comprising a light chain variable region comprising an amino acid sequence selected from the group consisting of SEQ ID NOs:113, 117, 119, 122, 124, 126, 128, 130, and 132.

In another aspect, the invention provides an antibody comprising a heavy chain variable region comprising an amino acid sequence selected from the group consisting of SEQ ID NOs:111 and 115 and a light chain variable region comprising an amino acid sequence selected from the group consisting of SEQ ID NOs:113, 117, 119, 122, 124, 126, 128, 130, and 132.

In one embodiment, the invention provides an antibody comprising a heavy chain variable region comprising the amino acid sequence of SEQ ID NO:111 and a light chain variable region comprising the amino acid sequence of SEQ ID NO:113.

In one embodiment, the invention provides an antibody comprising a heavy chain variable region comprising the amino acid sequence of SEQ ID NO:115 and a light chain variable region comprising the amino acid sequence of SEQ ID NO:117.

In one embodiment, the invention provides an antibody comprising a heavy chain variable region comprising the amino acid sequence of SEQ ID NO:111 and a light chain variable region comprising the amino acid sequence of SEQ ID NO:119.

In one embodiment, the invention provides an antibody comprising a heavy chain variable region comprising the amino acid sequence of SEQ ID NO:115 and a light chain variable region comprising the amino acid sequence of SEQ ID NO:113.

In one embodiment, the invention provides an antibody comprising a heavy chain variable region comprising the amino acid sequence of SEQ ID NO:115 and a light chain variable region comprising the amino acid sequence of SEQ ID NO:122.

In one embodiment, the invention provides an antibody comprising a heavy chain variable region comprising the amino acid sequence of SEQ ID NO:115 and a light chain variable region comprising the amino acid sequence of SEQ ID NO:124.

In one embodiment, the invention provides an antibody comprising a heavy chain variable region comprising the amino acid sequence of SEQ ID NO:115 and a light chain variable region comprising the amino acid sequence of SEQ ID NO:126.

In one embodiment, the invention provides an antibody comprising a heavy chain variable region comprising the amino acid sequence of SEQ ID NO:115 and a light chain variable region comprising the amino acid sequence of SEQ ID NO:128.

In one embodiment, the invention provides an antibody comprising a heavy chain variable region comprising the amino acid sequence of SEQ ID NO:115 and a light chain variable region comprising the amino acid sequence of SEQ ID NO:130.

In one embodiment, the invention provides an antibody comprising a heavy chain variable region comprising the amino acid sequence of SEQ ID NO:115 and a light chain variable region comprising the amino acid sequence of SEQ ID NO:132.

In another aspect, the invention provides an antibody comprising a heavy chain comprising an amino acid sequence selected from the group consisting of SEQ ID NOs:110, 114, and 120.

In another aspect, the invention provides an antibody comprising a light chain comprising an amino acid sequence selected from the group consisting of SEQ ID NOs:112, 116, 118, 121, 123, 125, 127, 129, and 131.

In another aspect, the invention provides an antibody comprising a heavy chain comprising an amino acid sequence selected from the group consisting of SEQ ID NOs:110, 114, and 120, and a light chain comprising an amino acid sequence selected from the group consisting of SEQ ID NOs:112, 116, 118, 121, 123, 125, 127, 129, and 131.

In one embodiment, the invention provides an antibody comprising a heavy chain comprising the amino acid sequence of SEQ ID NO:110, and a light chain comprising the amino acid sequence of SEQ ID NO:112.

In one embodiment, the invention provides an antibody comprising a heavy chain comprising the amino acid sequence of SEQ ID NO:114, and a light chain comprising the amino acid sequence of SEQ ID NO:116.

In one embodiment, the invention provides an antibody comprising a heavy chain comprising the amino acid sequence of SEQ ID NO:110, and a light chain comprising the amino acid sequence of SEQ ID NO:118.

In one embodiment, the invention provides an antibody comprising a heavy chain comprising the amino acid sequence of SEQ ID NO:114, and a light chain comprising the amino acid sequence of SEQ ID NO:112.

In one embodiment, the invention provides an antibody comprising a heavy chain comprising the amino acid sequence of SEQ ID NO:120, and a light chain comprising the amino acid sequence of SEQ ID NO:121.

In one embodiment, the invention provides an antibody comprising a heavy chain comprising the amino acid sequence of SEQ ID NO:114, and a light chain comprising the amino acid sequence of SEQ ID NO:123.

In one embodiment, the invention provides an antibody comprising a heavy chain comprising the amino acid sequence of SEQ ID NO:114, and a light chain comprising the amino acid sequence of SEQ ID NO:125.

In one embodiment, the invention provides an antibody comprising a heavy chain comprising the amino acid sequence of SEQ ID NO:114, and a light chain comprising the amino acid sequence of SEQ ID NO:127.

In one embodiment, the invention provides an antibody comprising a heavy chain comprising the amino acid sequence of SEQ ID NO:114, and a light chain comprising the amino acid sequence of SEQ ID NO:129.

In one embodiment, the invention provides an antibody comprising a heavy chain comprising the amino acid sequence of SEQ ID NO:114, and a light chain comprising the amino acid sequence of SEQ ID NO:131.

In one aspect, the invention provides an anti-hemagglutinin antibody comprising at least one, two, three, four, five, or six HVRs selected from (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising the amino acid sequence of SEQ ID NO:197.

In one aspect, the invention provides an anti-hemagglutinin antibody comprising at least one, two, three, four, five, or six HVRs selected from (a) HVR-H1 comprising the amino acid sequence of SEQ ID NO:192; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising the amino acid sequence of SEQ ID NO:197.

In one aspect, the invention provides an anti-hemagglutinin antibody comprising at least one, two, three, four, five, or six HVRs selected from (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising the amino acid sequence of SEQ ID NO:198.

In one aspect, the invention provides an anti-hemagglutinin antibody comprising at least one, two, three, four, five, or six HVRs selected from (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising the amino acid sequence of SEQ ID NO:199.

In one aspect, the invention provides an antibody comprising at least one, at least two, or all three VH HVR sequences selected from (a) HVR-H1 comprising an amino acid sequence selected from the group consisting of SEQ ID NOs:191 and 192; (b) HVR-H2 comprising the amino acid sequence of SEQ ID NO:193; and (c) HVR-H3 comprising the amino acid sequence of SEQ ID NO:194.

In another aspect, the invention provides an antibody comprising at least one, at least two, or all three VL HVR sequences selected from (a) HVR-L1 comprising the amino acid sequence of SEQ ID NO:195; (b) HVR-L2 comprising the amino acid sequence of SEQ ID NO:196; and (c) HVR-L3 comprising an amino acid sequence selected from the group consisting of SEQ ID NOs:197, 198, and 199.

In another aspect, the invention provides an antibody comprising (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising an amino acid sequence selected from SEQ ID NO:197.

In another aspect, the invention provides an antibody comprising (a) HVR-H1 comprising the amino acid sequence of SEQ ID NO:192; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising an amino acid sequence selected from SEQ ID NO:197.

In another aspect, the invention provides an antibody comprising (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising an amino acid sequence selected from SEQ ID NO:198.

In another aspect, the invention provides an antibody comprising (a) HVR-H1 comprising the amino acid sequence of SEQ ID NO:191; (b) HVR-H2 comprising the amino acid sequence of SEQ ID NO:193; (c) HVR-H3 comprising the amino acid sequence of SEQ ID NO:194; (d) HVR-L1 comprising the amino acid sequence of SEQ ID NO:195; (e) HVR-L2 comprising the amino acid sequence of SEQ ID NO:196; and (f) HVR-L3 comprising an amino acid sequence selected from SEQ ID NO:199.

In another aspect, the invention provides an antibody comprising a heavy chain variable region comprising an amino acid sequence selected from the group consisting of SEQ ID NOs:134, 138, 142, 148, and 234.

In another aspect, the invention provides an antibody comprising a light chain variable region comprising an amino acid sequence selected from the group consisting of SEQ ID NOs:136, 140, 144, 146, 150, 152, and 235.

In another aspect, the invention provides an antibody comprising a heavy chain variable region comprising an amino acid sequence selected from the group consisting of SEQ ID NOs:134, 138, 142, 148, and 234, and a light chain variable region comprising an amino acid sequence selected from the group consisting of SEQ ID NOs:136, 140, 144, 146, 150, 152, and 235.

In one embodiment, the invention provides an antibody comprising a heavy chain variable region comprising the amino acid sequence of SEQ ID NO:134 and a light chain variable region comprising the amino acid sequence of SEQ ID NO:136.

In one embodiment, the invention provides an antibody comprising a heavy chain variable region comprising the amino acid sequence of SEQ ID NO:138 and a light chain variable region comprising the amino acid sequence of SEQ ID NO:140.

In one embodiment, the invention provides an antibody comprising a heavy chain variable region comprising the amino acid sequence of SEQ ID NO:142 and a light chain variable region comprising the amino acid sequence of SEQ ID NO:144.

In one embodiment, the invention provides an antibody comprising a heavy chain variable region comprising the amino acid sequence of SEQ ID NO:138 and a light chain variable region comprising the amino acid sequence of SEQ ID NO:146.

In one embodiment, the invention provides an antibody comprising a heavy chain variable region comprising the amino acid sequence of SEQ ID NO:148 and a light chain variable region comprising the amino acid sequence of SEQ ID NO:150.

In one embodiment, the invention provides an antibody comprising a heavy chain variable region comprising the amino acid sequence of SEQ ID NO:148 and a light chain variable region comprising the amino acid sequence of SEQ ID NO:152.

In one embodiment, the invention provides an antibody comprising a heavy chain variable region comprising the amino acid sequence of SEQ ID NO:148 and a light chain variable region comprising the amino acid sequence of SEQ ID NO:140.

In one embodiment, the invention provides an antibody comprising a heavy chain variable region comprising the amino acid sequence of SEQ ID NO:234 and a light chain variable region comprising the amino acid sequence of SEQ ID NO:235.

In another aspect, the invention provides an antibody comprising a heavy chain comprising an amino acid sequence selected from the group consisting of SEQ ID NOs:133, 137, 141, and 147.

In another aspect, the invention provides an antibody comprising a light chain comprising an amino acid sequence selected from the group consisting of SEQ ID NOs:135, 139, 143, 145, 149, and 151.

In another aspect, the invention provides an antibody comprising a heavy chain comprising an amino acid sequence selected from the group consisting of SEQ ID NOs:133, 137, 141, and 147, and a light chain comprising an amino acid sequence selected from the group consisting of SEQ ID NOs:135, 139, 143, 145, 149, and 151.

In one embodiment, the invention provides an antibody comprising a heavy chain comprising the amino acid sequence of SEQ ID NO:133, and a light chain comprising the amino acid sequence of SEQ ID NO:135.

In one embodiment, the invention provides an antibody comprising a heavy chain comprising the amino acid sequence of SEQ ID NO:137, and a light chain comprising the amino acid sequence of SEQ ID NO:139.

In one embodiment, the invention provides an antibody comprising a heavy chain comprising the amino acid sequence of SEQ ID NO:141, and a light chain comprising the amino acid sequence of SEQ ID NO:143.

In one embodiment, the invention provides an antibody comprising a heavy chain comprising the amino acid sequence of SEQ ID NO:137, and a light chain comprising the amino acid sequence of SEQ ID NO:145.

In one embodiment, the invention provides an antibody comprising a heavy chain comprising the amino acid sequence of SEQ ID NO:147, and a light chain comprising the amino acid sequence of SEQ ID NO:149.

In one embodiment, the invention provides an antibody comprising a heavy chain comprising the amino acid sequence of SEQ ID NO:147, and a light chain comprising the amino acid sequence of SEQ ID NO:151.

In one embodiment, the invention provides an antibody comprising a heavy chain comprising the amino acid sequence of SEQ ID NO:147, and a light chain comprising the amino acid sequence of SEQ ID NO:139.

In one aspect, the invention provides an anti-hemagglutinin antibody comprising at least one, two, three, four, five, or six HVRs selected from (a) HVR-H1 comprising the amino acid sequence of SEQ ID NO:200; (b) HVR-H2 comprising the amino acid sequence of SEQ ID NO:201; (c) HVR-H3 comprising the amino acid sequence of SEQ ID NO:202; (d) HVR-L1 comprising the amino acid sequence of SEQ ID NO:203; (e) HVR-L2 comprising the amino acid sequence of SEQ ID NO:204; and (f) HVR-L3 comprising the amino acid sequence of SEQ ID NO:205.

In one aspect, the invention provides an antibody comprising at least one, at least two, or all three VH HVR sequences selected from (a) HVR-H1 comprising the amino acid sequence of SEQ ID NO:200; (b) HVR-H2 comprising the amino acid sequence of SEQ ID NO:201; and (c) HVR-H3 comprising the amino acid sequence of SEQ ID NO:202.

In another aspect, the invention provides an antibody comprising at least one, at least two, or all three VL HVR sequences selected from (a) HVR-L1 comprising the amino acid sequence of SEQ ID NO:203; (b) HVR-L2 comprising the amino acid sequence of SEQ ID NO:204; and (c) HVR-L3 comprising the amino acid sequence of SEQ ID NO:205.

In another aspect, the invention provides an antibody comprising (a) HVR-H1 comprising the amino acid sequence of SEQ ID NO:200; (b) HVR-H2 comprising the amino acid sequence of SEQ ID NO:201; (c) HVR-H3 comprising the amino acid sequence of SEQ ID NO:202; (d) HVR-L1 comprising the amino acid sequence of SEQ ID NO:203; (e) HVR-L2 comprising the amino acid sequence of SEQ ID NO:204; and (f) HVR-L3 comprising the amino acid sequence of SEQ ID NO:205.

In another aspect, the invention provides an antibody comprising a heavy chain variable region comprising an amino acid sequence selected from the group consisting of SEQ ID NOs:154 and 158.

In another aspect, the invention provides an antibody comprising a light chain variable region comprising the amino acid sequence of SEQ ID NO:156.

In another aspect, the invention provides an antibody comprising a heavy chain variable region comprising an amino acid sequence selected from the group consisting of SEQ ID NOs:154 and 158, and a light chain variable region comprising the amino acid sequence of SEQ ID NO:156.

In one embodiment, the invention provides an antibody comprising a heavy chain variable region comprising the amino acid sequence of SEQ ID NO:154 and a light chain variable region comprising the amino acid sequence of SEQ ID NO:156.

In one embodiment, the invention provides an antibody comprising a heavy chain variable region comprising the amino acid sequence of SEQ ID NO:158 and a light chain variable region comprising the amino acid sequence of SEQ ID NO:156.

In another aspect, the invention provides an antibody comprising a heavy chain comprising an amino acid sequence selected from the group consisting of SEQ ID NOs:153 and 157.

In another aspect, the invention provides an antibody comprising a light chain comprising the amino acid sequence of SEQ ID NO:155.

In another aspect, the invention provides an antibody comprising a heavy chain comprising an amino acid sequence selected from the group consisting of SEQ ID NOs:153 and 157, and a light chain comprising the amino acid sequence of SEQ ID NO:155.

In one embodiment, the invention provides an antibody comprising a heavy chain comprising the amino acid sequence of SEQ ID NO:153, and a light chain comprising the amino acid sequence of SEQ ID NO:155.

In one embodiment, the invention provides an antibody comprising a heavy chain comprising the amino acid sequence of SEQ ID NO:157, and a light chain comprising the amino acid sequence of SEQ ID NO:155.

In one aspect, the invention provides an anti-hemagglutinin antibody comprising at least one, two, three, four, five, or six HVRs selected from (a) HVR-H1 comprising the amino acid sequence of SEQ ID NO:206; (b) HVR-H2 comprising the amino acid sequence of SEQ ID NO:207; (c) HVR-H3 comprising the amino acid sequence of SEQ ID NO:208; (d) HVR-L1 comprising the amino acid sequence of SEQ ID NO:209; (e) HVR-L2 comprising the amino acid sequence of SEQ ID NO:210; and (f) HVR-L3 comprising the amino acid sequence of SEQ ID NO:211.

In one aspect, the invention provides an antibody comprising at least one, at least two, or all three VH HVR sequences selected from (a) HVR-H1 comprising the amino acid sequence of SEQ ID NO:206; (b) HVR-H2 comprising the amino acid sequence of SEQ ID NO:207; and (c) HVR-H3 comprising the amino acid sequence of SEQ ID NO:208.

In another aspect, the invention provides an antibody comprising at least one, at least two, or all three VL HVR sequences selected from (a) HVR-L1 comprising the amino acid sequence of SEQ ID NO:209; (b) HVR-L2 comprising the amino acid sequence of SEQ ID NO:210; and (c) HVR-L3 comprising the amino acid sequence of SEQ ID NO:211.

In another aspect, the invention provides an antibody comprising (a) HVR-H1 comprising the amino acid sequence of SEQ ID NO:206; (b) HVR-H2 comprising the amino acid sequence of SEQ ID NO:207; (c) HVR-H3 comprising the amino acid sequence of SEQ ID NO:208; (d) HVR-L1 comprising the amino acid sequence of SEQ ID NO:209; (e) HVR-L2 comprising the amino acid sequence of SEQ ID NO:210; and (f) HVR-L3 comprising the amino acid sequence of SEQ ID NO:211.

In another aspect, the invention provides an antibody comprising a heavy chain variable region comprising the amino acid sequence of SEQ ID NO:160.

In another aspect, the invention provides an antibody comprising a light chain variable region comprising the amino acid sequence of SEQ ID NO:162.

In one embodiment, the invention provides an antibody comprising a heavy chain variable region comprising the amino acid sequence of SEQ ID NO:160 and a light chain variable region comprising the amino acid sequence of SEQ ID NO:162.

In another aspect, the invention provides an antibody comprising a heavy chain comprising the amino acid sequence of SEQ ID NO:159.

In another aspect, the invention provides an antibody comprising a light chain comprising the amino acid sequence of SEQ ID NO:161.

In another aspect, the invention provides an antibody comprising a heavy chain comprising the amino acid sequence of SEQ ID NO:159, and a light chain comprising the amino acid sequence of SEQ ID NO:161.

In one aspect, the invention provides an anti-hemagglutinin antibody comprising at least one, two, three, four, five, or six HVRs selected from (a) HVR-H1 comprising the amino acid sequence of SEQ ID NO:212; (b) HVR-H2 comprising the amino acid sequence of SEQ ID NO:213; (c) HVR-H3 comprising the amino acid sequence of SEQ ID NO:214; (d) HVR-L1 comprising the amino acid sequence of SEQ ID NO:215; (e) HVR-L2 comprising the amino acid sequence of SEQ ID NO:216; and (f) HVR-L3 comprising the amino acid sequence of SEQ ID NO:217.

In one aspect, the invention provides an antibody comprising at least one, at least two, or all three VH HVR sequences selected from (a) HVR-H1 comprising the amino acid sequence of SEQ ID NO:212; (b) HVR-H2 comprising the amino acid sequence of SEQ ID NO:213; and (c) HVR-H3 comprising the amino acid sequence of SEQ ID NO:214.

In another aspect, the invention provides an antibody comprising at least one, at least two, or all three VL HVR sequences selected from (a) HVR-L1 comprising the amino acid sequence of SEQ ID NO:215; (b) HVR-L2 comprising the amino acid sequence of SEQ ID NO:216; and (c) HVR-L3 comprising the amino acid sequence of SEQ ID NO:217.

In another aspect, the invention provides an antibody comprising (a) HVR-H1 comprising the amino acid sequence of SEQ ID NO:212; (b) HVR-H2 comprising the amino acid sequence of SEQ ID NO:213; (c) HVR-H3 comprising the amino acid sequence of SEQ ID NO:214; (d) HVR-L1 comprising the amino acid sequence of SEQ ID NO:215; (e) HVR-L2 comprising the amino acid sequence of SEQ ID NO:216; and (f) HVR-L3 comprising the amino acid sequence of SEQ ID NO:217.

In another aspect, the invention provides an antibody comprising a heavy chain variable region comprising the amino acid sequence of SEQ ID NO:164.

In another aspect, the invention provides an antibody comprising a light chain variable region comprising the amino acid sequence of SEQ ID NO:166.

In one embodiment, the invention provides an antibody comprising a heavy chain variable region comprising the amino acid sequence of SEQ ID NO:164 and a light chain variable region comprising the amino acid sequence of SEQ ID NO:166.

In another aspect, the invention provides an antibody comprising a heavy chain comprising the amino acid sequence of SEQ ID NO:163.

In another aspect, the invention provides an antibody comprising a light chain comprising the amino acid sequence of SEQ ID NO:165.

In another aspect, the invention provides an antibody comprising a heavy chain comprising the amino acid sequence of SEQ ID NO:163, and a light chain comprising the amino acid sequence of SEQ ID NO:165.

In one aspect, the invention provides an anti-hemagglutinin antibody comprising at least one, two, three, four, five, or six HVRs selected from (a) HVR-H1 comprising the amino acid sequence of SEQ ID NO:218; (b) HVR-H2 comprising the amino acid sequence of SEQ ID NO:219; (c) HVR-H3 comprising the amino acid sequence of SEQ ID NO:220; (d) HVR-L1 comprising the amino acid sequence of SEQ ID NO:221; (e) HVR-L2 comprising the amino acid sequence of SEQ ID NO:222; and (f) HVR-L3 comprising the amino acid sequence of SEQ ID NO:223.

In one aspect, the invention provides an antibody comprising at least one, at least two, or all three VH HVR sequences selected from (a) HVR-H1 comprising the amino acid sequence of SEQ ID NO:218; (b) HVR-H2 comprising the amino acid sequence of SEQ ID NO:219; and (c) HVR-H3 comprising the amino acid sequence of SEQ ID NO:220.

In another aspect, the invention provides an antibody comprising at least one, at least two, or all three VL HVR sequences selected from (a) HVR-L1 comprising the amino acid sequence of SEQ ID NO:221; (b) HVR-L2 comprising the amino acid sequence of SEQ ID NO:222; and (c) HVR-L3 comprising the amino acid sequence of SEQ ID NO:223.

In another aspect, the invention provides an antibody comprising (a) HVR-H1 comprising the amino acid sequence of SEQ ID NO:218; (b) HVR-H2 comprising the amino acid sequence of SEQ ID NO:219; (c) HVR-H3 comprising the amino acid sequence of SEQ ID NO:220; (d) HVR-L1 comprising the amino acid sequence of SEQ ID NO:221; (e) HVR-L2 comprising the amino acid sequence of SEQ ID NO:222; and (f) HVR-L3 comprising the amino acid sequence of SEQ ID NO:223.

In another aspect, the invention provides an antibody comprising a heavy chain variable region comprising the amino acid sequence of SEQ ID NO:168.

In another aspect, the invention provides an antibody comprising a light chain variable region comprising the amino acid sequence of SEQ ID NO:170.

In one embodiment, the invention provides an antibody comprising a heavy chain variable region comprising the amino acid sequence of SEQ ID NO:168 and a light chain variable region comprising the amino acid sequence of SEQ ID NO:170.

In another aspect, the invention provides an antibody comprising a heavy chain comprising the amino acid sequence of SEQ ID NO:167.

In another aspect, the invention provides an antibody comprising a light chain comprising the amino acid sequence of SEQ ID NO:169.

In another aspect, the invention provides an antibody comprising a heavy chain comprising the amino acid sequence of SEQ ID NO:167, and a light chain comprising the amino acid sequence of SEQ ID NO:169.

In any of the above embodiments, an anti-hemagglutinin antibody of the present invention is humanized. In one embodiment, an anti-hemagglutinin antibody comprises HVRs as in any of the above embodiments, and further comprises an acceptor human framework, e.g., a human immunoglobulin framework or a human consensus framework.

In another aspect, an anti-hemagglutinin antibody of the present comprises a heavy chain variable domain (VH) sequence having at least 90%, 91%, 92%, 93%, 94%, 95%, 96%, 97%, 98%, 99%, or 100% sequence identity to an amino acid sequence selected from the group consisting of SEQ ID NOs:111, 115, 134, 138, 142, 148, 154, 158, 160, 164, 168, and 234. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-hemagglutinin antibody comprising that sequence retains the ability to bind to hemagglutinin. In certain embodiments, a total of 1 to 10 amino acids have been substituted, inserted and/or deleted in SEQ ID NOs: 111, 115, 134, 138, 142, 148, 154, 158, 160, 164, 168, or 234. In certain embodiments, substitutions, insertions, or deletions occur in regions outside the HVRs (i.e., in the FRs). Optionally, the anti hemagglutinin antibody comprises the VH sequence in SEQ ID NO: 111, 115, 134, 138, 142, 148, 154, 158, 160, 164, 168, or 234, including post-translational modifications of that sequence.

In another aspect, an anti-hemagglutinin antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from the group consisting of SEQ ID NOs:113, 117, 119, 122, 124, 126, 128, 130, 132, 136, 140, 144, 146, 150, 152, 156, 162, 166, 170, and 235. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-hemagglutinin antibody comprising that sequence retains the ability to bind to hemagglutinin. In certain embodiments, a total of 1 to 10 amino acids have been substituted, inserted and/or deleted in SEQ ID NOs: 113, 117, 119, 122, 124, 126, 128, 130, 132, 136, 140, 144, 146, 150, 152, 156, 162, 166, 170, or 235. In certain embodiments, the substitutions, insertions, or deletions occur in regions outside the HVRs (i.e., in the FRs). Optionally, the anti-hemagglutinin antibody comprises the VL sequence in SEQ ID NOs: 113, 117, 119, 122, 124, 126, 128, 130, 132, 136, 140, 144, 146, 150, 152, 156, 162, 166, 170, or 235, including post-translational modifications of that sequence.

In another aspect, an anti-hemagglutinin antibody is provided, wherein the antibody comprises a VH as in any of the embodiments provided above, and a VL as in any of the embodiments provided above. In one embodiment, the antibody comprises the VH and VL sequences in SEQ ID NOs: 111, 115, 134, 138, 142, 148, 154, 158, 160, 164, 168, or 234, and SEQ ID NOs: 113, 117, 119, 122, 124, 126, 128, 130, 132, 136, 140, 144, 146, 150, 152, 156, 162, 166, 170, or 235, respectively, including post-translational modifications of those sequences.

In a further aspect, the invention provides an antibody that binds to the same epitope as an anti-hemagglutinin antibody provided herein. For example, in certain embodiments, an antibody is provided that binds to the same epitope as an anti-hemagglutinin antibody comprising a VH sequence of SEQ ID NO:111 and a VL sequence of SEQ ID NO:113; a VH sequence of SEQ ID NO:115 and a VL sequence of SEQ ID NO:117; a VH sequence of SEQ ID NO:111 and a VL sequence of SEQ ID NO:119; a VH sequence of SEQ ID NO:115 and a VL sequence of SEQ ID NO:113; a VH sequence of SEQ ID NO:115 and a VL sequence of SEQ ID NO:122; a VH sequence of SEQ ID NO:115 and a VL sequence of SEQ ID NO:124; a VH sequence of SEQ ID NO:115 and a VL sequence of SEQ ID NO:126; a VH sequence of SEQ ID NO:115 and a VL sequence of SEQ ID NO:128; a VH sequence of SEQ ID NO:115 and a VL sequence of SEQ ID NO:130; a VH sequence of SEQ ID NO:115 and a VL sequence of SEQ ID NO:132; a VH sequence of SEQ ID NO:134 and a VL sequence of SEQ ID NO:136; a VH sequence of SEQ ID NO:138 and a VL sequence of SEQ ID NO:140; a VH sequence of SEQ ID NO:142 and a VL sequence of SEQ ID NO:144; a VH sequence of SEQ ID NO:138 and a VL sequence of SEQ ID NO:146; a VH sequence of SEQ ID NO:148 and a VL sequence of SEQ ID NO:150; a VH sequence of SEQ ID NO:148 and a VL sequence of SEQ ID NO:152; a VH sequence of SEQ ID NO:148 and a VL sequence of SEQ ID NO:140; a VH sequence of SEQ ID NO:234 and a VL sequence of SEQ ID NO:235; a VH sequence of SEQ ID NO:154 and a VL sequence of SEQ ID NO:156; a VH sequence of SEQ ID NO:158 and a VL sequence of SEQ ID NO:156; a VH sequence of SEQ ID NO:160 and a VL sequence of SEQ ID NO:162; a VH sequence of SEQ ID NO:164 and a VL sequence of SEQ ID NO:166; or a VH sequence of SEQ ID NO:168 and a VL sequence of SEQ ID NO:170.

In a further aspect of the invention, an anti-hemagglutinin antibody according to any of the above embodiments is a monoclonal antibody, including a chimeric, humanized, or human antibody.

In one embodiment, an anti-hemagglutinin antibody is an antibody fragment, e.g., a Fv, Fab, Fab', scFv, diabody, or F(ab')$_2$ fragment. In another embodiment, the antibody is a full length antibody, e.g., an intact, e.g., IgG1 antibody or other antibody class or isotype as defined herein.

In a further aspect, an anti-hemagglutinin antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art or using techniques described herein. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al, *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N. J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g., a bispecific antibody. Multispecific antibodies are monoclonal antibodies that have binding specificities for at least two different sites. In certain embodiments, one of the binding specificities is for hemagglutinin and the other is for any other antigen. In certain embodiments, bispecific antibodies may bind to two different epitopes of hemagglutinin. Bispecific antibodies may also be used to localize cytotoxic agents to cells which express hemagglutinin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The antibody or fragment herein also includes a "Dual Acting FAb" or "DAF" comprising an antigen binding site that binds to hemagglutinin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch. Biochem. Biophys.* 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-hemagglutinin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-hemagglutinin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-hemagglutinin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, N.J., 2003), pp. 245-254, describing expression of antibody fragments in *E. coli*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, N.J.), pp. 255-268 (2003).

C. Assays

Anti-hemagglutinin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes for binding of hemagglutinin with any anti-hemagglutinin antibody described herein. In certain embodiments, such a competing antibody binds to the same epitope (e.g., a linear or a conformational epitope) that is bound by an anti-hemagglutinin antibody described here (e.g., an anti-hemagglutinin antibody comprising a VH sequence of SEQ ID NO:111 and a VL sequence of SEQ ID NO:113; a VH sequence of SEQ ID NO:115 and a VL sequence of SEQ ID NO:117; a VH sequence of SEQ ID NO:111 and a VL sequence of SEQ ID NO:119; a VH sequence of SEQ ID NO:115 and a VL sequence of SEQ ID NO:113; a VH sequence of SEQ ID NO:115 and a VL sequence of SEQ ID NO:122; a VH sequence of SEQ ID NO:115 and a VL sequence of SEQ ID NO:124; a VH sequence of SEQ ID NO:115 and a VL sequence of SEQ ID NO:126; a VH sequence of SEQ ID NO:115 and a VL sequence of SEQ ID NO:128; a VH sequence of SEQ ID NO:115 and a VL sequence of SEQ ID NO:130; a VH sequence of SEQ ID NO:115 and a VL sequence of SEQ ID NO:132; a VH sequence of SEQ ID NO:134 and a VL sequence of SEQ ID NO:136; a VH sequence of SEQ ID NO:138 and a VL sequence of SEQ ID NO:140; a VH sequence of SEQ ID NO:142 and a VL sequence of SEQ ID NO:144; a VH sequence of SEQ ID NO:138 and a VL sequence of SEQ ID NO:146; a VH sequence of SEQ ID NO:148 and a VL sequence of SEQ ID NO:150; a VH sequence of SEQ ID NO:148 and a VL sequence of SEQ ID NO:152; a VH sequence of SEQ ID NO:148 and a VL sequence of SEQ ID NO:140; a VH sequence of SEQ ID NO:234 and a VL sequence of SEQ ID NO:235; a VH sequence of SEQ ID NO:154 and a VL sequence of SEQ ID NO:156; a VH sequence of SEQ ID NO:158 and a VL sequence of SEQ ID NO:156; a VH sequence of SEQ ID NO:160 and a VL sequence of SEQ ID NO:162; a VH sequence of SEQ ID NO:164 and a VL sequence of SEQ ID NO:166; or a VH sequence of SEQ ID NO:168 and a VL sequence of SEQ ID NO:170. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized hemagglutinin is incubated in a solution comprising a first labeled antibody that binds to hemagglutinin and a second unlabeled antibody that is being tested for its ability to compete with the first antibody for binding to hemagglutinin. The second antibody may be present in a hybridoma supernatant. As a control, immobilized hemagglutinin is incubated in a solution comprising the first labeled antibody but not the second unlabeled antibody. After incubation under conditions permissive for binding of the first antibody to hemagglutinin, excess unbound antibody is removed, and the amount of label associated with immobilized hemagglutinin is measured. If the amount of label associated with immobilized hemagglutinin is substantially reduced in the test sample relative to the control sample, then that indicates that the second antibody is competing with the first antibody for binding to hemagglutinin. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-hemagglutinin antibodies and fragments thereof having biological activity. Biological activity may include, e.g., specifically binding to influenza A virus hemagglutinin, neutralizing influenza A virus, etc. Antibodies and compositions comprising antibodies or fragments thereof having such biological activity in vivo and/or in vitro are also provided.

In certain embodiments, an antibody of the invention is tested for such biological activity. See Examples 4, 5, 6, 7, 8, 9, 10, and 13 for exemplary descriptions of such assays.

D. Immunoconjugates

The invention also provides immunoconjugates comprising an anti-hemagglutinin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic &Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinyl sulfone)benzoate) which are commercially available (e.g., from Pierce Biotechnology, Inc., Rockford, Ill., U.S.A).

E. Methods and Compositions for Diagnostics and Detection

In certain embodiments, any of the anti-hemagglutinin antibodies provided herein is useful for detecting the presence of hemagglutinin or influenza A virus in a biological sample. The term "detecting" as used herein encompasses quantitative or qualitative detection. In certain embodiments, a biological sample comprises a cell or tissue, such as, for example, lung, upper respiratory tract, nasal canal, blood, sputum, or comprises a biological sample obtained by nasal or throat swab.

In one embodiment, an anti-hemagglutinin antibody for use in a method of diagnosis or detection is provided. In a further aspect, a method of detecting the presence of hemagglutinin or influenza A virus in a biological sample is provided. In certain embodiments, the method comprises contacting the biological sample with an anti-hemagglutinin antibody as described herein under conditions permissive for binding of the anti-hemagglutinin antibody to hemagglutinin, and detecting whether a complex is formed between the anti-hemagglutinin antibody and hemagglutinin. Such method may be an in vitro or in vivo method. In one embodiment, an anti-hemagglutinin antibody is used to select subjects eligible for therapy with an anti-hemagglutinin antibody, e.g., where hemagglutinin is a biomarker for selection of patients.

Exemplary disorders that may be diagnosed using an antibody of the invention include influenza A virus infection, including influenza A virus infection in children, infants, adults, and the elderly.

In certain embodiments, labeled anti-hemagglutinin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-hemagglutinin antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Application Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a neuraminidase inhibitor, an anti-hemagglutinin antibody, an anti-M2 antibody, etc. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. The formulations to be used for in vivo administration are generally sterile. Sterility may be readily accomplished, e.g., by filtration through sterile filtration membranes.

G. Therapeutic Methods and Compositions

Any of the anti-hemagglutinin antibodies provided herein may be used in therapeutic methods.

In one aspect, an anti-hemagglutinin antibody for use as a medicament is provided. In further aspects, an anti-hemagglutinin antibody for use in treating, preventing, or inhibiting influenza A virus infection is provided. In certain embodiments, an anti-hemagglutinin antibody for use in a method of treatment is provided. In certain embodiments, the invention provides an anti-hemagglutinin antibody for use in a method of treating an individual having influenza A virus infection comprising administering to the individual an effective amount of the anti-hemagglutinin antibody. In one such embodiment, the method further comprises administering to the individual an effective amount of at least one additional therapeutic agent, e.g., as described below. In further embodiments, the invention provides an anti-hemagglutinin antibody for use in preventing, inhibiting, or reducing hemagglutinin-mediated fusion between influenza A virus viral membrane and infected cell endosomal membranes, thus preventing viral RNA entry into the infected cell cytoplasm and preventing further propagation of infection. In certain embodiments, the invention provides an anti-hemagglutinin antibody for use in a method of preventing, inhibiting, or treating influenza A virus infection in an individual comprising administering to the individual an effective amount of the anti-hemagglutinin antibody to prevent, inhibit, or treat influenza A virus infection. An "individual" according to any of the above embodiments is preferably a human.

In a further aspect, the invention provides for the use of an anti-hemagglutinin antibody in the manufacture or preparation of a medicament. In one embodiment, the medicament is for treatment of influenza A virus infection. In a further embodiment, the medicament is for use in a method of treating influenza A virus infection comprising administering to an individual having influenza A virus infection an effective amount of the medicament. In one such embodiment, the method further comprises administering to the individual an effective amount of at least one additional therapeutic agent, e.g., as described below. In a further embodiment, the medicament is for preventing, inhibiting, or reducing hemagglutinin-mediated fusion between influenza A virus viral membrane and infected cell endosomal membranes, thus preventing viral RNA entry into the infected cell cytoplasm and preventing further propagation of infection. In a further embodiment, the medicament is for use in a method of preventing, inhibiting, or treating influenza A virus infection in an individual comprising administering to the individual an amount effective of the medicament to prevent, inhibit, or reduce, influenza A virus infection. An "individual" according to any of the above embodiments may be a human.

In a further aspect, the invention provides a method for treating influenza A virus infection. In one embodiment, the method comprises administering to an individual having such influenza A virus infection an effective amount of an anti-hemagglutinin antibody. In one such embodiment, the method further comprises administering to the individual an effective amount of at least one additional therapeutic agent, as described herein. An "individual" according to any of the above embodiments may be a human.

The present invention provides anti-hemagglutinin antibodies effective at inhibiting, preventing, or treating influenza A virus infection in an individual (e.g., a subject or a patient). In some aspects, an anti-hemagglutinin antibody of the present invention is effective at prophylactically treating an individual in order to prevent influenza A virus infection of the individual.

In some aspects, an individual suitable for treatment with an anti-hemagglutinin antibody of the present invention is an individual having or suspected having influenza A virus infection. In some embodiments, such individuals include infants, children, adults, and the elderly. In some embodiments, the individual is hospitalized with influenza A virus infection. In other embodiments, the individual having influenza A virus infection has one or more co-morbidities, such as, for example, immunodeficiency, pregnancy, lung disease, heart disease, renal disease, or co-infection (e.g., a bacterial infection or a viral infection, such as bacterial or viral pneumonia).

In some aspects, treatment of an individual with an anti-hemagglutinin antibody of the present invention reduces influenza A virus infection severity, reduces the length of influenza A virus infection, or reduces influenza A virus infectivity. In other aspects, treatment of influenza A virus infection with an anti-hemagglutinin antibody of the present invention provides additional benefit, including a reduction in the length of hospital stay, reduction or prevention of the need for intensive care unit (ICU) use, reduction or prevention of the need for assisted or mechanical ventilation, reduction or prevention of the need for supplemental oxygen use, and reduction of mortality. In some aspects, the reduction in the length of hospital stay is 1 day, 2 days, 3 days, 4 days, 5 days, or longer than 5 days. In some aspects, the reduction in the need for intensive care unit use is 1 day, 2 days, 3 days, 4 days, 5 days, or longer than 5 days. In some aspects, the reduction in need for assisted or mechanical ventilation is 1 day, 2 days, 3 days, 4 days, 5 days, or longer than 5 days. In some aspects, the reduction in the need for supplemental oxygen is 1 day, 2 days, 3 days, 4 days, 5 days, or longer than 5 days. In some aspects, treatment of an individual with an anti-hemagglutinin antibody of the present invention reduces influenza A virus infection disease symptoms, such as, for example, fever, coryza, chills, sore throat, muscle pain, body aches, headache, cough, nasal congestion, weakness or fatigue, irritated or watering eyes, and general discomfort.

In some aspects, treatment of an individual with an anti-hemagglutinin antibody of the present invention reduces the time to normalization of respiratory function, such as a reduction of time to normalization of respiratory rate, or a reduction of time to normalization of oxygen saturation. In some aspects, treatment of an individual with an anti-hemagglutinin antibody of the present invention reduces the time to return to normal oxygen saturation, e.g., to an oxygen saturation of about 92% or greater, as measured over a 24 hour period without supplemental oxygen administration. In other aspects, treatment of an individual with an anti-hemagglutinin antibody of the present invention reduces the time to normalization of vital signs, such as heart rate, blood pressure, respiratory rate, and temperature.

In some aspects, treatment of an individual with an anti-hemagglutinin antibody of the present invention improves virologic endpoints, such as, for example, influenza virus titer. Virus titer can be measured by various ways known to one of skill in the art, such as, for example, viral area under the curve (AUC), as measured by, for example, qPCR or tissue culture infective does (TCID50). In some aspects, the treatment results in greater than or equal to 50% reduction in viral AUC as measured by qPCR or TCID50.

In various aspects of the present invention, an anti-hemagglutinin antibody provided herein is effective at treating influenza A virus infection when administered at about 12 hours, at about 24 hours, at about 36 hours, at about 48 hours, at about 60 hours, at about 72 hours, at about 84 hours, and at about 96 hours after onset of symptoms (e.g., onset of illness). In other aspects, an anti-hemagglutinin antibody provided herein is effective at treating influenza A virus infection when administered between about 24 hours and 48 hours after onset of symptoms (e.g., the individual has been symptomatic for between 24 and 48 hours), when administered between about 48 hours and 72 hours after onset of symptoms, or when administered between about 72 hours and 96 hours after onset of symptoms. In certain embodiments of the present invention, an anti-hemagglutinin antibody of the present invention is effective at treating or reducing influenza A virus infection and extends the treatment window of current standard of care (e.g., oseltamivir) beyond 48 hours after onset of symptoms.

In a further aspect, the invention provides pharmaceutical formulations comprising any of the anti-hemagglutinin antibodies provided herein, e.g., for use in any of the above therapeutic methods. In one embodiment, a pharmaceutical formulation comprises any of the anti-hemagglutinin antibodies provided herein and a pharmaceutically acceptable carrier. In another embodiment, a pharmaceutical formulation comprises any of the anti-hemagglutinin antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a neuraminidase inhibitor (e.g., zanamivir, oseltamivir phosphate, amantadine, rimantadine), an anti-M2 antibody, an anti-hemagglutinin antibody, etc. In some aspects, treatment of an individual having influenza A virus infection with an anti-hemagglutinin antibody of the present invention co-administered with a neuraminidase inhibitor provides a synergistic therapeutic effect compared to treatment with either agent alone.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-hemagglutinin antibody and administration of an additional therapeutic agent occur within about one month, or within about one, two, or three weeks, within about one, two, three, four, five, or six days, or within about one, two, three, four, five, six, eight, ten, twelve, sixteen, twenty, or twenty-four hours of each other.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to about 45 mg/kg (e.g., about 1.0 mg/kg to about 15 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. Exemplary dosages of the antibody would be in the range from about 1.0 mg/kg to about 45 mg/kg, from about 1.0 mg/kg to about 30 mg/kg, from about 1.0 mg/kg to about 15 mg/kg, from about 1.0 mg/kg to about 10 mg/kg, or from about 1.0 mg/kg to about 5 mg/kg. Thus, one or more doses of about 1.0 mg/kg, 2.5 mg/kg, 5.0 mg/kg, 10 mg/kg, 15 mg/kg, 30 mg/kg, or 45 mg/kg (or any combination thereof) may be administered to the patient. Such doses may be administered intermittently, e.g., every day, every two days, every three days, etc. An initial higher loading dose, followed by one or more lower doses may be administered. Dosing can also be at a fixed dose, such as, for example, 200 mg, 400 mg, 600 mg, 800 mg, 1000 mg, 1200 mg, 1400 mg, 1500 mg, 1600 mg, 1800 mg, 2000 mg, 2200 mg, 2400 mg, 2500 mg, 2600 mg, 2800 mg, 3000 mg, 3200 mg, 3400 mg, 3600 mg, etc. The progress of this therapy is easily monitored by conventional techniques and assays.

It is understood that any of the above formulations or therapeutic methods may be carried out using an immunoconjugate of the invention in place of or in addition to an anti-hemagglutinin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-hemagglutinin antibody.

III. Examples

The following are examples of methods and compositions of the invention. It is understood that various other embodiments may be practiced, given the general description provided above.

Example 1. Identification of Anti-Hemagglutinin Antibodies by Phage Display Construction of Phage Libraries from Influenza Virus Vaccinated Human Donors Antibodies directed against influenza A virus hemagglutinin were identified using a phage display library constructed from peripheral blood mononuclear cells (PBMCs) isolated from human donors vaccinated with the seasonal influenza virus vaccine as follows.

Leukopacs from normal human donors that received the seasonal influenza Fluvirin® vaccine (Novartis Lot #111796P1) 7 days prior to their blood donation were obtained from Blood Centers of the Pacific (San Francisco, Calif.). PBMCs were isolated from the leukopacs using standard methodologies. The PBMCs were sorted for CD19+/CD20− plasmablast cells by FACS. RNA from the CD19+/CD20− sorted plasmablasts was extracted using RNeasy purification kit (Qiagen, USA) and cDNA was generated from the isolated RNA by reverse transcription using SuperScript® III Reverse Transcriptase (Invitrogen, USA). Human variable heavy (VH), variable kappa (VK), and variable light (VL) genes were PCR amplified from the cDNA using the following back and forward DNA primer mixtures.

```
VH Back
BssHII.HuVH1:
                                         (SEQ ID NO: 1)
ATCGTTTCATAAGCGCGCCAGGTGCAGCTGGTGCAGTC BssHII.HuVH2:
                                         (SEQ ID NO: 2)
ATCGTTTCATAAGCGCGCCAGRTCACCTTGAAGGAGTC BssHII.HuVH3.1:
                                         (SEQ ID NO: 3)
ATCGTTTCATAAGCGCGCGAGGTGCAGCTGGTGGAGTC BssHII.HuVH3.2:
                                         (SEQ ID NO: 4)
ATCGTTTCATAAGCGCGCCAGGTGCAGCTGGTGGAGTC BssHII.HuVH3.3:
                                         (SEQ ID NO: 5)
ATCGTTTCATAAGCGCGCGAAGTGCAGCTGGTGGAGTC BssHII.HuVH4.1:
                                         (SEQ ID NO: 6)
ATCGTTTCATAAGCGCGCCAGGTGCAGCTGCAGGAGTC BssHII.HuVH4.2:
                                         (SEQ ID NO: 7)
ATCGTTTCATAAGCGCGCCAGCTGCAGCTGCAGGAGTC BssHII.HuVH5:
                                         (SEQ ID NO: 8)
ATCGTTTCATAAGCGCGCGARGTGCAGCTGGTGCAGTC BssHII.HuVH6:
                                         (SEQ ID NO: 9)
ATCGTTTCATAAGCGCGCCAGGTACAGCTGCAGCAGTC BssHII.HuVH7:
                                        (SEQ ID NO: 10)
ATCGTTTCATAAGCGCGCCAGGTGCAGCTGGTGCAATC BssHII.HuVH1.A:
                                        (SEQ ID NO: 11)
ATCGTTTCATAAGCGCGCCAGGTCCAGCTTGTGCAGTC BssHII.HuVH1.B:
                                        (SEQ ID NO: 12)
ATCGTTTCATAAGCGCGCCAGGTTCAGCTGGTGCAGTC BssHII.HuVH1.C:
                                        (SEQ ID NO: 13)
ATCGTTTCATAAGCGCGCCAGGTCCAGCTGGTACAGTC BssHII.HuVH1.D:
                                        (SEQ ID NO: 14)
ATCGTTTCATAAGCGCGCCAGATGCAGCTGGTGCAGTC BssHII.HuVH1.E:
                                        (SEQ ID NO: 15)
ATCGTTTCATAAGCGCGCCAAATCCAGCTGGTGCAGTC BssHII.HuVH1.F :
                                        (SEQ ID NO: 16)
ATCGTTTCATAAGCGCGCGAGGTCCAGCTGGTGCAGTC BssHII.HuVH3.A:
                                        (SEQ ID NO: 17)
ATCGTTTCATAAGCGCGCGAGGTGCAGCTGTTGGAGTC BssHII.HuVH3.B:
                                        (SEQ ID NO: 18)
ATCGTTTCATAAGCGCGCGAGGTGCAGCTGGTGGAGAC BssHII.HuVH4.A:
                                        (SEQ ID NO: 19)
ATCGTTTCATAAGCGCGCCAGGTGCAGCTACAGCAGTG VH Forward
NheI.JH 2:
                                        (SEQ ID NO: 20)
GACATTCTACGAGCTAGCTGAGGAGACAGTGACCAGGGT NheI.JH1/4/5:
                                        (SEQ ID NO: 21)
GACATTCTACGAGCTAGCTGAGGAGACGGTGACCAGGGT NheI.JH3:
                                        (SEQ ID NO: 22)
GACATTCTACGAGCTAGCTGAAGAGACGGTGACCATTGTC NheI.JH6:
                                        (SEQ ID NO: 23)
GACATTCTACGAGCTAGCTGAGGAGACGGTGACCGTGG VK Back
NheI.OL.HuVK1:
                                        (SEQ ID NO: 24)
TCTCCTCAGCTAGCGGTGGCGGCGGTTCCGGAGGTGGTGGTTCTGGCGGT
GGTGGCAGCGACATCCAGWTGACCCAGTC NheI.OL.HuVK2:
                                        (SEQ ID NO: 25)
TCTCCTCAGCTAGCGGTGGCGGCGGTTCCGGAGGTGGTGGTTCTGGCGGT
GGTGGCAGCGATGTTGTGATGACTCAGTC
```

NheI.OL.HuVK3:
(SEQ ID NO: 26)
TCTCCTCAGCTAGCGGTGGCGGCGGTTCCGGAGGTGGTGGTTCTGGCGGT

GGTGGCAGCGAAATTGTGWTGACRCAGTC

NheI.OL.HuVK4:
(SEQ ID NO: 27)
TCTCCTCAGCTAGCGGTGGCGGCGGTTCCGGAGGTGGTGGTTCTGGCGGT

GGTGGCAGCGATATTGTGATGACCCACAC

NheI.OL.HuVK5:
(SEQ ID NO: 28)
TCTCCTCAGCTAGCGGTGGCGGCGGTTCCGGAGGTGGTGGTTCTGGCGGT

GGTGGCAGCGAAACGACACTCACGCAGTC

NheI.OL.HuVK6:
(SEQ ID NO: 29)
TCTCCTCAGCTAGCGGTGGCGGCGGTTCCGGAGGTGGTGGTTCTGGCGGT

GGTGGCAGCGAAATTGTGCTGACTCAGTC

VK Forward
NcoI.JK1-:
(SEQ ID NO: 30)
AGTTCATGCCATGGTTTTGATTTCCACCTTGGTCCCTT

NcoI.JK2-:
(SEQ ID NO: 31)
AGTTCATGCCATGGTTTTGATCTCCACCTTGGTCCC

NcoI.JK3-:
(SEQ ID NO: 32)
AGTTCATGCCATGGTTTTGATATCCACTTTGGTCCCAG

NcoI.JK4-:
(SEQ ID NO: 33)
AGTTCATGCCATGGTTTTGATCTCCAGCTTGGTCCCT

NcoI.JK5-:
(SEQ ID NO: 34)
AGTTCATGCCATGGTTTTAATCTCCAGTCGTGTCCCTT

VL Back
NheI.OL.HuVL1.1:
(SEQ ID NO: 35)
TCTCCTCAGCTAGCGGTGGCGGCGGTTCCGGAGGTGGTGGTTCTGGCGGT

GGTGGCAGCCAGTCTGTG CTGACTCAGCC

NheI.OL.HuVL1.2:
(SEQ ID NO: 36)
TCTCCTCAGCTAGCGGTGGCGGCGGTTCCGGAGGTGGTGGTTCTGGCGGT

GGTGGCAGCCAGTCTGTG YTGACGCAGCC

NheI.OL.HuVL1.3:
(SEQ ID NO: 37)
TCTCCTCAGCTAGCGGTGGCGGCGGTTCCGGAGGTGGTGGTTCTGGCGGT

GGTGGCAGCCAGTCTGTC GTGACGCAGCC

NheI.OL.HuVL2:
(SEQ ID NO: 38)
TCTCCTCAGCTAGCGGTGGCGGCGGTTCCGGAGGTGGTGGTTCTGGCGGT

GGTGGCAGCCARTCTGCC CTGACTCAGCC

NheI.OL.HuVL3.1:
(SEQ ID NO: 39)
TCTCCTCAGCTAGCGGTGGCGGCGGTTCCGGAGGTGGTGGTTCTGGCGGT

GGTGGCAGCTCCTATGWG CTGACTCAGCC

NheI.OL.HuVL3.2:
(SEQ ID NO: 40)
TCTCCTCAGCTAGCGGTGGCGGCGGTTCCGGAGGTGGTGGTTCTGGCGGT

GGTGGCAGCTCTTCTGAG CTGACTCAGGA

NheI.OL.HuVL4:
(SEQ ID NO: 41)
TCTCCTCAGCTAGCGGTGGCGGCGGTTCCGGAGGTGGTGGTTCTGGCGGT

GGTGGCAGCCACGTTATA CTGACTCAACC

NheI.OL.HuVL5:
(SEQ ID NO: 42)
TCTCCTCAGCTAGCGGTGGCGGCGGTTCCGGAGGTGGTGGTTCTGGCGGT

GGTGGCAGCCAGGCTGTG CTGACTCAGCC

NheI.OL.HuVL6:
(SEQ ID NO: 43)
TCTCCTCAGCTAGCGGTGGCGGCGGTTCCGGAGGTGGTGGTTCTGGCGGT

GGTGGCAGCAATTTTATG CTGACTCAGCC

NheI.OL.HuVL7/8:
(SEQ ID NO: 44)
TCTCCTCAGCTAGCGGTGGCGGCGGTTCCGGAGGTGGTGGTTCTGGCGGT

GGTGGCAGCCAGRCTGTG GTGACYCAGGA

NheI.OL.HuVL9:
(SEQ ID NO: 45)
TCTCCTCAGCTAGCGGTGGCGGCGGTTCCGGAGGTGGTGGTTCTGGCGGT

GGTGGCAGCCWGCCTGTG CTGACTCAGCC

VL Forward
NcoI.JL1-:
(SEQ ID NO: 46)
AGTTCATGCCATGGTTAGGACGGTGACCTTGGTCC

NcoI.JL2/3-:
(SEQ ID NO: 47)
AGTTCATGCCATGGTTAGGACGGTCAGCTTGGTCC

NcoI.JL7-:
(SEQ ID NO: 48)
AGTTCATGCCATGGTGAGGACGGTCAGCTGGGTG

The resulting amplified cDNA products were assembled to scFv using overlap PCR with the following overlap primers.

(SEQ ID NO: 49)
BssE111.VH.OL+: ATCGTTTCATAAGCGCGCSA (SEQ ID NO: 50)
NotI.JK.OL-: AGTTCATGCCATGGTTTTGAT (SEQ ID NO: 51)
NotI.JLOL-: AGTTCATGCCATGGTKAGGAC

Purified scFv cDNA fragments (1 μg) and phagemid vector p2056BNN (2 μg) were digested with BssHII and NcoI restriction endonuclease (New England Biolabs, USA). Phagemid vector p2056BNN is a modified version of pS2025e (Sidhu et al., (2004) J Mol Biol 338:299-310), engineered to contain BssHII, NheI, and NcoI restriction sites. The scFv cDNA fragments were then ligated into the p2056BNN vector (6:1 M ratio) using T4 DNA ligase enzyme (New England Biolabs). The resulting cDNA/phage ligation products were purified using a PCR purification kit (Qiagen, USA) and transformed into electro-competent SS320 E. coli cells. The size of the phage library was estimated by plating 10 μl of 1:10 diluted library culture onto LB/Carbenicillin plates. The library culture was then further amplified and propagated in a total volume of 60 ml 2YT medium, and phage-scFv expression was induced by co-infection with M13KO7 helper phage. Kanamycin was later added to the library culture, and incubated with shaking for 30 hours at 30° C. The library culture was then centrifuged to pellet the cells. The phage-scFv-containing supernatant was precipitated with 5×PEG/2.5 M NaCl and resuspended in PBS.

Phage Library Sorting and Screening to Identify Anti-Hemagglutinin Antibodies

Figure 1B:
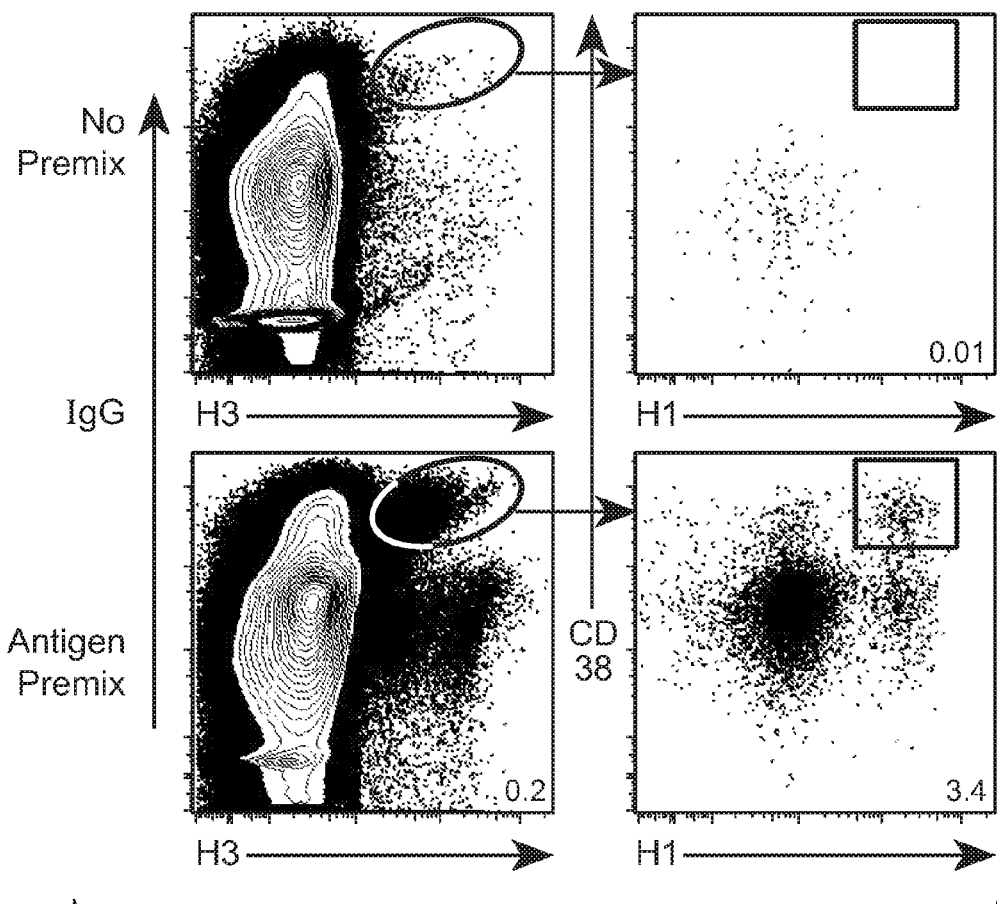
Figure 2:
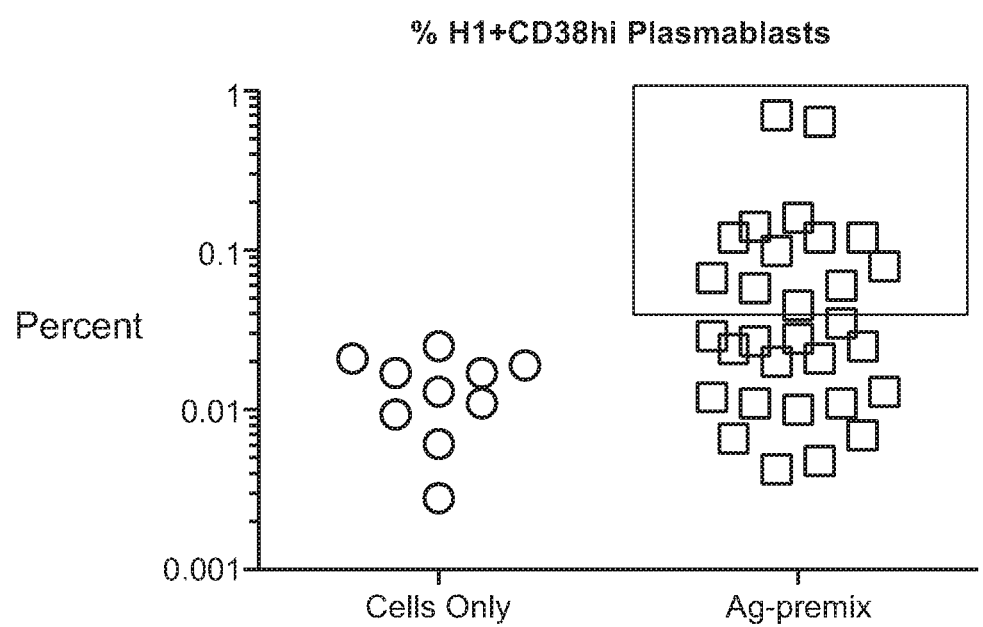
FIG. 2 sets forth data showing analysis of splenocytes obtained from day 8 post-intrasplenic implantation of PBMCs from individual SCID/beige mice with no PBMC/antigen premix (circles) and with PBMC/antigen premix (squares), as percent hemagglutinin $(H1)^+/CD38^{high}$ plasmablasts. The rectangle indicates mice that presented hemagglutinin H1+ plasmablasts.

Influenza A virus hemagglutinin H1 and H3 proteins (produced as described below in Example 2) were used as antigens for phage library sorting. Hemagglutinin H1 and H3 antigens were coated onto a high-binding 96-well max-isorp plate. The plates and phage libraries were pre-blocked with phage blocking buffer (phosphate-buffered saline (PBS), 1% (w/v) bovine serum albumin (BSA), and 0.05% (v/v) tween-20 (PBS-T)) and incubated for 2 hours at room temperature. The blocked phage library (100 μl) was added to the hemagglutinin-coated wells and incubated for 3 hours. The unbound phage were washed off the plates using 0.05% PBS-Tween, and bound phage were eluted with 100 μL 50 mM HCl and 500 mM NaCl for 30 minutes followed by neutralization with 100 μL of 1 M Tris base (pH 7.5). Recovered phage were amplified in *E. coli* XL-1 Blue cells. The resulting phage were precipitated and subjected another round of panning/selection against the hemagglutinin proteins. During subsequent panning/selection rounds, antibody phages were incubated with same or different hemagglutinin antigens. The stringency of plate washing was gradually increased from washing 15× to washing 40×.

After 2-3 rounds of panning and selection, significant enrichment of hemagglutinin-specific phage was observed. 96 phage clones were picked from the library sorting to determine whether they specifically bound to hemagglutinin H1 and/or H3. The variable regions of the phage clones displaying specific binding to the hemagglutinin proteins were sequenced to identify phage clones containing unique immunoglobulin nucleic acid sequences. Unique phage antibodies that bound hemagglutinin H1 and/or H3 with at least 5× above background were further characterized. Phage-derived clones of interest were reformatted into IgGs by cloning $V_L$ and $V_H$ regions of individual clones into the LPG3 and LPG4 expression vectors, respectively, transiently expressed in mammalian 293 cells, and purified using a protein A column. Two antibodies (mAb9 and mAb23) were identified for further analysis. (See Example 5 below.)

Example 2. Plasmablast Enrichment and Expansion

To discover and identify rare antibodies against influenza A virus hemagglutinin, the following plasmablast enrichment and expansion technique was developed. (See U.S. patent application Ser. No. 61/725,764, which is incorporated by reference herein in its entirety.)

Leukopacs from normal human donors that received the seasonal influenza Fluvirin® vaccine (Novartis Lot #111796P1) 7 days prior to their blood donation were obtained from Blood Centers of the Pacific (San Francisco, Calif.). Peripheral blood mononuclear cells (PBMCs) were isolated from the leukopacs using standard methodologies. Six- to eight-week old female SCID/beige mice were purchased from Charles River Laboratories (Hollister, Calif.) and housed and maintained at Genentech in accordance with American Association of Laboratory Animal Care guidelines. All experimental studies were conducted under the approval of the Institutional Animal Care and Use Committees of Genentech Lab Animal Research in an AAALACi-accredited facility in accordance with the Guide for the Care and Use of Laboratory Animals and applicable laws and regulations. Leukopac or blood from healthy human donors was obtained after written informed consent was provided and ethical approval granted from the Western Institutional Review Board.

In vivo antigen-driven plasmablast enrichment and expansion was performed using intraspenic transplantation of PBMCs as follows. Isolated PBMCs were resuspended with hemagglutinin antigens (0.1-2 μg for each one million B cells) and incubated for 30 minutes at 37° C. (PBMC/antigen pre-mix). Following this incubation, the PBMCs were washed to remove unbound antigens. To enrich for plasmablasts that produced cross-reactive hemagglutinin antibodies, the hemagglutinin antigen variants used for PBMC/antigen pre-mix and single cell sorting were specifically chosen to differ from the hemagglutinin antigen variants contained within the influenza Fluvirin® vaccine. Hemagglutinin antigens used in this study, therefore, included H1 hemagglutinin from influenza A virus isolate A/NWS/1933 (a Group1 influenza A virus hemagglutinin), H3 hemagglutinin from influenza A virus isolate A/Hong Kong/8/1968 (a Group2 influenza A virus hemagglutinin), and H7 hemagglutinin from influenza A virus isolate A/Netherlands/219/2003 (a Group2 influenza A virus hemagglutinin). The hemagglutinin antigens were produced at Genentech using standard molecular biology techniques.

6-8 week old female SCID/beige mice (Charles River Laboratories, Hollister, Calif.) were sub-lethally irradiated with 350 rads using a Cesium-137 source. Polymyxin B (110 mg/L) and neomycin (1.1 g/L) were added to the drinking water for 7 days following irradiation. Four hours after irradiation, the left flank of each mouse was shaved and prepped with Betadine® (Purdue Pharma, Stamford, Conn.) and 70% alcohol. Surgical procedures were performed under anesthesia using aseptic surgical procedures. A 1-cm skin incision was made just below the costal border of each mouse, followed by an incision of the abdominal wall and the peritoneum. The spleen of each mouse was carefully exposed and injected with $50\times10^6$ human PBMCs resuspended in 30 μL PBS. The incisions were closed in the muscular layer and in the skin using 5-O Vicryl® sutures (Ethicon, Somerville, N.J.) and surgical staples, respectively. For antigen-specific cell sorting experiments, mice were sacrificed at 8 days post-transplantation, and their spleens harvested.

Single cell suspensions of spleen cells obtained from the mice were stained with a cocktail of anti-human monoclonal antibodies CD38 PECy7 (BD Biosciences, San Jose, Calif.) and IgG Dylight (Jackson ImmunoResearch Laboratories, Inc., West Grove, Pa.) which define human IgG+ plasmablasts as $CD38^{high}$/IgG+ expression. To identify hemagglutinin cross-reactive plasmablasts within the suspension of isolated spleen cells, the cells were stained with hemagglutinin H1 from influenza virus A isolate A/WS/1933 and hemagglutinin H3 from influenza virus A isolate A/Hong Kong/8/1968, which were previously conjugated with FITC or PE, respectively, using Lightning-Link® labeling kits (Innova Biosciences, Cambridge, UK).

FIG. 1A shows representative FACS data analysis of anti-hemagglutinin-positive plasmablasts from day 7 post-vaccinated PBMCs prior to SCID/beige mice enrichment (i.e., prior to PBMC/antigen pre-mix). FIG. 1B shows representative FACS data analysis of hemagglutinin-positive plasmablasts from day 8 post-transplant after SCID/beige mice enrichment, comparing no pre-mix and antigen pre-mix in the upper and lower panels, respectively. As shown in FIGS. 1A and 1B, PBMC/antigen pre-mix prior to intrasplenic injection resulted in higher frequency of H3$^+$/H1$^+$ anti-hemagglutinin plasmablasts.

Table 2 below shows a comparison of anti-H1$^+$/anti-H3$^+$ plasmablast frequencies before and after SCID enrichment as described herein. As shown in Table 2, the frequency of anti-H1$^+$/anti-H3$^+$ plasmablasts was greatly increased using the SCID/beige mouse enrichment methods of the present invention compared to that observed without SCID/beige mouse enrichment.

TABLE 2

| Condition | Anti-H1$^+$/Anti-H3$^+$ Plasmablast Frequency (%) |
| --- | --- |
| Vaccinated PBMC | 0.00028 ± 0.00008 |
| SCID + Antigen Premix | 0.011 ± 0.007 |

Samples were then analyzed in the presence of propidium iodide dead cell exclusion on Aria high-speed cell sorter (BD Biosciences, San Jose, Calif.) and anti-hemagglutinin-specific plasmablasts were sorted in a single cell manner into 96-well tissue culture plates containing 50 μl RPMI cell cutlute media supplemented with 5% Low IgG fetal bovine serum. (Gibco, Grand Island, N.Y.).

Five million live cells were recorded for all analysis profiles. Profiles were analyzed by Flowjo version 9.4.11 software.

FIG. 2 shows analysis of splenocytes obtained from day-8 post-transplant from individual SCID/beige mice showing stochastic response, comparing no pre-mix (circles) and antigen-pre-mix (squares). Data is presented as percent anti-$H1^+/CD38^{high}$ plasmablasts. The rectangle indicates mice that presented anti-$H1^+$ plasmablasts.

These results showed that broad hemagglutinin cross-reactive plasmablasts were detected if influenza virus A Group1 (e.g., hemagglutinin H1) and Group2 (e.g., hemagglutinin H3, hemagglutinin H7) hemagglutinin antigens were incubated with PBMCs prior to intrasplenic transplant. These results further indicated that in vitro stimulation of hemagglutinin antigen-primed PBMCs from influenza-vaccinated donors promoted hemagglutinin antigen-specific enrichment of plasmablasts within the SCID/beige mouse recipients.

Example 3. IgG Cloning from Single Plasmablasts

Hemagglutinin H1 and H3 cross-reactive human plasmablasts (described above) were single-cell sorted, resulting in approximately 950 plasmablasts. Single plasmablasts were sorted directly into U-bottom 96-well micro-well plates containing 50 μl RPMI containing 5% Low IgG fetal bovine serum. The plates were centrifuged for 5 minutes at 600×g (Beckman Coulter, Brea, Calif.) and the media was carefully removed by aspiration. The cells were re-suspended and washed twice in 90 μl of PBS following the same procedure.

To generate cDNA encoding the variable heavy chains and light chains, each cell was re-suspended in 6 μl of Reverse Transcriptase (RT) reaction mixture containing 2 units RNaseout (Invitrogen, Grand Island, N.Y.), 0.5 mM 4dNTP (Perkin Elmer, Waltham, Mass.), 1.5 mM $MgCl_2$, 37.5 mM KCl, 10 mM DTT (dithiothreitol), 0.25% Nonidet P40 (US Biological, Marblehead, Mass.), 0.1 mg/ml bovine serum albumin (Sigma-Aldrich), 25 mM Tris pH 8.3, 0.25 pmol of $IgG_{1-4}$ constant, kappa chain constant, and lambda chain constant region specific oligonucleotides (shown below) and 40 U Superscript III (Invitrogen, Grand Island, N.Y.).

```
                                   (SEQ ID NO: 52)
IgG1-4 constant:     GAAGTAGTCCTTGACCAGGCAG (SEQ ID NO: 53)
Kappa constant:      CTCAGCGTCAGGGTGYTGCTGAG (SEQ ID NO: 54)
Lambda constant:     GGGTKTGGTSGTCTCCAC
```

The reaction was incubated for 3×30-minute intervals at 45° C., 50° C., and 55° C. each. Following the incubation, the reaction mixture was diluted to 15 μl with TE buffer (10 mm Tris HCl, 1 mM EDTA). Initial polymerase chain reactions (PCR) were performed to amplify IgG heavy chains, kappa chains, and lambda chains using 2 μl of the diluted RT cocktail from above and Advantage-GC 2 Polymerase Mix (Clontech, Mountain View, Calif.), following protocols provided by the manufacturers. The PCR amplifications were performed using degenerate oligonucleotides based on variable heavy chain and light chain germline and constant region sequences shown below.

```
                                              (SEQ ID NO: 55)
IGVH1a              CAGGTGCAGCTGGTGCAGTCTGGGGC (SEQ ID NO: 56)
IGVH1b              CAGGTCCAGCTGGTGCAGTCTGGGGC (SEQ ID NO: 57)
IGVH2               CAGGTCACCTTGAAGGAGTCTGGTCC (SEQ ID NO: 58)
IGVH3               GAGGTGCAGCTGGTGGAGTCTGGGGG (SEQ ID NO: 59)
IGVH4               CAGGTGCAGCTGCAGGAGTCGGGCCC (SEQ ID NO: 60)
IGVH5               GAGGTGCAGCTGGTGCAGTCTGG (SEQ ID NO: 61)
IGVH6               CAGGTACAGCTGCAGCAGTCAGGTCC (SEQ ID NO: 62)
IGVH7               CAGGTGCAGCTGGTGCAATCTGG (SEQ ID NO: 63)
IGKV1               GHCATCCRGWTGACCCAGTCTC (SEQ ID NO: 64)
IGKV2               GATRTTGTGATGACYCAGWCTC (SEQ ID NO: 65)
IGKV3               GAAATWGTRWTGACRCAGTCTC (SEQ ID NO: 66)
IGKV4               GACATCGTGATGACCCAGTCTCC (SEQ ID NO: 67)
IGKV5               GAAACGACACTCACGCAGTCTC (SEQ ID NO: 68)
IGKV6               GAWRTTGTGMTGACWCAGTCTC (SEQ ID NO: 69)
IGLV1               CAGTCTGTGYTGACKCAGCCRCCCTC (SEQ ID NO: 70)
IGLV2               CAGTCTGCCCTGACTCAGCCT
```

| | (SEQ ID NO: 71) |
|---|---|
| IGLV3 | TCCTATGAGCTGACWCAGSHVCCCKC |

| | (SEQ ID NO: 72) |
|---|---|
| IGLV4 | CAGCCTGTGCTGACTCARTCVCCCTC |

| | (SEQ ID NO: 73) |
|---|---|
| IGLV5 | CAGCCTGTGCTGACTCAGCCAACTTC |

| | (SEQ ID NO: 74) |
|---|---|
| IGLV6 | AATTTTATGCTGACTCAGCCCCAC |

| | (SEQ ID NO: 75) |
|---|---|
| IGLV7 | CAGGCTGTGGTGACTCAGGAGCCC |

| | (SEQ ID NO: 76) |
|---|---|
| IGLV8 | CAGACTGTGGTGACCCAGGAGCC |

| | (SEQ ID NO: 77) |
|---|---|
| IGLV9 | CAGCCTGTGCTGACTCAGCCACC |

| | (SEQ ID NO: 78) |
|---|---|
| HC301.5constant | GCAGCCCAGGGCSGCTGTGC |

| | (SEQ ID NO: 79) |
|---|---|
| Kappa102constant | GCACACAACAGAGGCAGTTCCAG |

| | (SEQ ID NO: 80) |
|---|---|
| Lambda202constant | CTTGRAGCTCCTCAGAGGAG |

Heavy chain and light chain PCR amplification reactions were each divided into two reactions as follows: heavy chain families VH.1,2,3 (primers IGVH1a, IGVH1b, IGVH2, IGVH3) and VH.4,5,6,7 (primers IGVH4, IGVH5, IGVH6, and IGVH7); kappa chain families VK.1,2,3 (primers IGKV1, IGKV2, and IGKV3) and VK.4,5,6 (primers IGVK4, IGVK5, and IGVK6); and lambda chain families VL.1,2,3,4,5 (IGLV1, IGLV2, IGLV3, IGLV4, and IGLV5) and VL.6,7,8,9 (primers IGLV6, IGLV7, IGLV8, and IGLV9). A touchdown PCR amplification protocol was used for temperature cycling.

Following the reaction, PCR amplification products were treated with Exonuclease1 (Exo) and Shrimp Alkaline Phosphatase (SAP) to remove excess nucleotides and primers from each of the PCR amplification reactions (U.S. Biologicals, Marblehead, Mass.). Initial PCR amplification products were directly sequenced to determine the variable sequences of both the heavy chains and light chains using Sanger sequencing. Second nested PCR amplifications were performed using germline-matched heavy chain and light chain variable oligonucleotides in order to insert a mammalian signal and constant region cloning sequences using the following oligonucleotide primers.

sVH1a:
(SEQ ID NO: 81)
CCACCATGGGATGGTCATGTATCATCCTTTTTCTAGTAGCAACTGCAACT
GGAGTACATTCACAGG sVH2:
(SEQ ID NO: 82)
CCACCATGGGATGGTCATGTATCATCCTTTTTCTAGTAGCAACTGCAACT
GGAGTACATTCACAGATCACCT sVH3vv:
(SEQ ID NO: 83)
CCACCATGGGATGGTCATGTATCATCCTTTTTCTAGTAGCAACTGCAACT
GGAGTACATTCACAG sVH3gL:
(SEQ ID NO: 84)
CCACCATGGGATGGTCATGTATCATCCTTTTTCTAGTAGCAACTGCAACT
GGAGTACATTCAGAGG sVH4:
(SEQ ID NO: 85)
CCACCATGGGATGGTCATGTATCATCCTTTTTCTAGTAGCAACTGCAACT
GGAGTACATTCACAGGTGCAGCTGCAGG sVH5:
(SEQ ID NO: 86)
CCACCATGGGATGGTCATGTATCATCCTTTTTCTAGTAGCAACTGCAACT
GGAGTACATTCAGAGGTGCA sVH6:
(SEQ ID NO: 87)
CCACCATGGGATGGTCATGTATCATCCTTTTTCTAGTAGCAACTGCAACT
GGAGTACATTCACAGGTACAGC sVH7:
(SEQ ID NO: 88)
CCACCATGGGATGGTCATGTATCATCCTTTTTCTAGTAGCAACTGCAACT
GGAGTACATTCACAGGTGCA sVK1:
(SEQ ID NO: 89)
CCACCATGGGATGGTCATGTATCATCCTTTTTCTAGTAGCAACTGCAACT
GGAGTACATTCAGACATCCAGATGACCCAGTCTCCATCCTCCCTG sVK2:
(SEQ ID NO: 90)
CCACCATGGGATGGTCATGTATCATCCTTTTTCTAGTAGCAACTGCAACT
GGAGTACATTCAGATATTGTGATGACTCAGTCTCACTCTCCCTGC sVK3:
(SEQ ID NO: 91)
CCACCATGGGATGGTCATGTATCATCCTTTTTCTAGTAGCAACTGCAACT
GGAGTACATTCAGAAATTGTGTTGACACAGTCTCCAGCCACCCTGTCTTT
G sVK4:
(SEQ ID NO: 92)
CCACCATGGGATGGTCATGTATCATCCTTTTTCTAGTAGCAACTGCAACT
GGAGTACATTCAGACATCGTGATGACCCAGTCTCCAGACTCCCTGGCTGT
G sVK5:
(SEQ ID NO: 93)
CCACCATGGGATGGTCATGTATCATCCTTTTTCTAGTAGCAACTGCAACT
GGAGTACATTCAGAAACGACACTCACGCAGTCTCCAGC sVK6:
(SEQ ID NO: 94)
CCACCATGGGATGGTCATGTATCATCCTTTTTCTAGTAGCAACTGCAACT
GGAGTACATTCAGAAATTGTGCTGACTCAGTCTCCAGACTTTCG sVL1:
(SEQ ID NO: 95)
CCACCATGGGATGGTCATGTATCATCCTTTTTCTAGTAGCAACTGCAACT
GGAGTACATTCACAGTCTGTGYTGACKCAGCCRCCCTC

-continued sVL2:
(SEQ ID NO: 96)
CCACCATGGGATGGTCATGTATCATCCTTTTTCTAGTAGCAACTGCAACT

GGAGTACATTCACAGTCTGCCCTGACTCAGCCT sVL3:
(SEQ ID NO: 97)
CCACCATGGGATGGTCATGTATCATCCTTTTTCTAGTAGCAACTGCAACT

GGAGTACATTCATCCTATGAGCTGACWCAGSHVCCCKC sVL4:
(SEQ ID NO: 98)
CCACCATGGGATGGTCATGTATCATCCTTTTTCTAGTAGCAACTGCAACT

GGAGTACATTCACAGCCTGTGCTGACTCARTCVCCCTC sVL5:
(SEQ ID NO: 99)
CCACCATGGGATGGTCATGTATCATCCTTTTTCTAGTAGCAACTGCAACT

GGAGTACATTCACAGCCTGTGCTGACTCAGCCAACTTC sVL6:
(SEQ ID NO: 100)
CCACCATGGGATGGTCATGTATCATCCTTTTTCTAGTAGCAACTGCAACT

GGAGTACATTCAAATTTTATGCTGACTCAGCCCCAC sVL7:
(SEQ ID NO: 101)
CCACCATGGGATGGTCATGTATCATCCTTTTTCTAGTAGCAACTGCAACT

GGAGTACATTCACAGGCTGTGGTGACTCAGGAGCCC sVL8:
(SEQ ID NO: 102)
CCACCATGGGATGGTCATGTATCATCCTTTTTCTAGTAGCAACTGCAACT

GGAGTACATTCACAGACTGTGGTGACCCAGGAGCC wVL9:
(SEQ ID NO: 103)
CCACCATGGGATGGTCATGTATCATCCTTTTTCTAGTAGCAACTGCAACT

GGAGTACATTCACAGCCTGTGCTGACTCAGCCACC

Heavy constant:
(SEQ ID NO: 104)
GCCAGGGGGAAGACCGATG

Kappa constant:
(SEQ ID NO: 105)
CTGGGATAGAAGTTATTCAGCAGGCACACAACAGAAGCAGTTCCAGATTT

CAACTGCTC

Lambda constant:
(SEQ ID NO: 80)
CTTGRAGCTCCTCAGAGGAG

PCR amplification reactions were set up using PrimeStar HS DNA Polymerase with GC (Takara Bio, Shiga, Japan) according to the manufacturer's recommendation. Following the PCR amplification reactions, the amplification products were treated with Exo/SAP as described above. Heavy variable chain and light variable chain encoding PCR amplification products were inserted into a mammalian expression vector using restriction endonuclease free procedures. 20 µl of the PCR amplification products were annealed onto single stranded DNA human templates for IgG$_1$, kappa, and lambda chain using the Kunkel mutagenesis protocol. (See Kunkel (1985) PNAS 82:488-492.) Correctly inserted constructs were confirmed by DNA sequencing. Plasmids containing nucleic acids encoding heavy chains and light chains were co-transfected into 293T human embryonic kidney cells using Fugene transfection reagent (Roche Diagnostic, Indianapolis, Ind.) for transient expression, and analyzed for expression and binding as described below in Example 4.

Example 4. Hemagglutinin ELISA Screening Assay

The ability of each monoclonal anti-hemagglutinin antibody obtained as described above to bind various hemagglutinin subtypes was examined by ELISA as follows. Various hemagglutinin-expressing plasmids were transfected into 293T cells as described above. These included hemagglutinin H1 from H1N1/South Carolina/1918, hemagglutinin H3 from H3N2/Perth/2009, hemagglutinin H5 from H5N1/Viet/2004, and hemagglutinin H7 from H7N7/Netherlands/2003 influenza A viruses. After two days, cells were lysed in 50 mM Tris, pH 8, 5 mM EDTA, 150 mM NaCl, 1% Triton X-100 plus protease inhibitor cocktail (Roche). Nuclei were cleared by centrifugation and the resulting lysates were stored at −80° C.

For ELISA screening, 384-well plates (Nunc MaxiSorp) were coated with 5 μg/ml Galanthus nivalis lectin (Sigma) in PBS. The plates were washed and then coated with dilutions of the cell lysates containing various expressed hemagglutinins. The plates were washed and incubated with various dilutions of the anti-hemagglutinin antibodies and subsequently with a goat-anti-human-HRP secondary antibody (Jackson). Plates were washed and processed for TMB (3,3',5,5'-tetramethylbenzidine) substrate detection.

Approximately 950 plasmablasts were obtained from single-cell sorting described above in Example 2. Of this, 840 monoclonal antibodies were transiently expressed in 293T cells and screened by ELISA for binding to hemagglutinin subtypes H1, H3, H5, and H7, resulting in 82 monoclonal antibodies that bound influenza A virus Group1 or Group2 hemagglutinin, and 20 monoclonal antibodies that bound both influenza A virus Group1 and Group2 hemagglutinins.

Example 5. In Vitro Influenza A Virus Neutralization

The ability of the anti-hemagglutinin antibodies of the present invention to elicit broad hemagglutinin subtype binding and neutralization of a panel of influenza A Group1 and Group2 virus isolates in vitro was examined as follows.

MDCK cells were grown in DMEM media supplemented with 10% FBS as a single 25% confluent monolayer in 96-well black with clear bottom imaging plates (Costar 3904). Each influenza A virus subtype/strain was diluted in influenza media (DMEM+0.2% BSA, 2 μg/ml TPCK treated Trypsin) to an MOI of 1 and incubated for 1 hour at 37° C. with varying concentrations (ranging from 0.02 nM to 1,600 nM) of each antibody. Each antibody/influenza virus mixture was allowed to infect MDCK cells for 16 hours at 37° C. in a 5% $CO_2$ incubator prior to fixation of the cells with cold 100% ethanol. The fixed cells were then stained with Hoechst 33342 (Invitrogen, Cat# H3570) to visualize cell nuclei and determine total cell number. The cells were also stained with a broadly reactive monoclonal antibody (Millipore Cat# MAB8258) specific for influenza A virus nucleoprotein in order to determine the number of infected cells.

Cells were imaged using the Image Express Micro (Molecular Devices) and data images were analyzed using MetaXpress 3.1 software. The percentage of infected cells was determined and plotted on the Y-axis versus the Log 10 antibody concentration on the X-axis. All neutralization assays were completed in triplicate. Data were fit using a nonlinear regression dose-response curve and are presented in FIG. 3 as $IC_{50}$ values in nM with 95% confidence intervals (95% CI). The hemagglutinin (HA) subtype of each influenza A virus strain is provided in the table shown in FIG. 3.

Figure 4A:
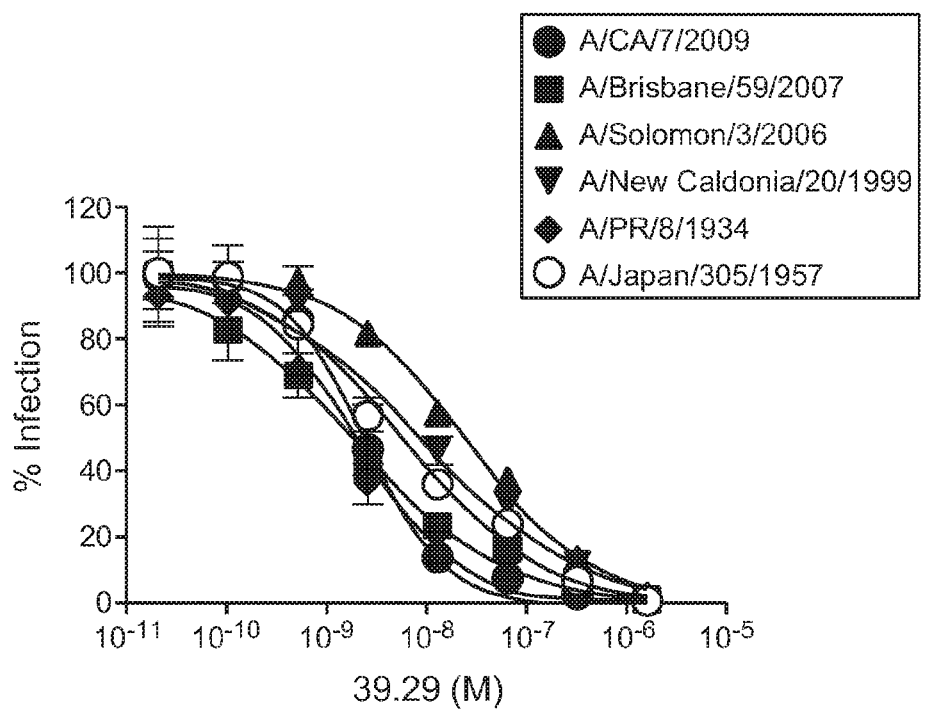
FIGS. 4A and 4B set forth data showing in vitro neutralization of various influenza A Group1 (FIG. 4A) and Group2 (FIG. 4B) virus strains by monoclonal antibody 39.29 NWPP ("NWPP" disclosed as SEQ ID NO: 177).
Figure 4B:
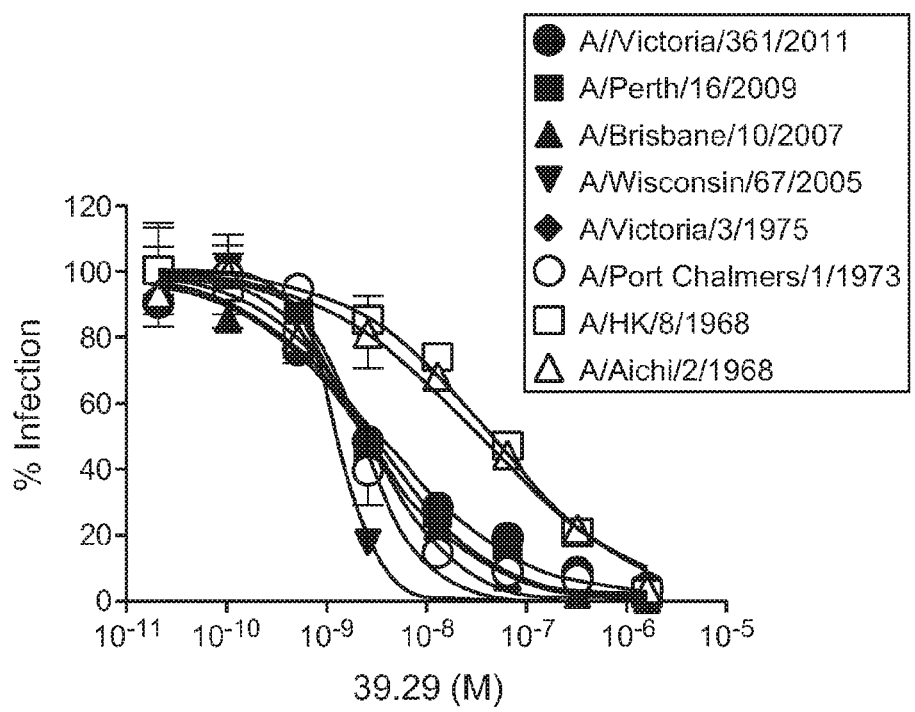
Figure 5A:
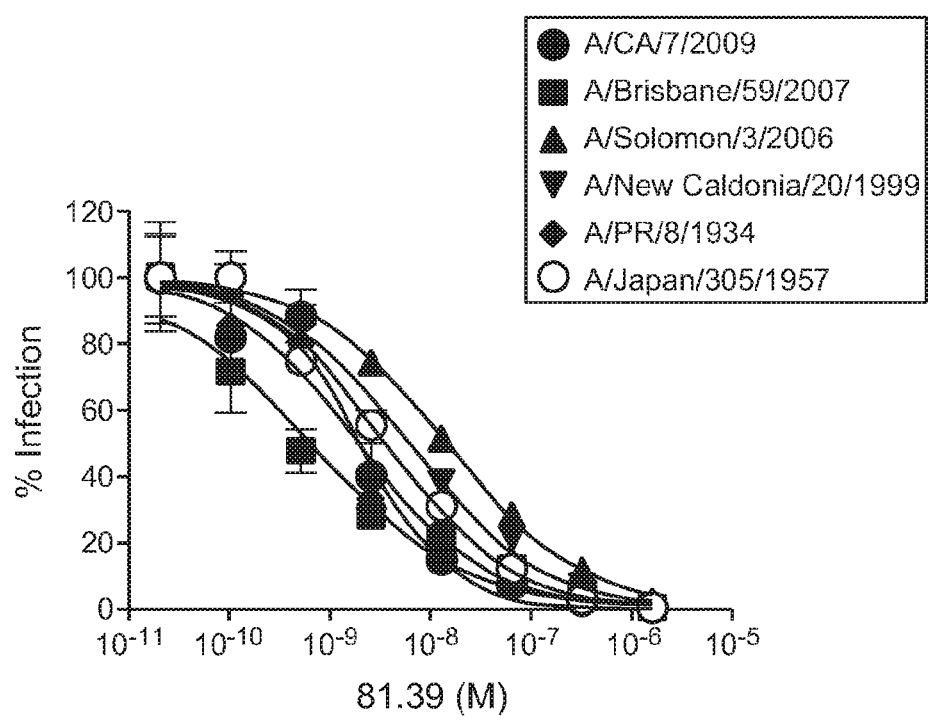
FIGS. 5A and 5B set forth data showing in vitro neutralization of various influenza A Group1 (FIG. 5A) and Group2 (FIG. 5B) virus strains by monoclonal antibody 81.39 SVSH-NYP ("SVSH" disclosed as SEQ ID NO: 171).
Figure 5B:
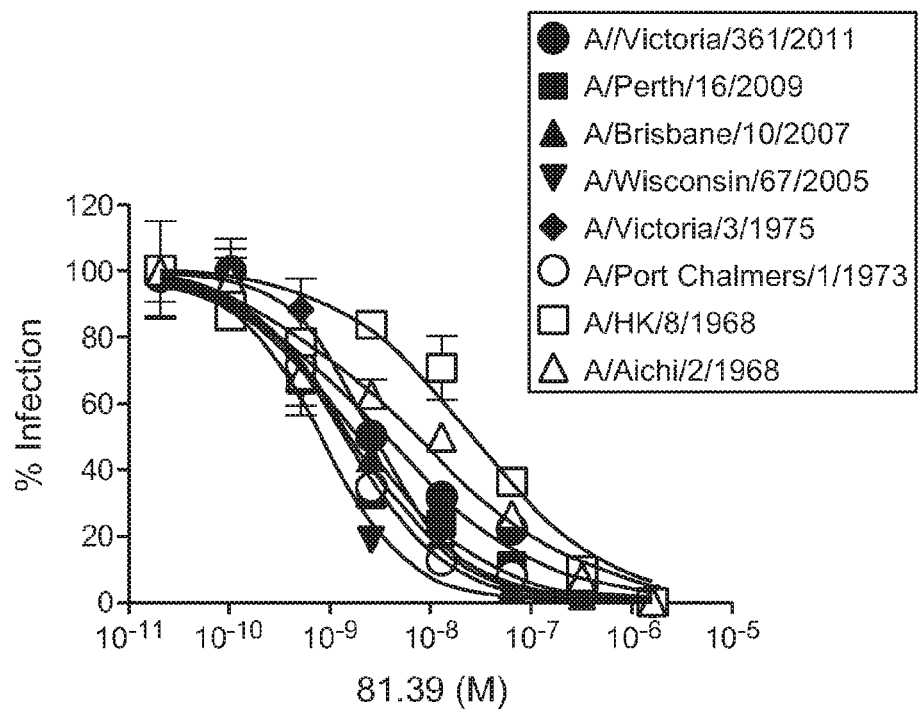

In vitro neutralization dose-response curves were generated using various concentrations of the monoclonal antibodies described herein against a broad panel of influenza A Group1 and Group2 virus strains. FIGS. 4A and 4B show neutralization curves of mAb 39.29 NWPP ("NWPP" disclosed as SEQ ID NO: 177) against a panel of influenza A Group1 and Group2 virus strains, respectively. As shown in FIGS. 4A and 4B, mAb 39.29 NWPP ("NWPP" disclosed as SEQ ID NO: 177) was effective at in vitro neutralization of all influenza A virus strains tested. (See also FIG. 3.) Additionally, FIGS. 5A and 5B show neutralization curves of mAb 81.39 SVSH-NYP ("SVSH" disclosed as SEQ ID NO: 171) against a panel of influenza A Group1 and Group2 virus strains, respectively. As shown in FIGS. 5A and 5B, mAb 81.39 SVSH-NYP ("SVSH" disclosed as SEQ ID NO: 171) was effective at the in vitro neutralization of all influenza A virus strains tested. (See also FIG. 3.)

Figure 6:
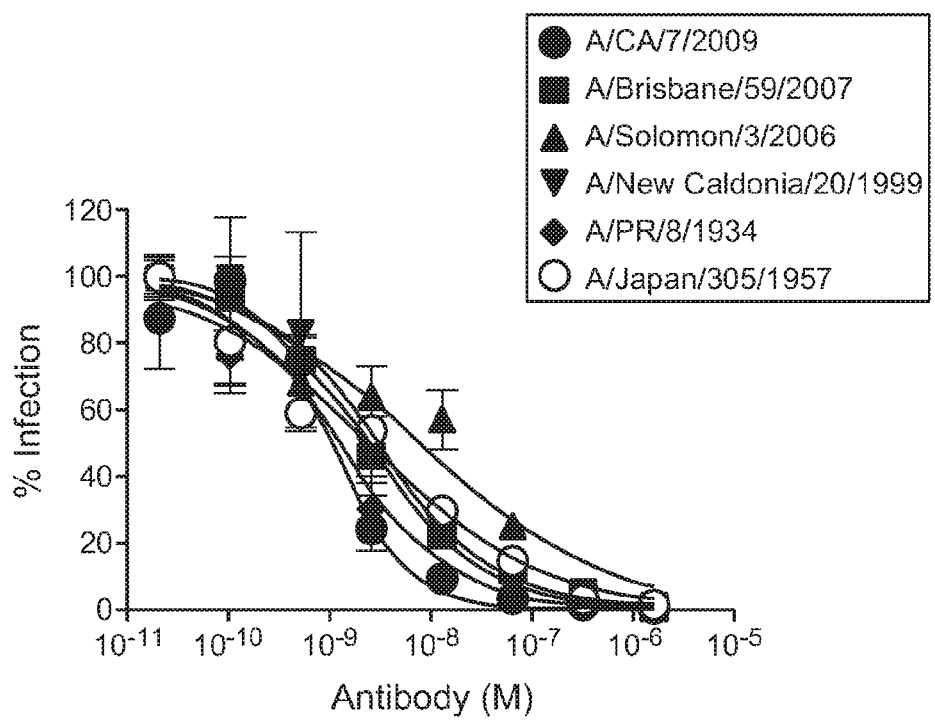
FIG. 6 sets forth data showing in vitro neutralization of various influenza A Group1 virus strains by monoclonal antibody 39.18 B11.
Figure 7:
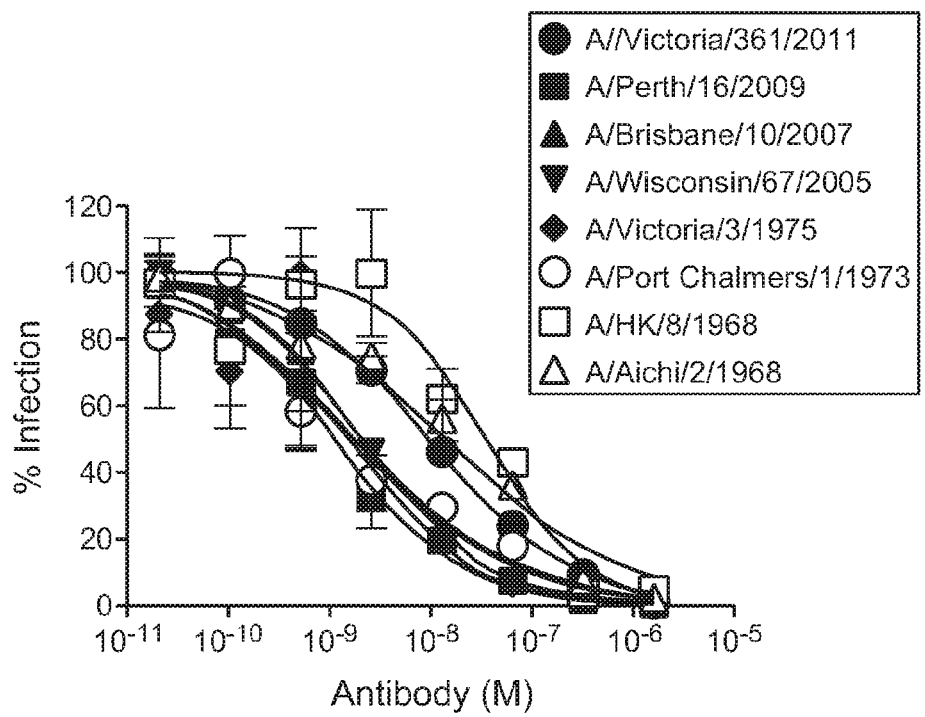
FIG. 7 sets forth data showing in vitro neutralization of various influenza A Group1 and Group2 virus strains by monoclonal antibody 36.89.
Figure 8:
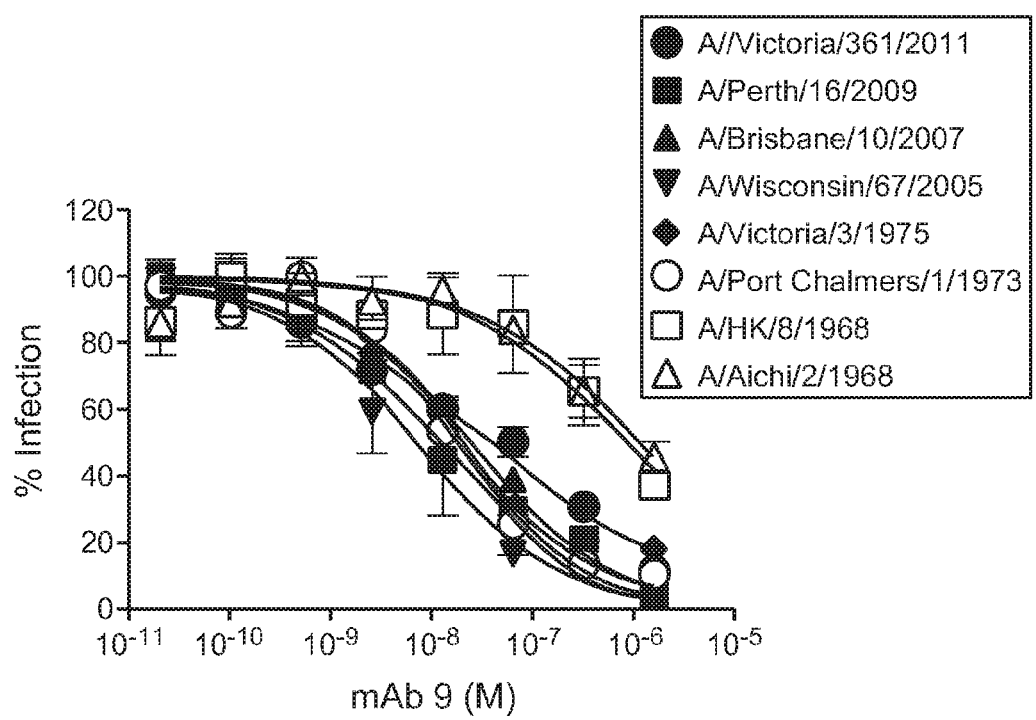
FIG. 8 sets forth data showing in vitro neutralization of various influenza A Group1 and Group2 virus strains by monoclonal antibody mAb9 01F3.
Figure 9:
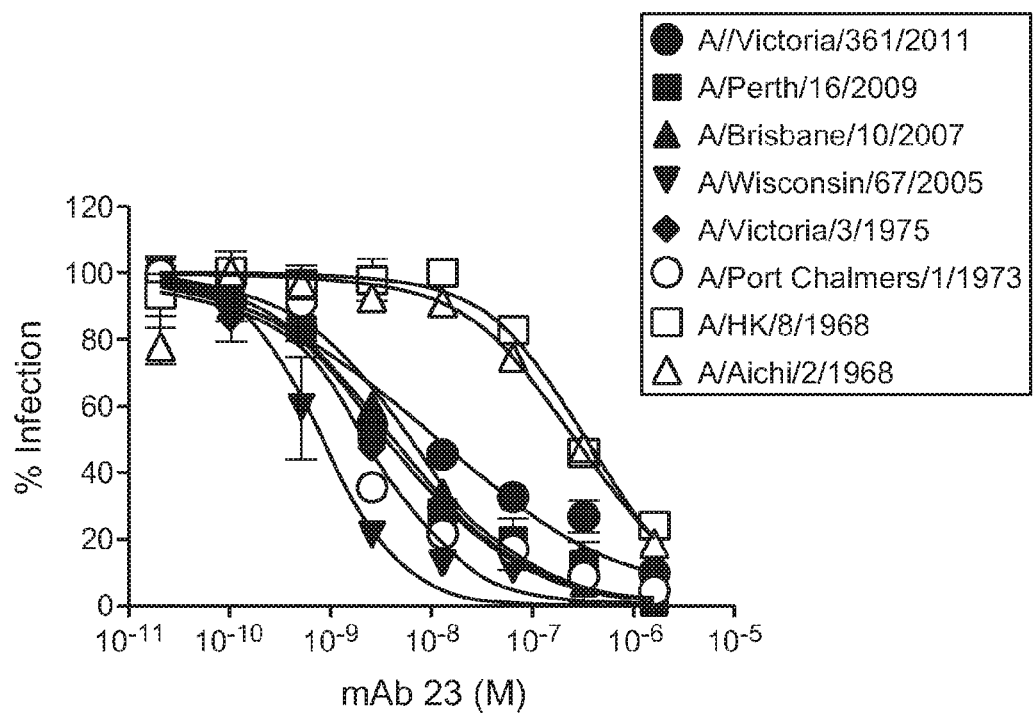
FIG. 9 sets forth data showing in vitro neutralization of various influenza A Group1 and Group2 virus strains by monoclonal antibody mAb23 06C2.

Four anti-hemagglutinin antibodies of the present invention (specifically mAb 39.18 B11, mAb 36.89, mAb9.01F3, and mAb23.06C2) were effective in vitro at neutralization of either Group1 or Group2 influenza A virus strains, but not both. Specifically, mAb 39.18 B11 was effective at in vitro neutralization of the entire Group1 influenza A virus panel examined, but was not able to neutralize Group2 influenza A virus strains. (See FIG. 6 and FIG. 3.) Conversely, mAb 36.89, mAb9.01F3, and mAb23.06C2 were able to neutralize the entire Group2 influenza A virus panel examined, but were not able to neutralize any Group1 influenza A virus isolate tested. (See FIGS. 7, 8, and 9, showing in vitro neutralization curves for mAb 36.89, mAb9.01F3, and mAb23.06C2, respectively; also see FIG. 3.)

Taken together, these results showed that monoclonal antibodies of the present invention were able to neutralize in a dose-dependent manner various influenza A virus isolates/strains in vitro. Additionally, these results showed that the plasmablast enrichment methodology described herein resulted in the identification of monoclonal antibodies capable of neutralizing both Group1 and Group2 influenza A virus strains from only 950 isolated plasmablasts.

In vitro neutralization studies were also performed using a pseudotype virus engineered to express hemagglutinin H5 to test the efficacy of an antibody of the present invention at neutralizing H5N1 influenza A virus. In particular, an HIV psueudotype virus bearing the H5 hemaggutinin surface protein was tested for neutralization with mAb 39.29 NCv1 on 293T cells as follows. The H5 pseudotype virus was produced by co-transfection of 293T cells with three plasmids: Δ8.9, FCMV-GFP, and a plasmid expressing hemagglutinin H5 from influenza A virus isolate H5N1/Vietnam/1203/2004. Virus was purified by ultra-centrifugation through 20% sucrose.

Figure 10:
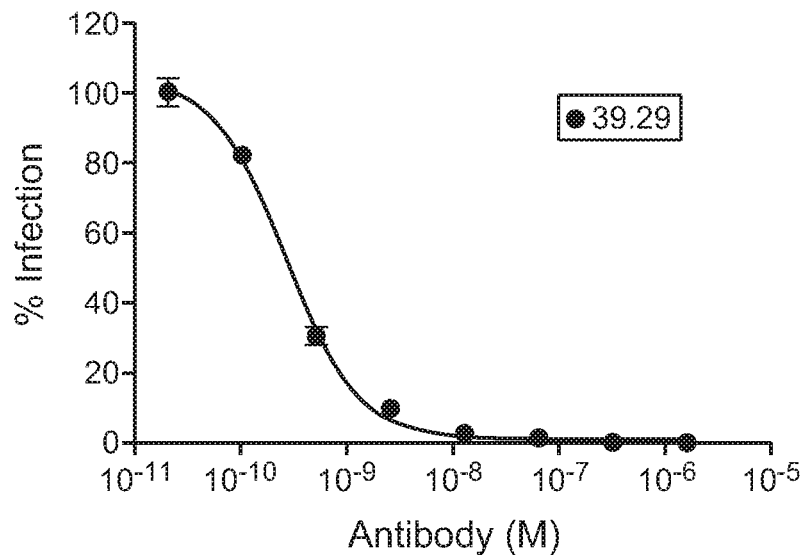
FIG. 10 sets forth data showing in vitro neutralization of an hemagglutinin H5-expressing pseudovirus by monoclonal antibody 39.29 NCv1.

For infection, pseudotype virus was incubated with various amounts of mAb 39.29 NCv1 before adding to target 293T cells cultured in 96-well plates. After two days, the number of infected cells was determined by counting GFP positive cells. Infection was normalized to the number of infected cells at the lowest antibody concentration used. The results are presented in FIG. 10. As shown in FIG. 10, mAb 39.29 NCv1 displayed a dose-dependent in vitro neutralization against the pseudotype virus expressing hemaggutinin H5 surface protein. These data suggested that antibodies of the present invention would be effective at treatment and prevention of H5N1 influenza A virus strains.

Figure 11:
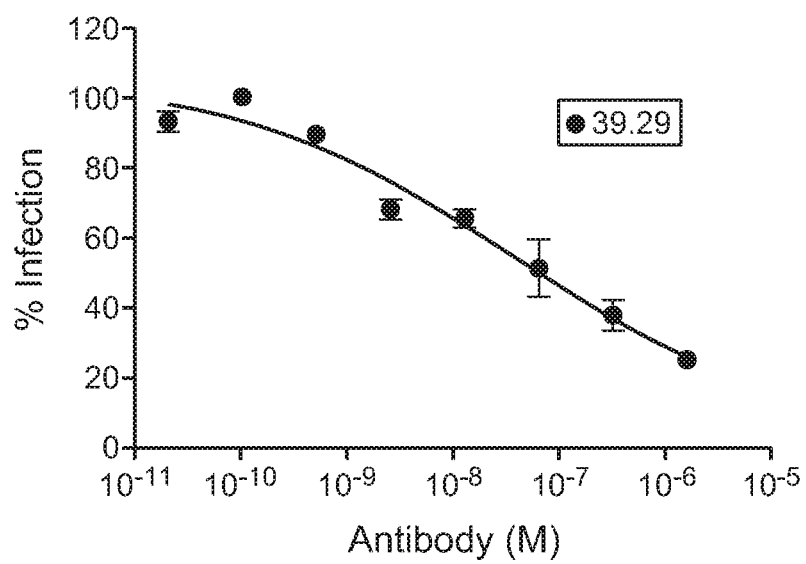
FIG. 11 sets forth data showing in vitro neutralization of an H7N7 equine influenza virus by monoclonal antibody 39.29 NWPP ("NWPP" disclosed as SEQ ID NO: 177).
Figure 12B:
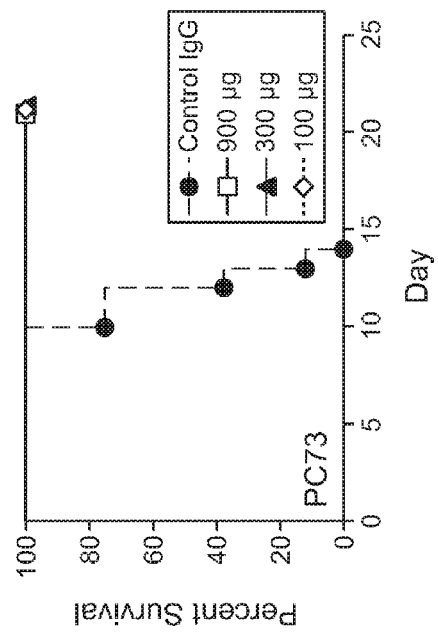
FIGS. 12A, 12B, 12C, and 12D set forth data showing percent survival of mice infected with various influenza A virus strains (A/PR/8/1934 (PR8), FIG. 12A; A/Port Chalmers/1/1973 (PC73), FIG. 12B; A/Hong Kong/1/1968 (HK68), FIG. 12C); and A/Aichi/2/1968 (Aichi68), FIG. 12D) and administered various amounts of monoclonal antibody 39.29 NWPP ("NWPP" disclosed as SEQ ID NO: 177).
Figure 12D:
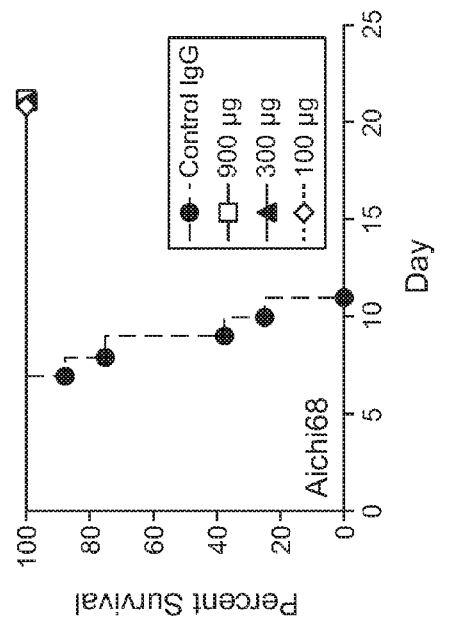
Figure 12A:
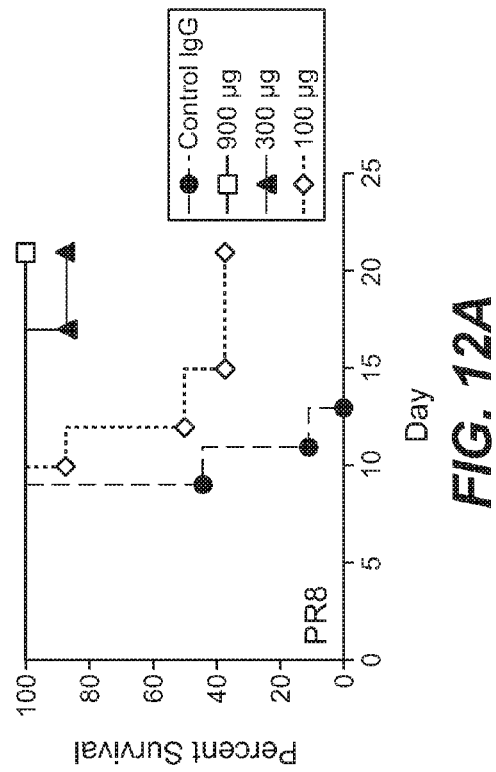
Figure 12C:
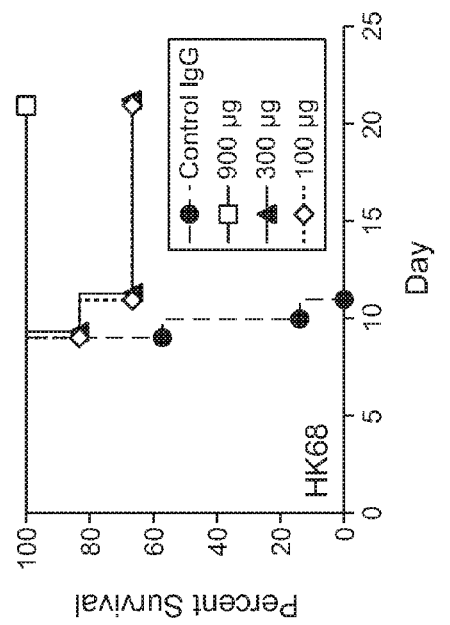

An equine influenza virus was also tested for the ability of antibodies of the present invention to exhibit in vitro neutralization activity as follows. H7N7 A/Equine/1/Prague/56 influenza A virus was passed on MDCK cells until it achieved a high degree of infectivity. The resulting H7N7 A/Equine/1/Prague/56 influenza A virus was used in neutralization assays (using methods as described above for mAb 39.29 NCv1) on MDCK cells. The results of these experiments are presented in FIG. 11. As shown in FIG. 11, mAb 39.29 NWPP ("NWPP" disclosed as SEQ ID NO: 177) displayed a dose-dependent in vitro neutralization against the H7N7 A/Equine/1/Prague/56 influenza virus expressing hemagglutinin H7 surface protein.

Taken together, these results showed that anti-hemagglutinin antibodies of the present invention exhibited dose-dependent neutralization activity against a variety of influenza A virus strains. Specifically, two anti-hemagglutinin antibodies (mAb 39.29 NWPP ("NWPP" disclosed as SEQ ID NO: 177) and mAb 81.39 SVSH-NYP ("SVSH" disclosed as SEQ ID NO: 171)) were effective at neutralizing all influenza A virus strains examined, including neutralization of both Group1 influenza A virus strains (A/CA/7/2009, A/Brisbane/59/2007, A/Solomon/3/2006, A/New Caledonia/20/1999, A/PR/8/1934, and A/Japan/305/1957) and Group2 influenza A virus strains (A/Victoria/361/2011, A/Perth/16/2009, A/Brisbane/10/2007, A/Wisconsin/67/2005, A/Victoria/3/1975, A/Port Chalmers/1/1973, A/HK/8/1968, and A/Aichi/2/1968).

Additionally, these results showed that anti-hemagglutinin antibodies of the present invention (e.g., mAb 39.29 NWPP ("NWPP" disclosed as SEQ ID NO: 177) (FIGS. 4A and 4B) and mAb 81.39 SVSH-NYP ("SVSH" disclosed as SEQ ID NO: 171) (FIGS. 5A and 5B)) were effective at neutralization of a variety of different seasonal H1N1 influenza A virus strains, H3N2 influenza A virus strains, a H2N2 influenza A virus strain, and the influenza A virus strain associated with the 1957 Japan pandemic (A/Japan/305/1957). These results indicated that antibodies of the present invention are effective in the treatment and prevention of seasonal influenza A virus infection and influenza A virus strains associated with influenza pandemics.

Example 6. In Vivo Efficacy of mAb 39.29 NWPP ("NWPP" Disclosed as SEQ ID NO: 177) in Mice The in vivo efficacy of mAb 39.29 NWPP ("NWPP" disclosed as SEQ ID NO: 177) to influenza A virus infection in mice was performed as follows. DBA/2J mice (Jackson Lab, Bar Harbor, Me.) were infected intranasally with 50 μl of various influenza A virus strains diluted in influenza media (DMEM, 0.2% BSA, 2 μg/mL TPCK-treated trypsin) at the minimum $LD_{100}$ dose. Four different influenza A virus strains exhibiting a range of in vitro $IC_{50}$ values were used in this series of experiments, including: H1N1 A/PR/8/1934 (Genentech; $IC_{50}$ 2.0 nM), used at 40 PFU per mouse; H3N2 A/Hong Kong/1/1968 (ViraPur, San Diego, Calif.; $IC_{50}$ 45.1 nM), used at 3 PFU per mouse; H3N2 A/Port Chalmers/1/1973 (ViraPur, San Diego, Calif.; $IC_{50}$ 2.2 nM), used at $1.5\times10^4$ PFU per mouse; and H3N2 A/Aichi/2/1968 (ViraPur, San Diego, Calif.; $IC_{50}$ 35 nM), used at $2\times10^2$ PFU per mouse. Influenza virus infection was allowed to progress for 72 hours prior to the intravenous administration of mAb 39.29 NWPP ("NWPP" disclosed as SEQ ID NO: 177).

After 72 hours post influenza virus A infection, various amounts of mAb 39.29 NWPP ("NWPP" disclosed as SEQ ID NO: 177) were administered intravenously to the mice at a dose of 900 µg/mouse (approximately 45 mg/kg), 300 µg/mouse (approximately 15 mg/kg), and 100 µg/mouse (approximately 5 mg/kg) in 200 µl PBS. Control treated animals were administered mAb gD5237 (a monoclonal antibody specific for glycoprotein D of herpes simplex virus (HSV)) at the highest tested equivalent dose of mAb 39.29 NWPP ("NWPP" disclosed as SEQ ID NO: 177) (i.e., approximately 45 mg/kg). Mice were monitored daily for body conditioning and survival, and also weighed daily, until 21 days after infection. All mAb39.29 NWPP ("NWPP" disclosed as SEQ ID NO: 177) doses vs. control in all four influenza A virus strain infections gave a Log-rank test of P<0.01.

FIGS. 12A, 12B, 12C, and 12D show percent survival (over time, in days) of mice administered various amounts of mAb 39.29 NWPP ("NWPP" disclosed as SEQ ID NO: 177) 72 hours after infection with influenza A virus A/PR/8/1934, A/Port Chalmers/1/1973, A/Hong Kong/1/1968, and A/Aichi/2/1968, respectively. As shown in FIGS. 12A, 12B, 12C, and 12D, 100% mortality was observed by day 14 in infected mice administered control antibody. However, infected mice administered monoclonal antibody of the present invention showed increased survival. In particular, 100% survival was observed in mice infected with influenza virus A/Port Chalmers/1/1973 or influenza virus A/Aichi/2/1968 at all doses of mAb 39.29 NWPP ("NWPP" disclosed as SEQ ID NO: 177) tested. (See FIGS. 12B and 12D.)

These results showed that monoclonal antibodies of the present invention are effective at treating various influenza A virus infections. Additionally, these data showed that monoclonal antibodies of the present invention were effective at treating influenza A virus infection when administered up to at least 72 hours post influenza A virus infection.

Example 7. In Vivo Efficacy of mAb 39.29 NCv1 in Mice

To test the in vivo efficacy of mAb 39.29 NCv1 in mice, the antibody was administered i.v. to mice infected with four different influenza A virus isolates that exhibited a range of in vitro $IC_{50}$ values. DBA/2J mice (Jackson Lab, Bar Harbor, Me.) were infected intranasally with 50 µl of different influenza A virus strains diluted into influenza media (DMEM, 0.2% BSA, 2 ug/mL TPCK treated trypsin) at the minimum LD100 dose.

In one set of experiments, influenza A virus isolate H1N1 A/PR/8/1934 was used at 40 PFU per mouse. At 72 hours post infection, anti-hemagglutinin mAb 39.29 NCv1 was administered intravenously at approximately 15 mg/kg, approximately 5 mg/kg, approximately 1.7 mg/kg, or approximately 0.56 mg/kg in 200 µl PBS intravenously. Control treated animals were given mAb gD5237, which is specific for glycoprotein D of HSV at the highest tested equivalent dose of mAb 39.29 NCv1. Mice were monitored for body conditioning and survival, and weighed until 21 days after infection.

Figure 13:
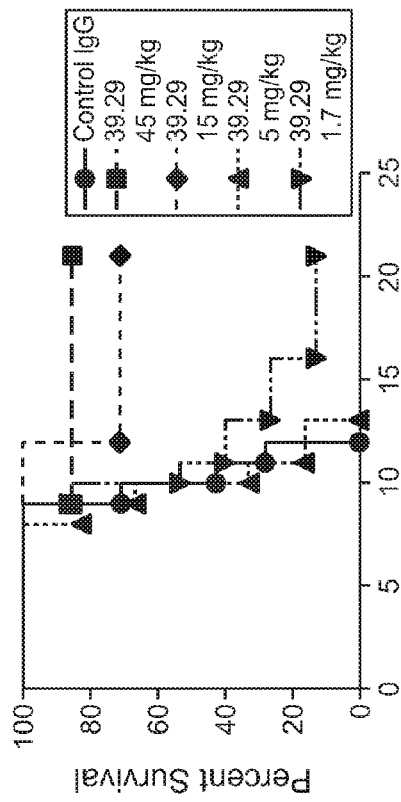
FIG. 13 sets forth data showing percent survival of mice infected with A/PR/8/1934 influenza A virus and administered various amounts of monoclonal antibody 39.29 NCv1.

For the H1N1 A/PR/8/1934 infected mice, a single i.v. dose of mAb 39.29 NCv1 at 15 mg/kg per mouse was efficacious compared to that observed with control IgG antibody. (See FIG. 13.) Specifically, 100% mortality was observed in the control treatment group by day 12, while a single dose of 15 mg/kg of mAb 39.29 NCv1 saved 87.5% of the infected mice. A threefold lower dose of 100 µg per mouse (approximately 5 mg/kg) of mAb 39.29 NCv1 exhibited some efficacy, being able to protect 25% of animals from the lethal challenge, while doses of approximately 1.7 mg/kg or approximately 0.56 mg/kg showed minimal efficacy beyond that observed in the control treatment group. (See FIG. 13.)

Figure 14:
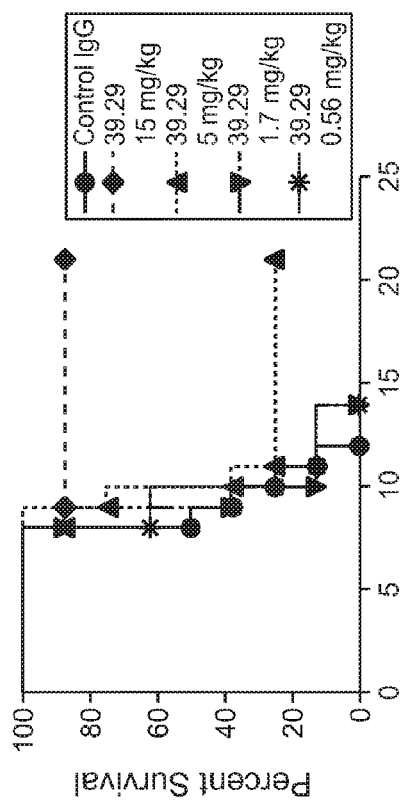
FIG. 14 sets forth data showing percent survival of mice infected with A/Hong Kong/1/1968 influenza A virus (an influenza A virus having a high IC50) and administered various amounts of monoclonal antibody 39.29 NCv1.

In another set of experiments, in vivo efficacy of mAb 39.29 NCv1 was further examined against mouse-adapted H3N2 Hong Kong influenza A virus strain (H3N2 A/Hong Kong/1/1968), which has a tenfold higher in vitro $IC_{50}$ than A/PR8/1934. As observed in previous experiments described above, mice treated with control antibody following influenza A virus infection showed 100% mortality by day 12. (See FIG. 14.) However, a single dose of mAb 39.29 NCv1 at approximately 45 mg/kg or approximately 15 mg/kg was able to protect 87.5% and 75% of the mice, respectively. The minimum efficacious dose of 15 mg/kg in vivo of mAb 39.29 NCv1 in both the A/PR8/1934 and the A/Hong Kong/1/1968 influenza A virus infection models is very similar despite the observed contrast in mAb 39.29 NCv1 in vitro $IC_{50}$ values between these two strains. (See FIGS. 3 and 14.)

Figure 15:
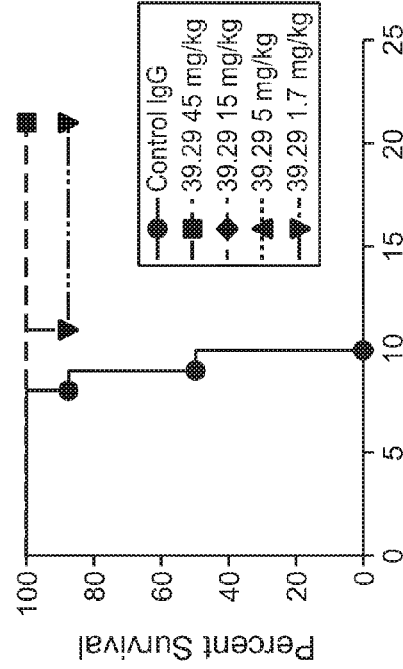
FIG. 15 sets forth data showing percent survival of mice infected with A/Port Chalmers/1/1973 influenza A virus and administered various amounts of monoclonal antibody 39.29 NCv1.
Figure 16:
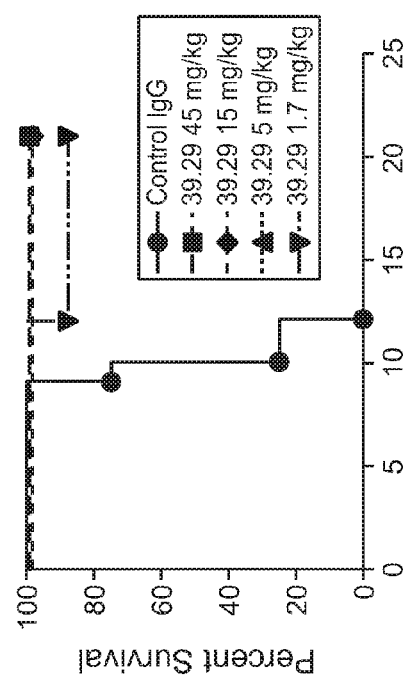
FIG. 16 sets forth data showing percent survival of mice infected with A/Aichi/2/1968 influenza A virus and administered various amounts of monoclonal antibody 39.29 NCv1.

To further explore the in vivo efficacy of mAb 39.29 NCv1, a dose titration of mAb 39.29 NCv1 was tested against two additional influenza A virus strains, Port Chalmers (H3N2 A/Port Chalmers/1/1973) and Aichi (H3N2 A/Aichi/2/1968). mAb 39.29 NCv1 has an in vitro $IC_{50}$ against Port Chalmers of 2.9 nM, which is very similar to that of A/PR8/1934, while Aichi has an in vitro $IC_{50}$ of 35.0 nM, a value closer to that of A/Hong Kong/1/1968. As shown in FIG. 15 and FIG. 16, 100% mortality was observed in the control treated animals by day 12 and day 10 for the Port Chalmers and Aichi models, respectively. Monoclonal antibody 39.29 NCv1 exhibited very efficacious against both influenza A virus strains at all tested doses (e.g., 45 mg/kg, 15 mg/kg, 5 mg/kg, and 1.7 mg/kg).

These data indicated, in part, that little correlation existed between the in vitro $IC_{50}$ of mAb 39.29 NCv1 and the in vivo minimum efficacious dose. None-the-less, a single dose of 15 mg/kg administered i.v. 72 hours post infection was efficacious in all four influenza A virus mouse models despite the range of in vitro $IC_{50}$ values for these influenza A virus strains.

Example 8. In Vivo Efficacy of mAb 39.29 and Oseltamivir in Severe Influenza a Virus Infection in Mice To compare the efficacy of anti-hemagglutinin antibodies of the present invention to that of oseltamivir phosphate (Tamiflu®) in mice, the following studies were performed. Balb/c mice (Charles River Laboratories, Hollister, Calif.) at 6-weeks old were infected intranasally with 50 µl H1N1 A/PR/8/1934 at 100× the lethal dose ($5 \times 10^4$ PFU/mouse). At 48 hours post infection, anti-hemagglutinin antibody 39.29 (a 50:50 mixture of mAb 39.29 D8C2 and mAb 39.29 NWPP ("NWPP" disclosed as SEQ ID NO: 177)) was administered as a single dose of approximately 15 mg/kg or control IgG in 200 µl PBS intravenously. In these experiments, an oseltamivir dosing regimen consisting of 2 mg dosed twice daily (BID) for five days was compared with a single 300 µg i.v. dose (~15 mg/kg) of mAb 39.29 NWPP ("NWPP" disclosed as SEQ ID NO: 177). A Log-rank test of mAb 39.29 NWPP ("NWPP" disclosed as SEQ ID NO: 177) or oseltamivir vs. control gave p<0.01 and a maximum likelihood test of mAb 39.29 NWPP ("NWPP" disclosed as SEQ ID NO: 177) vs. oseltamivir gave p<0.05. (Oseltamivir (i.e., Tamiflu®) was obtained from Toronto Research Chemicals, Cat. No. 0701000.)

Figure 17:
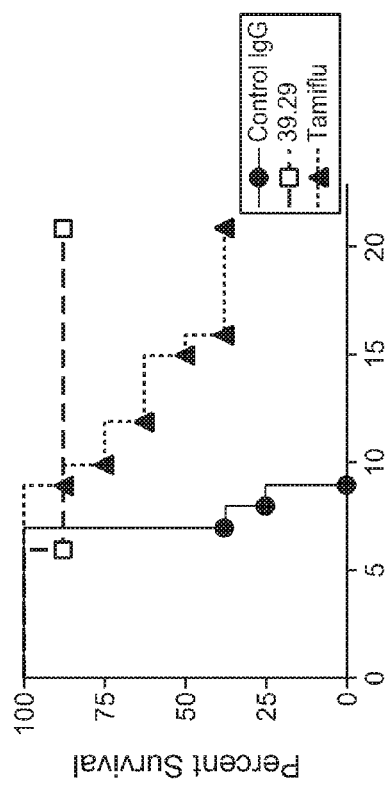
FIG. 17 sets forth data comparing percent survival of mice infected with influenza A virus strain A/PR/8/1934 and administered a 50:50 mixture of monoclonal antibody 39.29 D8C2 and monoclonal antibody 39.29 NWPP ("NWPP" disclosed as SEQ ID NO: 177) or oseltamivir (Tamiflu®).

As shown in FIG. 17, 100% mortality was observed by day 9 in control-IgG (mAb gD5237) treated animals. BID treatment of oseltamivir for 5 days only protected 37.5% of mice from lethality. However, a single 15 mg/kg dose of mAb 39.29 NWPP ("NWPP" disclosed as SEQ ID NO: 177) mixture protected 87.5% of the infected animals from the lethal influenza A virus challenge. (See FIG. 17.) The fully efficacious 15 mg/kg dose of mAb 39.29 NWPP ("NWPP" disclosed as SEQ ID NO: 177) mixture performed better than oseltamivir in mice severely infected with influenza A virus.

These results showed that a single dose of a monoclonal antibody of the present invention was more effective at treating influenza A virus infection than a 5-day treatment with oseltamivir.

Example 9. In Vivo Efficacy of mAb 39.29 NWPP ("NWPP" Disclosed as SEQ ID NO: 177) in Mice with and without Co-Administration of Oseltamivir Administration of oseltamivir is effective at reducing human influenza A virus infection if given within 48 hours after symptom onset. Unfortunately, oseltamivir shows minimal efficacy in patients who have been symptomatic for more than 48 hours. Therefore, the following experiments were performed to test if co-administration of a monoclonal antibody of the present invention and oseltamivir showed improved efficacy over either treatment alone. These experiments were performed using the severe mouse influenza infection model described above in Example 8. Briefly, female Balb/C mice (Charles River Laboratories) were infected with 100× the lethal dose ($5 \times 10^4$ pfu) of A/PR/8/1934 72-hours prior to i.v. administration of a single dose of 100 μg mAb 39.29 NWPP ("NWPP" disclosed as SEQ ID NO: 177) (approximately 6 mg/kg, a previously-determined sub-efficacious dose), control IgG, 2 mg BID oseltamivir, or a combination of a single dose of mAb 39.29 NWPP ("NWPP" disclosed as SEQ ID NO: 177) and oseltamivir treatment for 5 days. A Log-rank test of the combination treatment vs. mAb 39.29 NWPP ("NWPP" disclosed as SEQ ID NO: 177) or oseltamivir gives p<0.01.

Figure 18:
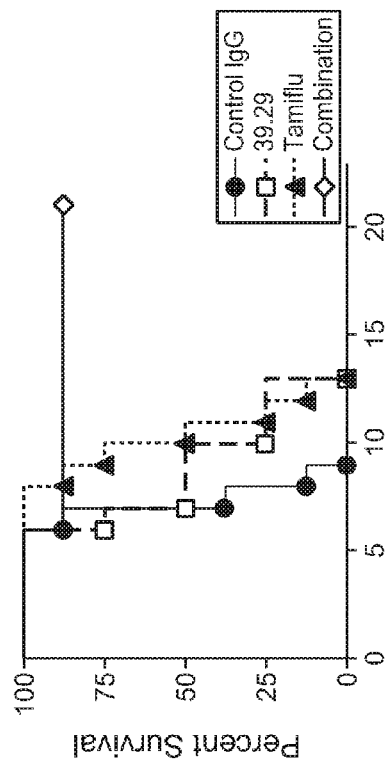
FIG. 18 sets forth data showing comparing percent survival of mice infected with influenza A virus strain A/PR/8/1934 and administered monoclonal antibody 39.29 NWPP ("NWPP" disclosed as SEQ ID NO: 177), oseltamivir (Tamiflu®), or a combination of monoclonal antibody 39.29 NWPP ("NWPP" disclosed as SEQ ID NO: 177) and oseltamivir.

As expected, control IgG treated animals exhibited 100% mortality 9 days post infection. (See FIG. 18.) The mortality observed for control-treated animals was very similar to the groups receiving only oseltamivir or a sub-efficacious dose of mAb 39.29 NWPP ("NWPP" disclosed as SEQ ID NO: 177). However, co-administration of a sub-efficacious dose of mAb 39.29 NWPP ("NWPP" disclosed as SEQ ID NO: 177) plus oseltamivir significantly improved survival compared to that observed in either treatment alone, resulting in 87.5% survival. (See FIG. 18.)

These results showed that a synergistic effect on the treatment of influenza A virus infection occurred during combination therapy using a monoclonal antibody of the present invention used in combination with oseltamivir, a neuraminidase inhibitor.

Example 10. Anti-Hemagglutinin Antibodies of the Present Invention Perform Better than Oseltamivir in a Ferret H5N1 Influenza A Virus Infection Model Ferret influenza A virus infection models are often used to examine prophylactic and therapeutic efficacy of anti-influenza therapeutics. Ferrets are considered a clinically relevant animal model for human influenza A virus infection. (See Matsuoka et al., (2009) *Current Protocols in Microbiology*, Chapter 15, Unit 15G 12.)

To examine the in vivo efficacy of mAb 39.29 D8C2 and mAb 81.39 B1C1 against a human isolate of H5N1 influenza A virus in ferrets, the following studies were performed. The ferret H5N1 study was completed under contract at the Lovelace Respiratory Research Institute (Albuquerque, N. Mex.). Male ferrets (*Mustela putorius furo*) were challenged with an intranasal dose of $1 \times 10^3$ pfu of the highly virulent H5N1 A/Vietnam/1203/04 influenza A virus strain (LD90 dose). Animals were infected 48 or 72 hours prior to receiving antibody by i.v. or oseltamivir (Tamiflu®) by oral gavage. The control treated animals received a 25 mg/kg i.v. dose of mAB gD5237, a monoclonal antibody specific for glycoprotein D of HSV. The anti-influenza treated animals received a single 25 mg/kg i.v. dose of either mAb 39.29 D8C2 or mAb 81.39 B1C1 at 48 or 72 hours post influenza virus infection. Each antibody treatment group included 10 ferrets. The oseltamivir treated animals received a twice-daily oral dose of 25 mg/kg for 5 days. Animals were monitored daily for weight loss, fever, and, body conditioning.

Figure 19B:
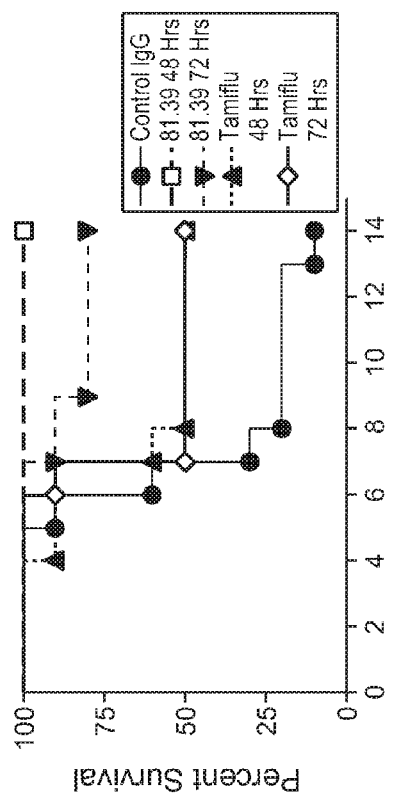
FIGS. 19A and 19B set for data comparing percent survival of ferrets infected with influenza A virus strain A/Vietnam/1203/04 (H5N1) and administered monoclonal antibody 39.29 D8C2 (FIG. 19A), monoclonal antibody 81.39 B1C1 (FIG. 19B), or oseltamivir (Tamiflu®) at 48 hours or 72 hours post-infection.
Figure 19A:
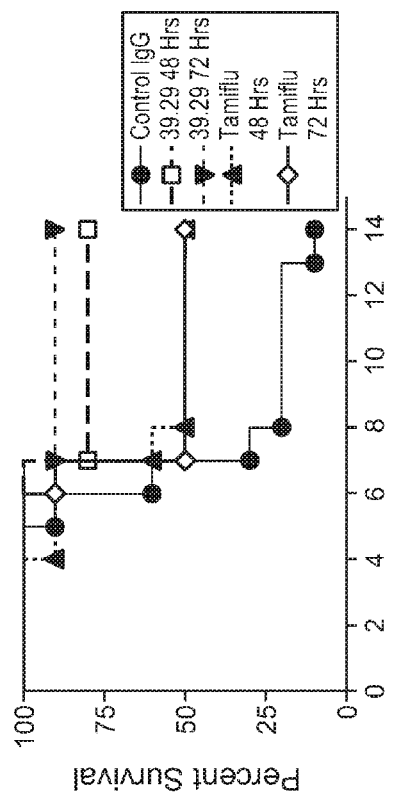

Consistent with an H5N1 infection, the majority of infected ferrets showed early signs of upper respiratory disease by 48 hours post infection. As expected with a lethal dose of H5N1, the negative control antibody treatment group exhibited 90% mortality by 14 days post inoculation. (See FIGS. 19A and 19B.)

In contrast, ferrets that received a single dose of mAb 39.29 D8C2 at either 48 or 72 hours post influenza virus infection showed 80% and 90% survival (20% and 10% mortality), respectively. (See FIG. 19A.) Likewise, ferrets that received a single dose of mAb 81.39 B1C1 at either 48 or 72 hours post infection showed 100% and 80% survival (0% and 20% mortality), respectively. (See FIG. 19B.) Irrespective of treatment initiation time, the oseltamivir treated groups showed 50% mortality.

These results showed that broadly neutralizing anti-hemagglutinin antibodies of the present invention were highly protective in the treatment of severe influenza A virus H5N1 infection in ferrets and performed better than oseltamivir when administered at either 48 and 72 hours post influenza A virus infection.

Example 11. Crystallization and Data Collection

In order to examine the structural basis for hemagglutinin cross-reactivity of the antibodies of the present invention, mAb 39.29 NCv1 Fab fragment was co-cystallized with recombinant hemagglutinin H3 from the human influenza A virus strain A/Perth/16/2009 as follows.

Protein Expression and Purification

To better understand the structural basis for hemagglutinin neutralization, the crystal structure of mAb 39.29 NCv1 Fab fragment in complex with hemagglutinin was determined as follows. Nucleic acid encoding the extracellular domain of Perth H3 hemagglutinin (H3HA, A/Perth/16/2009, amino acid residues 25-520 (SEQ ID NO: 226 for full-length hemagglutinin H3 (H3HA) amino acid sequence) was cloned into pACGP67 vector (BD Biosciences) in-frame with a thrombin cleavage site (LVPRGS, SEQ ID NO: 106), trimerization "foldon" sequence (PGSGYIPEAPRDGQAYVRKDGEWVLLSTFLG, SEQ ID NO:107), and a C-terminal 6×His tag (SEQ ID NO: 108). Recombinant baculovirus was generated by co-transfection of Sf9 cells with the H3HA-pACGP67 vector and linearized baculovirus DNA (Pharmingen).

To generate recombinant H3HA protein, *Trichoplusia ni* PRO cells were infected with the recombinant baculovirus using an MOI of 1 and grown for 72 hours at 27° C. Cell supernatants were treated with 50 mM Tris-HCl, pH 7.5, 5 mM $CaCl_2$, and 1 mM $NiCl_2$ followed by centrifugation and filtering. Media was then concentrated and buffer exchanged into 10 mM Tris, pH 8.0, and 150 mM NaCl (TBS) containing 20 mM imidazole by tangential flow filtration, and protein captured with Ni-agarose and eluted into TBS containing 200 mM imidazole. The foldon tag was cleaved overnight with thrombin, and H3HA was concentrated and further purified on a Superdex 200 16/60 size exclusion column equilibrated in TBS.

To generate the hemagglutinin-Fab complex, the mAb 39.29 NCv1 Fab (under control of the PhoA promoter) was expressed in *E. coli* overnight at 30° C. The cells were pelleted by centrifugation at 6,000 rpm for 15 minutes and lysed by micro-fluidization in PBS supplemented with 25 mM EDTA and 1 mM PMSF. Cell debris was removed by centrifugation at 10,000 rpm for 1 hour at 4° C. The resulting supernatant was passed through a Protein G column and Fab eluted with 0.58% acetic acid. Further purification of mAb 39.29 NCv1 Fab was achieved by SP sepharose chromatography using a gradient from 0 to 1 M NaCl in 20 mM IVIES, pH 5.5. To generate the HA/39.29 complex, H3HA was incubated overnight with excess mAb 39.29 NCv1 Fab, followed by concentration and 5200 size exclusion chromatography in TBS to isolate the complex. The complex was concentrated to 10 mg/ml for crystallization trials.

Crystallization

Crystal generation for the H3HA/39.29 NCv1 Fab complex were found in 0.1M Phosphate/Citrate buffer, pH 4.2, using 40% PEG 300 as precipitant (condition C6, the JCSG+ sparse matrix screen, Qiagen). Diffraction quality crystals were ultimately grown at 19° C. in sitting drops containing 0.1 μl protein and 0.1 μl 0.1M Phosphate/Citrate, pH 4.2, 40% PEG 300, and 0.7% 1-butanol. Crystals were cryoprotected in mother liquor followed by flash freezing and storage in liquid nitrogen. Data was collected under cryo-cooled conditions at the Canadian Light Source beamline CMCR-08ID and processed using MOSFLM and SCALA. The crystal belonged to the I213 space group, with unit cell dimensions of $a=b=c=204.4$ and $\alpha=\beta=\gamma=90°$.

Structure Determination

Initial phases were obtained by molecular replacement with PHASER using the structure of a H3HA (PDB 3SDY) as a search model. Subsequently the Fc and Fv portions of the Fab were placed separately using PHASER, and underwent initial rounds of rigid body refinement with Phenix. The model went through several iterative rounds of adjustment with COOT and simulated annealing, coordinate, and b-factor refinement with Phenix. Sugar molecules found at Asn-linked glycosylation sites were added using the Carboload package from Phenix, and final rounds of refinement were carried out using REFMAC5. The final model was refined at 3.1 Å with R/Rfree values of 19.9 and 25.9%, respectively. Ramachandran statistics calculated by Molprobity indicate 89.7% of the residues lie in favored regions with 1.1% outliers. Contacts were analyzed using the Protein Interfaces, Surfaces, and Assemblies (PISA) software and structural figures were prepared with PYMOL.

Example 12. Structural Characterization of the 39.29 Epitope on H3 Hemagglutinin As described above in Example 11, mAb 39.29 NCv1 Fab fragment was co-cystallized with recombinant H3 hemagglutinin from the human influenza A virus strain A/Perth/16/2009. The crystal structure of the antibody/hemagglutinin complex was determined at a resolution of 3.1 Å. The overall structure of A/Perth/16/2009 H3 hemagglutinin was similar to previously determined hemagglutinin structures with the exception of slight rearrangements and disorder in the HA2 helix 1/helix 2 linker. Disorder at these locations has been seen previously under low pH crystallization conditions, which is consistent with this complex being crystallized at pH 4.2 (Ekiert et al., (2011) Science 333:843-850). The crystal structure of the antibody/HA complex showed a single mAb 39.29 Fab molecule bound to each monomer of the uncleaved H3 HA trimer. Both the light chain and heavy chain fragments of mAb 39.29 NCv1 Fab fragments were well resolved throughout, allowing close examination of the Fv interaction with HA.

The epitope for mAb 39.29 NCv1 was determined to be on the stalk region of H3 hemagglutinin, roughly on top of the HA2 helix A. This region of the hemagglutinin stalk was first identified as a broadly neutralizing epitope for influenza A viruses expressing Group1 hemagglutinin subtypes (Ekiert et al., (2009) Science 324:246-251; Sui et al., (2009) Nature Structural & Molecular Biology 16:265-273)), and more recently as a neutralizing epitope for influenza A virus strains carrying Group1 and Group2 hemagglutinin subtypes (Corti et al., (2011) Science 333:850-856). mAb 39.29 NCv1 antibody uses extensive heavy and light chain contacts to bury approximately 1175 $Å^2$ of the hemagglutinin stalk surface area. The heavy chain of mAb 39.29 NCv1 contributes to binding largely through an extended hydrophobic CDRH3 loop that inserts into a shallow nonpolar groove adjacent to HA2 helix A and underneath a conserved Group2 hemagglutinin glycosylation site at Asn54. This CDRH3 loop extends Phe99 side-chain out to interact with H3 hemagglutinin Thr334, Ile390, and Ile393, while making main chain polar contacts with the GlcNAc attached to H3 hemagglutinin Asn54. The CDRH3 loop of mAb 39.29 NCv1 also makes a β-turn at Gly100, which is likely stabilized by inter-loop main chain contacts between Val98 and Ile100A. Ile100A faces downward to interact with a conserved H3 hemagglutinin Trp366, while Val98 and Pro100C also make van der Waals contacts with the H3 hemagglutinin stalk. Residing at the heavy/light chain interface, Pro100D and Trp100E terminate the long CDRH3 loop and act to anchor the loop in place.

The light chain of mAb 39.29 NCv1 also contributes significantly to the interaction with the H3 hemagglutinin stalk, making contacts with the H3 hemagglutinin stalk with all three light chain CDR loops as well as framework residues. Of the approximately 1100 $Å^2$ hemagglutinin buried surface area, ~60% is contributed by the light chain (640 $Å^2$ vs 480 $Å^2$ for light chain and heavy chain, respectively). The CDRL1 Asn32 makes hydrogen bond with H3 HA2 helix A residues Asp391 and Asn394, while CDRL1 His31 stacks against the H3 hemagglutinin Asn376 sidechain. Ser52 in the CDRL2 loop also makes a polar contact with Asn398. Within the CDRL3 loop, the backbone of Asn93 contacts Asp391 while Trp94 makes a cation-π interaction with Lys384 in the HA2 helix A. Interestingly, mAb 39.29 also makes a number of framework contacts with hemagglutinin, primarily through backbone interactions of the SGSGSG repeat (SEQ ID NO: 109) in beta-strand 6 of the IgKV3 with amino acid residues 403 to 405 in the H3 hemagglutinin polypeptide. Ser67 of mAb 39.29 NCv1 also makes polar interactions with Asp48 and Thr404 of H3 hemagglutinin.

All three mAb 39.89 NCv1 light chain CDR loops contribute to binding of the H3 HA stalk epitope, accounting for approximately 60% of the total buried surface area. This large dependence of light chain contacts is unique among known hemagglutinin Group1 and Group2 binding and neutralizing antibodies, with antibody F16v3 light chain contributing to only 20% to the buried surface area and antibody CR9114 light chain not making contact with the epitope.

Although structurally conserved, Group1 and Group2 hemagglutinin subtypes diverge significantly at the primary amino acid sequence level. To compare mAb 39.29 NCv1 H3HA contact residues with other hemagglutinin subtypes, we aligned the amino acid sequence of H3 hemagglutinin from influenza virus A/Perth/16/2009 with representative hemagglutinin amino acid sequences from other influenza virus strains: H1HA from A/California/07/2009; H2HA from A/Japan/305/1957; H5HA from A/Vietnam/1203/2004; and H7HA from A/chicken/NSW/1/1997. The amino acid numbering of H3 hemagglutinin from A/Perth/16/2009 in the crystal structure matches the hemagglutinin H3 sequence used in the alignment. The hemagglutinin sequence alignment was generated using clustalW and the amino acid sequences corresponding to hemagglutinin H1 from A/California/07/2009, hemagglutinin H2 from A/Japan/305/1957, hemagglutinin H3 from A/Perth/19/2009, hemagglutinin H5 from A/Vietnam/1203/2004, and hemagglutinin H7 from A/chicken/NSW/1/1997. The crystal structure was used to determine the contact residues between the 39.29 NCv1 Fab fragment and the stalk of hemagglutinin H3.

The alignment is presented in FIG. 20. Hemagglutinin contact residues (shaded in grey) are defined as residues within 4.5 Å of mAb 39.29 NCv1. Each amino acid residue that had greater than 50% of its available surface area buried by mAb 39.29 NCv1 Fab is marked with an asterisk.

A high degree of sequence conservation is observed among the contact residues that contribute significantly to the binding of mAb 39.29 NCv1 to this epitope. (See FIG. 20.) This observation suggests that mAb 39.29 NCv1 binds Group1 and Group2 hemagglutinin molecules via the same stalk epitope seen in the crystal structure described above. This epitope is similar to a hemagglutinin epitope identified for FI6v3 anti-hemagglutinin antibody (Corti et al., (2011), supra). However, mAb 39.29 NCv1 binds in a different orientation with respect to the hemagglutinin stalk than does FI6v3. Comparison of the 39.29 NCv1, FI6v3, and CR9114 structures in complex with HA revealed that all three antibodies bind an epitope that includes the HA2 helix A and adjacent non-polar groups. However, each of the three antibodies has a unique binding orientation, with each heavy chain bound to a similar topographical position on HA but with light chain positioning rotated by ~60° (FI6v3) or ~120° (CR9114) when compared to 39.29 NCv1. Also unique to mAb 39.29 NCv1, the IgKV3 light chain SGSGSG repeat (SEQ ID NO: 109) in beta-strand 6 framework makes contact with H3 HA. Therefore, the 39.29 structure represents a third solution to the binding of this highly conserved epitope and solidifies the importance of engaging the HA2 helix A for broad neutralization of influenza A virus.

The crystallography data of mAb 39.29 in complex with H3 hemagglutinin from the human influenza A virus strain A/Perth/16/2009 revealed the following contact positions: 34, 36, 54, 70, 292, 294, 305, 307, 334, 363, 364, 365, 366, 379, 380, 382, 383, 384, 386, 387, 390, 391, 393, 394, 395, 397, 398, 401, 403, 404, and 405. Antibody FI6v3 showed the following contact positions: 334, 352, 356, 363, 364, 365, 366, 381, 383, 384, 386, 387, 388, 390, 391, 393, 394, 397, 398, 401, and 402. Amino acid residue positions correspond to H3 hemagglutinin from influenza A virus strain A/Perth/16/2009 (SEQ ID NO:226). (See International Application Publication Nos: WO 2010/010466 and WO 2013/011347; Corti et al. (2011) *Science* 333:850-856.) While some overlap is observed, mAb 39.29 showed a greater number of contact positions within hemagglutinin than FI6v3.

The fact that mAb 39.29 NCv1 and FI6v3 antibody CDRs have no sequence homology and that both antibodies engage a similar but not identical stalk epitope in different ways suggests that there are various ways for antibodies to bind the conserved stalk epitope and broadly neutralize influenza A viruses.

Example 13. Competition ELISA

Competition ELISA assays were developed using hemagglutinin H1 from influenza virus A/WSN/1933 and hemagglutinin H3 from influenza virus A/Hong Kong/8/1968. Hemagglutinin-coated ELISA plates were allowed to bind test antibody at various concentrations (X-axis) prior to the addition of saturating concentrations of biotin labeled mAb 39.29. If the test antibody competed for the hemagglutinin epitope of mAb 39.29, the biotin ELISA signal (Y-axis) was decreased as a function of increasing test antibody concentration. The binding data were fit with a non-linear dose response curve to determine the $EC_{50}$ value given in nM.

mAb 39.29 IgG was biotinylated through amine coupling according to the manufacturer's recommended protocol (Sulfo-NHS-LC-LC, Pierce, Rockford, Ill.). Final stock concentration of the biotinylated mAb was 13.2 mM. To determine the optimal concentration for usage, the biotinylated 39.29 was serially titrated against immobilized H1 hemagglutinin from influenza A virus A/WSN/1933 and H3 hemagglutinin from influenza A virus A/Hong Kong/8/1968. Recombinant hemagglutinin H1 and H3 proteins were diluted to 2 µg/ml in phosphate buffered saline (PBS) and dispensed (100 µl) onto 96-well Nunc Maxisorp plates (Nunc, Rochester, N.Y.). The plates were coated overnight at 4° C., rinsed in PBS, and then blocked for 1-hour at room temperature with PBS containing 1% bovine serum albumin (BSA, Sigma-Aldrich, St. Louis, Mo.).

Each plate then received 100 µl of serially diluted biotinylated mAb 39.29 starting at an initial concentration of 88 nM with 1/3 dilutions in PBS containing 1.0% BSA and 0.05% Polysorbate 20 (Sigma-Aldrich). After one hour incubation, the plates were washed and then incubated with 100 µl of a 1:5000 dilution of streptavidin-conjugated horseradish peroxidase (Caltag Laboratories, Carlsbad, Calif.) for 30 minutes at room temperature. Following the incubation, the plates were washed and developed with 100 µl of TMB substrate (Kirkegaard and Perry Laboratories, Inc. Gaithersburg, Md.). Plates were read on a SpectraMax plate reader (Molecular Devices, Sunnyvale, Calif.) at O.D. 450 nM. The optimal concentration of biotinylated mAb was determined to be 1 nM.

Various concentration (x-axis) of monoclonal antibodies 39.18, 36.89, 81.39 39.29, mAb 9, mAb 23 of the present invention and control IgG were incubated with the hemagglutinin-coated plates for 30 minutes at room temperature. Initial concentration was 200 nM followed by 3 fold serial dilutions. Biotinylated mAb 39.29 was added to a final sub-saturating concentration of 1 nM. Following one hour incubation, the plates were washed and incubated with 100

µl of a 1:5000 dilution of Streptavidin-conjugated horseradish peroxidase for 45-minutes. Plates were washed and then develop with TMB solution. If the test antibody competed for the HA epitope of mAb 39.29, the biotin ELISA signal (Y-axis) was decreased as a function of increasing test antibody concentration. The binding data were fit with a non-linear dose response curve to determine the $EC_{50}$ value given in nM.

Figure 21A:
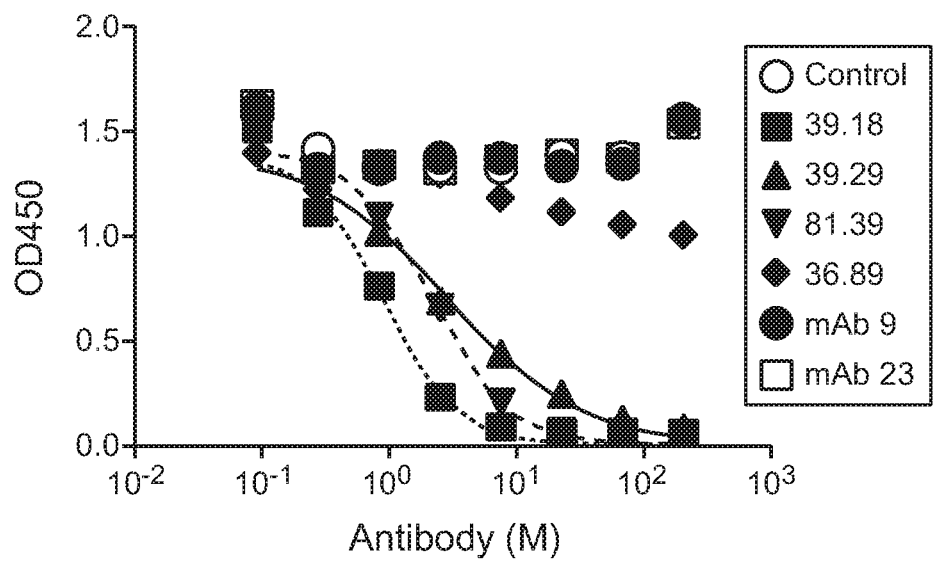
FIGS. 21A and 21B set forth data from competition ELISA experiments of various monoclonal antibodies of the present invention competing with binding of biotin-labeled monoclonal antibody 39.29 to hemagglutinin H1 from A/NWS/1933 (FIG. 21A) and hemagglutinin H3 from A/HK/8/1968 (FIG. 21B).
Figure 21B:
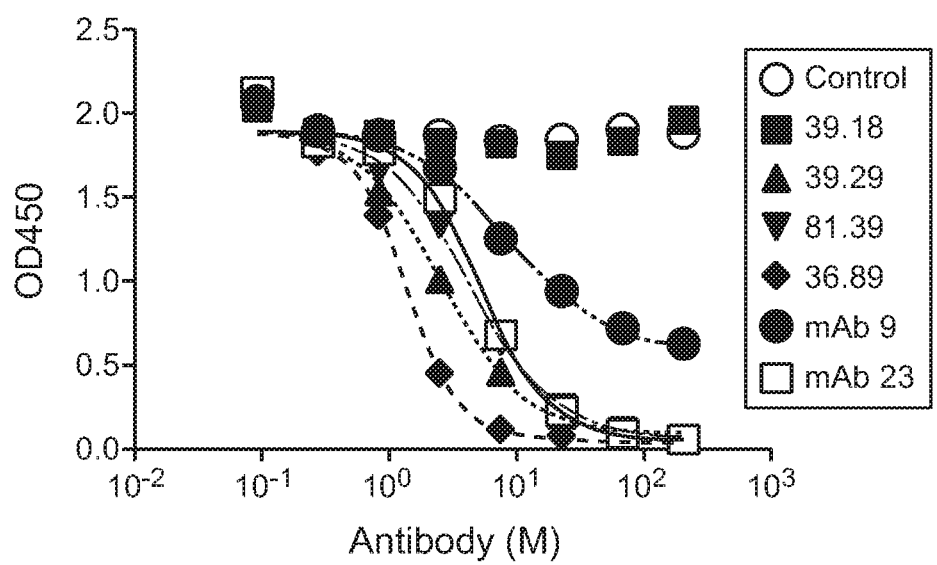

FIGS. 21A and 21B show results of competition ELISA analysis of the mAbs for binding to H1HA from A/NWS/1933 (FIG. 21A) or H3HA from A/HK/8/1968 (FIG. 21B). The results showed that mAb 39.29, mAb 81.39, mAb 39.18, and mAb 36.89 all bind to an overlapping hemagglutinin stalk epitope (FIGS. 21A and 21B). Specifically, mAb 81.39 and mAb 39.18 compete for binding of mAb 39.29 on the stalk of hemagglutinin H1 (FIG. 21A), while mAb 81.39 and mAb 36.89 compete for binding with mAb 39.29 for the identified stalk epitope on hemagglutinin H3 (FIG. 21B).

By using competition ELISA assays it was established that monoclonal antibodies 81.39, 39.18, 36.89, mAb 9, and mAb 23 bind to the highly conserved stalk epitope of hemagglutinin identified by the structural analysis. Specifically, the mAb 81.39 and mAb 39.18 compete for binding of mAb 39.29 on the stalk of the Group1 H1 hemagglutinin. Additionally, mAb 81.39, mAb 36.89, mAb 9, and mAb 23 compete for binding with mAb 39.29 for the identified stalk epitope on the Group2 H3 hemagglutinin. As predicted, since mAb 39.18 neutralizes only Group1 Influenza A isolates, it does not compete for binding of the mAb 39.29 epitope on Group2 hemagglutinin. Likewise, mAb 36.89, mAb 9, and mAb 23 only neutralize Group2 Influenza A isolates and therefore do not compete for binding of mAb 39.29 on Group1 H1 hemagglutinin. The data from these experiments is further summarized in Table 3 below.

TABLE 3

| Influenza Isolate | HA Subtype | mAb 39.18 | mAb 39.29 | mAb 81.39 | mAb 36.89 | mAb 9 | mAb 23 |
|---|---|---|---|---|---|---|---|
| A/NWS/1933 | Grp1/H1 | 0.88 | 2.8 | 2.15 | — | — | — |
| A/HK/8/1968 | Grp2/H3 | — | 2.54 | 4.21 | 1.32 | 8.42 | 1.84 |

$EC_{50}$ given in nM

— Indicates EC50 >200 nM

Example 14. Safety and Pharmacokinetics of Anti-Influenza a Virus Antibody in Healthy Volunteers A phase 1 single-ascending dose study of mAb 39.29-NWPP in healthy human male and female subjects 18 years of age or older was performed. Initial dosing to investigate the safety, tolerability, and pharmacokinetics in healthy adult subjects was performed by i.v. administration of a single dose (1.5 mg/kg, 5 mg/kg, 15 mg/kg, or 45 mg/kg) of mAb39.29. mAb39.29 was safe and well-tolerated at all dose levels after a follow-up period of at least 58 days for the 45 mg/kg dose level and 120 days for the 1.5 mg/kg dose level. No serious adverse events related to study drug were reported.

Serum concentrations of mAb 39.29 exhibited a biphasic disposition with an initial rapid distribution phase followed by a slow elimination phase. mAb39.29 demonstrated linear pharmacokinetics (PK). The mean $C_{max}$ increased in a dose-proportional manner of 33.5 μg/mL for the 1.5 mg/kg dose group and 1180 μg/mL for the 45 mg/kg dose group. Similarly, the group mean $AUC_{0\text{-}infinity}$ was 518 and 5530 μg/mL*day for the 1.5 mg/kg and 15 mg/kg dose groups, respectively, and is approximately dose proportional. On the basis of the available PK data in healthy male and female subjects, mAb 39.29 appeared to have a PK profile consistent with that of a typical IgG1 human antibody with a mean half-life of approximately 20 days (Mean Range 19.3-22.2).

Example 15. Phase 2 Study of Anti-Influenza A Virus Hemagglutinin Antibody

A phase 2 clinical study of an anti-influenza A virus hemagglutinin antibody of the present invention is performed as follows. Hospitalized individuals having influenza A virus infection are administered an anti-influenza A virus hemagglutinin antibody of the present invention by intravenous administration, at a dose of 1.5 mg/kg, 5 mg/kg, 15 mg/kg, or 45 mg/kg. Alternatively, individuals are administered antibody at a fixed dose of 120 mg, 400 mg, 1200 mg, or 3600 mg. Individuals may also be administered oseltamivir (Tamiflu®) (current standard of care) prior to, at the time of, or subsequent to administration of the anti-influenza A virus hemagglutinin antibody. Generally, a one-time dosing regimen of the antibody is used, although subsequent doses are contemplated.

Administration of an anti-influenza A virus hemagglutinin antibody of the present invention shows efficacy at treating influenza A virus infection, including reduction of influenza A virus infectivity, reduction in the length of hospital stay, reduction or prevention of the need for intensive care unit use, reduction or prevention of the need for assisted or mechanical ventilation, or reduction or prevention of the need for supplemental oxygen use.

Administration of an anti-influenza A virus hemagglutinin antibody of the present invention results shows efficacy at treating influenza A virus infection by reduction of time to normalization of respiratory function (such as a reduction of time to normalization of respiratory rate, or a reduction of time to normalization of oxygen saturation), reduction of time to return to normal oxygen saturation, e.g., to an oxygen saturation of about 92% or greater, as measured over a 24 hour period without supplemental oxygen administration, or reduction of time to normalization of vital signs, such as heart rate, blood pressure, respiratory rate, and temperature.

Statistical Analyses

Statistics were calculated using JMP version 9.0.2 software (SAS Institute). Survival experiments were compared using log-rank test. P values<0.05 were considered significant. $IC_{50}$ curves and values were plotted and calculated using Graphpad Prism version 5.0 software.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method for treating, inhibiting, or preventing influenza A virus infection in an individual in need thereof, the method comprising administering to the individual an effective amount of a composition comprising an anti-hemagglutinin monoclonal antibody that specifically binds influenza A virus hemagglutinin, wherein the antibody comprises three heavy chain hypervariable regions (HVR-H1, HVR-H2, and HVR-H3) and three light chain hypervariable regions (HVR-L1, HVR-L2, and HVR-L3), wherein:
   (a) HVR-H1 comprises the amino acid sequence of SEQ ID NO:178;
   (b) HVR-H2 comprises the amino acid sequence of SEQ ID NO:179;
   (c) HVR-H3 comprises the amino acid sequence of SEQ ID NO:181;
   (d) HVR-L1 comprises the amino acid sequence of SEQ ID NO:183;
   (e) HVR-L2 comprises the amino acid sequence of SEQ ID NO:187; and
   (f) HVR-L3 comprises the amino acid sequence of SEQ ID NO:189,
   thereby treating, inhibiting, or preventing influenza A virus infection.

2. A method for treating, inhibiting, or preventing influenza A virus infection in an individual in need thereof, the method comprising administering to the individual an effective amount of a composition comprising an anti-hemagglutinin monoclonal antibody that specifically binds influenza A virus hemagglutinin, wherein the antibody comprises a heavy chain variable region and a light chain variable region, wherein the heavy chain variable region comprises the amino acid sequence of SEQ ID NO:115, and the light chain variable region comprises the amino acid sequence of SEQ ID NO:117, thereby treating, inhibiting, or preventing influenza A virus infection.

3. A method for treating, inhibiting, or preventing influenza A virus infection in an individual in need thereof, the method comprising administering to the individual an effective amount of a composition comprising an anti-hemagglutinin monoclonal antibody that specifically binds influenza A virus hemagglutinin, wherein the antibody comprises a heavy chain and a light chain, wherein the heavy chain comprises the amino acid sequence of SEQ ID NO:114, and the light chain comprises the amino acid sequence of SEQ ID NO:116, thereby treating, inhibiting, or preventing influenza A virus infection.

4. The method of claim 1, wherein the method further comprises administering to the individual an additional therapeutic agent, wherein the additional therapeutic agent is a neuraminidase inhibitor, an anti-hemagglutinin antibody that binds influenza A virus hemagglutinin, or an anti-M2 antibody that binds influenza A virus M2 protein.

5. The method of claim 2, wherein the method further comprises administering to the individual an additional therapeutic agent, wherein the additional therapeutic agent is a neuraminidase inhibitor, an anti-hemagglutinin antibody that binds influenza A virus hemagglutinin, or an anti-M2 antibody that binds influenza A virus M2 protein.

6. The method of claim 3, wherein the method further comprises administering to the individual an additional therapeutic agent, wherein the additional therapeutic agent is a neuraminidase inhibitor, an anti-hemagglutinin antibody that binds influenza A virus hemagglutinin, or an anti-M2 antibody that binds influenza A virus M2 protein.

7. The method of claim 4, claim 5, or claim 6, wherein the additional therapeutic agent is a neuraminidase inhibitor selected from the group consisting of oseltamivir, zanamivir, amantadine, and rimatadine.

8. The method of claim 1, claim 2, or claim 3, wherein the individual is a human.

9. The method of claim 4, claim 5, or claim 6, wherein the anti-hemagglutinin monoclonal antibody and the additional therapeutic agent are administered simultaneously or sequentially.

10. The method of claim 4, claim 5, or claim 6, wherein the additional therapeutic agent is administered to the individual prior to administration of the anti-hemagglutinin monoclonal antibody.

11. The method of claim 4, claim 5, or claim 6, wherein the additional therapeutic agent is administered to the individual at the same time as administration of the anti-hemagglutinin monoclonal antibody.

12. The method of claim 4, claim 5, or claim 6, wherein the anti-hemagglutinin monoclonal antibody is administered to the individual following administration of the additional therapeutic agent.

13. The method of claim 4, claim 5, or claim 6, wherein the anti-hemagglutinin monoclonal antibody is administered to the individual prior to administration of the additional therapeutic agent.

14. The method of claim 4, claim 5, or claim 6, wherein the anti-hemagglutinin monoclonal antibody and the additional therapeutic agent are administered to the individual simultaneously.

15. The method of claim 1, claim 2, or claim 3, wherein the anti-hemagglutinin monoclonal antibody is administered to the individual at about 12 hours after onset of symptoms, at about 24 hours after onset of symptoms/illness (symptoms of influenza A virus infection), at about 36 hours after onset of symptoms, at about 48 hours after onset of symptoms, at about 60 hours after onset of symptoms, at about 72 hours after onset of symptoms, at about 84 hours after onset of symptoms, or at about 96 hours after onset of symptoms.

16. The method of claim 1, claim 2, or claim 3, wherein the anti-hemagglutinin monoclonal antibody is administered to the individual between about 24 hours and 48 hours after onset of symptoms, between about 48 hours and 72 hours after onset of symptoms, or between about 72 hours and 96 hours after onset of symptoms.

17. The method of claim 1, claim 2, or claim 3, wherein the anti-hemagglutinin monoclonal antibody is administered by parenteral, intrapulmonary, or intranasal administration.

18. The method of claim 17, wherein the parenteral administration is selected from the group consisting of intramuscular administration, intravenous administration, intraarterial administration, intraperitoneal administration, and subcutaneous administration.

19. The method of claim 1, claim 2, or claim 3, wherein the antibody is effective at treating, inhibiting, or preventing infection by group 1 influenza A virus subtypes and by group 2 influenza A virus subtypes.

* * * * *

SEQUENCE LISTING

<160> NUMBER OF SEQ ID NOS: 245

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atcgtttcat aagcgcgcca ggtgcagctg gtgcagtc                              38

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atcgtttcat aagcgcgcca grtcaccttg aaggagtc                              38

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atcgtttcat aagcgcgcga ggtgcagctg gtggagtc                              38

<210> SEQ ID NO 4
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atcgtttcat aagcgcgcca ggtgcagctg gtggagtc                              38

<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atcgtttcat aagcgcgcga agtgcagctg gtggagtc                              38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
atcgtttcat aagcgcgcca ggtgcagctg caggagtc                              38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atcgtttcat aagcgcgcca gctgcagctg caggagtc                                38

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atcgtttcat aagcgcgcga rgtgcagctg gtgcagtc                                38

<210> SEQ ID NO 9
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atcgtttcat aagcgcgcca ggtacagctg cagcagtc                                38

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
atcgtttcat aagcgcgcca ggtgcagctg gtgcaatc                                38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atcgtttcat aagcgcgcca ggtccagctt gtgcagtc                                38

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atcgtttcat aagcgcgcca ggttcagctg gtgcagtc                                38

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atcgtttcat aagcgcgcca ggtccagctg gtacagtc                              38

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
atcgtttcat aagcgcgcca gatgcagctg gtgcagtc                              38

<210> SEQ ID NO 15
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atcgtttcat aagcgcgcca aatccagctg gtgcagtc                              38

<210> SEQ ID NO 16
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcgtttcat aagcgcgcga ggtccagctg gtgcagtc                              38

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atcgtttcat aagcgcgcga ggtgcagctg ttggagtc                              38

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
atcgtttcat aagcgcgcga ggtgcagctg gtggagac                              38

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
atcgtttcat aagcgcgcca ggtgcagcta cagcagtg            38

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gacattctac gagctagctg aggagacagt gaccagggt            39

<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gacattctac gagctagctg aggagacggt gaccagggt            39

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gacattctac gagctagctg aagagacggt gaccattgtc            40

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gacattctac gagctagctg aggagacggt gaccgtgg            38

<210> SEQ ID NO 24
<211> LENGTH: 79
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
tctcctcagc tagcggtggc ggcggttccg gaggtggtgg ttctggcggt ggtggcagcg            60
acatccagwt gacccagtc            79

-continued

```
<210> SEQ ID NO 25
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tctcctcagc tagcggtggc ggcggttccg gaggtggtgg ttctggcggt ggtggcagcg    60
atgttgtgat gactcagtc                                                 79

<210> SEQ ID NO 26
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tctcctcagc tagcggtggc ggcggttccg gaggtggtgg ttctggcggt ggtggcagcg    60
aaattgtgwt gacrcagtc                                                 79

<210> SEQ ID NO 27
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctcctcagc tagcggtggc ggcggttccg gaggtggtgg ttctggcggt ggtggcagcg    60
atattgtgat gacccacac                                                 79

<210> SEQ ID NO 28
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctcctcagc tagcggtggc ggcggttccg gaggtggtgg ttctggcggt ggtggcagcg    60
aaacgacact cacgcagtc                                                 79

<210> SEQ ID NO 29
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tctcctcagc tagcggtggc ggcggttccg gaggtggtgg ttctggcggt ggtggcagcg    60
aaattgtgct gactcagtc                                                 79

<210> SEQ ID NO 30
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 30
agttcatgcc atggttttga tttccacctt ggtccctt                            38

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agttcatgcc atggttttga tctccacctt ggtccc                              36

<210> SEQ ID NO 32
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
agttcatgcc atggttttga tatccacttt ggtcccag                            38

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
agttcatgcc atggttttga tctccagctt ggtccct                             37

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
agttcatgcc atggttttaa tctccagtcg tgtccctt                            38

<210> SEQ ID NO 35
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tctcctcagc tagcggtggc ggcggttccg gaggtggtgg ttctggcggt ggtggcagcc   60
agtctgtgct gactcagcc                                                79

<210> SEQ ID NO 36
<211> LENGTH: 79
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tctcctcagc tagcggtggc ggcggttccg gaggtggtgg ttctggcggt ggtggcagcc    60
agtctgtgyt gacgcagcc                                                 79

<210> SEQ ID NO 37
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tctcctcagc tagcggtggc ggcggttccg gaggtggtgg ttctggcggt ggtggcagcc    60
agtctgtcgt gacgcagcc                                                 79

<210> SEQ ID NO 38
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctcctcagc tagcggtggc ggcggttccg gaggtggtgg ttctggcggt ggtggcagcc    60
artctgccct gactcagcc                                                 79

<210> SEQ ID NO 39
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tctcctcagc tagcggtggc ggcggttccg gaggtggtgg ttctggcggt ggtggcagct    60
cctatgwgct gactcagcc                                                 79

<210> SEQ ID NO 40
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctcctcagc tagcggtggc ggcggttccg gaggtggtgg ttctggcggt ggtggcagct    60
cttctgagct gactcagga                                                 79

<210> SEQ ID NO 41
<211> LENGTH: 79
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
tctcctcagc tagcggtggc ggcggttccg gaggtggtgg ttctggcggt ggtggcagcc    60
acgttatact gactcaacc                                                 79

<210> SEQ ID NO 42
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tctcctcagc tagcggtggc ggcggttccg gaggtggtgg ttctggcggt ggtggcagcc    60
aggctgtgct gactcagcc                                                 79

<210> SEQ ID NO 43
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctcctcagc tagcggtggc ggcggttccg gaggtggtgg ttctggcggt ggtggcagca    60
attttatgct gactcagcc                                                 79

<210> SEQ ID NO 44
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctcctcagc tagcggtggc ggcggttccg gaggtggtgg ttctggcggt ggtggcagcc    60
agrctgtggt gacycagga                                                 79

<210> SEQ ID NO 45
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tctcctcagc tagcggtggc ggcggttccg gaggtggtgg ttctggcggt ggtggcagcc    60
wgcctgtgct gactcagcc                                                 79

<210> SEQ ID NO 46
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
agttcatgcc atggttagga cggtgacctt ggtcc                              35

<210> SEQ ID NO 47
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agttcatgcc atggttagga cggtcagctt ggtcc                              35

<210> SEQ ID NO 48
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agttcatgcc atggtgagga cggtcagctg ggtg                               34

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
atcgtttcat aagcgcgcsa                                               20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agttcatgcc atggttttga t                                             21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
agttcatgcc atggtkagga c                                             21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gaagtagtcc ttgaccaggc ag                                            22

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ctcagcgtca gggtgytgct gag                                             23

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gggtktggts gtctccac                                                   18

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
caggtgcagc tggtgcagtc tggggc                                          26

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
caggtccagc tggtgcagtc tggggc                                          26

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
caggtcacct tgaaggagtc tggtcc                                          26

<210> SEQ ID NO 58
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gaggtgcagc tggtggagtc tggggg                                          26

```
<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
caggtgcagc tgcaggagtc gggccc                                        26

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaggtgcagc tggtgcagtc tgg                                           23

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caggtacagc tgcagcagtc aggtcc                                        26

<210> SEQ ID NO 62
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
caggtgcagc tggtgcaatc tgg                                           23

<210> SEQ ID NO 63
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ghcatccrgw tgacccagtc tc                                            22

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gatrttgtga tgacycagwc tc                                            22
```

```
<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gaaatwgtrw tgacrcagtc tc                                              22

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gacatcgtga tgacccagtc tcc                                             23

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gaaacgacac tcacgcagtc tc                                              22

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gawrttgtgm tgacwcagtc tc                                              22

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagtctgtgy tgackcagcc rccctc                                          26

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cagtctgccc tgactcagcc t                                               21

<210> SEQ ID NO 71
```

-continued

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcctatgagc tgacwcagsh vccckc                                          26

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagcctgtgc tgactcartc vccctc                                          26

<210> SEQ ID NO 73
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cagcctgtgc tgactcagcc aacttc                                          26

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
aattttatgc tgactcagcc ccac                                            24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
caggctgtgg tgactcagga gccc                                            24

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cagactgtgg tgacccagga gcc                                             23

<210> SEQ ID NO 77
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cagcctgtgc tgactcagcc acc                                            23

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gcagcccagg gcsgctgtgc                                                20

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gcacacaaca gaggcagttc cag                                            23

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cttgragctc ctcagaggag                                                20

<210> SEQ ID NO 81
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ccaccatggg atggtcatgt atcatccttt ttctagtagc aactgcaact ggagtacatt    60
cacagg                                                               66

<210> SEQ ID NO 82
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ccaccatggg atggtcatgt atcatccttt ttctagtagc aactgcaact ggagtacatt    60
cacagatcac ct                                                        72
```

<210> SEQ ID NO 83
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccaccatggg atggtcatgt atcatccttt ttctagtagc aactgcaact ggagtacatt      60
cacag                                                                 65

<210> SEQ ID NO 84
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ccaccatggg atggtcatgt atcatccttt ttctagtagc aactgcaact ggagtacatt      60
cagagg                                                                66

<210> SEQ ID NO 85
<211> LENGTH: 78
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ccaccatggg atggtcatgt atcatccttt ttctagtagc aactgcaact ggagtacatt      60
cacaggtgca gctgcagg                                                   78

<210> SEQ ID NO 86
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccaccatggg atggtcatgt atcatccttt ttctagtagc aactgcaact ggagtacatt      60
cagaggtgca                                                            70

<210> SEQ ID NO 87
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccaccatggg atggtcatgt atcatccttt ttctagtagc aactgcaact ggagtacatt      60
cacaggtaca gc                                                         72

<210> SEQ ID NO 88
<211> LENGTH: 70
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 88
ccaccatggg atggtcatgt atcatccttt ttctagtagc aactgcaact ggagtacatt    60
cacaggtgca                                                           70

<210> SEQ ID NO 89
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
ccaccatggg atggtcatgt atcatccttt ttctagtagc aactgcaact ggagtacatt    60
cagacatcca gatgacccag tctccatcct ccctg                               95

<210> SEQ ID NO 90
<211> LENGTH: 95
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
ccaccatggg atggtcatgt atcatccttt ttctagtagc aactgcaact ggagtacatt    60
cagatattgt gatgactcag tctcactctc cctgc                               95

<210> SEQ ID NO 91
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
ccaccatggg atggtcatgt atcatccttt ttctagtagc aactgcaact ggagtacatt    60
cagaaattgt gttgacacag tctccagcca ccctgtcttt g                       101

<210> SEQ ID NO 92
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
ccaccatggg atggtcatgt atcatccttt ttctagtagc aactgcaact ggagtacatt    60
cagacatcgt gatgacccag tctccagact ccctggctgt g                       101

<210> SEQ ID NO 93
<211> LENGTH: 88
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 93
ccaccatggg atggtcatgt atcatccttt ttctagtagc aactgcaact ggagtacatt    60
cagaaacgac actcacgcag tctccagc    88

<210> SEQ ID NO 94
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ccaccatggg atggtcatgt atcatccttt ttctagtagc aactgcaact ggagtacatt    60
cagaaattgt gctgactcag tctccagact ttcg    94

<210> SEQ ID NO 95
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
ccaccatggg atggtcatgt atcatccttt ttctagtagc aactgcaact ggagtacatt    60
cacagtctgt gytgackcag ccrccctc    88

<210> SEQ ID NO 96
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccaccatggg atggtcatgt atcatccttt ttctagtagc aactgcaact ggagtacatt    60
cacagtctgc cctgactcag cct    83

<210> SEQ ID NO 97
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ccaccatggg atggtcatgt atcatccttt ttctagtagc aactgcaact ggagtacatt    60
catcctatga gctgacwcag shvccckc    88

<210> SEQ ID NO 98
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
ccaccatggg atggtcatgt atcatccttt ttctagtagc aactgcaact ggagtacatt    60

```
cacagcctgt gctgactcar tcvccctc                                              88

<210> SEQ ID NO 99
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
ccaccatggg atggtcatgt atcatccttt ttctagtagc aactgcaact ggagtacatt          60
cacagcctgt gctgactcag ccaacttc                                              88

<210> SEQ ID NO 100
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
ccaccatggg atggtcatgt atcatccttt ttctagtagc aactgcaact ggagtacatt          60
caaattttat gctgactcag ccccac                                                86

<210> SEQ ID NO 101
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
ccaccatggg atggtcatgt atcatccttt ttctagtagc aactgcaact ggagtacatt          60
cacaggctgt ggtgactcag gagccc                                                86

<210> SEQ ID NO 102
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
ccaccatggg atggtcatgt atcatccttt ttctagtagc aactgcaact ggagtacatt          60
cacagactgt ggtgacccag gagcc                                                 85

<210> SEQ ID NO 103
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
ccaccatggg atggtcatgt atcatccttt ttctagtagc aactgcaact ggagtacatt          60
cacagcctgt gctgactcag ccacc                                                 85
```

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gccaggggga agaccgatg                                               19

<210> SEQ ID NO 105
<211> LENGTH: 59
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctgggataga agttattcag caggcacaca acagaagcag ttccagattt caactgctc   59

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Leu Val Pro Arg Gly Ser
1               5

<210> SEQ ID NO 107
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Pro Gly Ser Gly Tyr Ile Pro Glu Ala Pro Arg Asp Gly Gln Ala Tyr
1               5                   10                  15

Val Arg Lys Asp Gly Glu Trp Val Leu Leu Ser Thr Phe Leu Gly
            20                  25                  30

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 108

His His His His His His
1               5

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ser Gly Ser Gly Ser Gly
1               5

<210> SEQ ID NO 110
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

```
Gln Val Gln Leu Val Glu Ser Gly Gly Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335
```

```
Pro Ala Pro Ile Glu Lys Thr Ile Ser Lys Ala Lys Gly Gln Pro Arg
                340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
        450                 455

<210> SEQ ID NO 111
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser
        115                 120                 125

<210> SEQ ID NO 112
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Gln Gln Lys Pro Gly Gln Ala Pro Arg Leu Leu Val
        35                  40                  45
```

-continued

```
Tyr Ser Ala Ser Thr Arg Ala Thr Gly Ile Pro Ala Arg Phe Ser Gly
 50                  55                  60

Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 113
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Ser Val Asp Ser Asn
                20                  25                  30

Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
 50                  55                  60

Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys
                100                 105

<210> SEQ ID NO 114
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Val Glu Ser Gly Gly Gly Val Val Gln Pro Gly Arg
 1               5                  10                  15
```

```
Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
```

```
                435                 440                 445
Leu Ser Leu Ser Pro Gly Lys
    450                 455

<210> SEQ ID NO 115
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Val Gln Leu Val Glu Ser Gly Gly Val Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
                85                  90                  95

Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser
        115                 120                 125

<210> SEQ ID NO 116
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
```

```
                145                 150                 155                 160
Ser Gln Glu Ser Val Thr Glu Gln Asp Ser Lys Asp Ser Thr Tyr Ser
                    165                 170                 175

Leu Ser Ser Thr Leu Thr Leu Ser Lys Ala Asp Tyr Glu Lys His Lys
                    180                 185                 190

Val Tyr Ala Cys Glu Val Thr His Gln Gly Leu Ser Ser Pro Val Thr
                    195                 200                 205

Lys Ser Phe Asn Arg Gly Glu Cys
                    210                 215

<210> SEQ ID NO 117
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
                20                  25                  30

Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
        50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys
                100                 105

<210> SEQ ID NO 118
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
                20                  25                  30

Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
        50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Trp Pro Pro
                85                  90                  95

Arg Leu Thr Phe Gly Gly Gly Ser Lys Val Glu Ile Lys Arg Thr Val
                100                 105                 110

Ala Ala Pro Ser Val Phe Ile Phe Pro Pro Ser Asp Glu Gln Leu Lys
```

```
                    115                 120                 125
Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 119
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Trp Pro Pro
                85                  90                  95

Arg Leu Thr Phe Gly Gly Gly Ser Lys Val Glu Ile Lys
            100                 105

<210> SEQ ID NO 120
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe His Asn Arg
            20                  25                  30

Ala Met His Trp Val Arg Gln Ala Pro Gly Lys Gly Leu Glu Trp Val
        35                  40                  45

Ala Leu Ile Tyr Phe Asp Gly Ser Lys Gln Tyr Tyr Ala Asp Ser Val
    50                  55                  60

Lys Gly Arg Phe Thr Ile Ser Arg Asp Asn Ser Lys Asn Thr Val Phe
65                  70                  75                  80

Leu Gln Met Asn Ser Leu Arg Pro Glu Asp Thr Ala Val Tyr Tyr Cys
```

```
                85                  90                  95
Ala Val Pro Gly Pro Ile Phe Gly Ile Phe Pro Pro Trp Ser Tyr Phe
            100                 105                 110

Asp His Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly
            340                 345

<210> SEQ ID NO 121
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Trp Pro Pro
                85                  90                  95
```

```
Arg Leu Thr Phe Gly Gly Gly Ser Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 122
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Trp Pro Pro
                85                  90                  95

Arg Leu Thr Phe Gly Gly Gly Ser Lys Val Glu Ile Lys
            100                 105

<210> SEQ ID NO 123
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60
```

```
Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 124
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Asp His Asn
             20                  25                  30

Leu Ala Trp Tyr Gln Gln Lys Pro Gly Gln Ala Pro Arg Leu Leu Val
         35                  40                  45

Tyr Ser Ala Ser Thr Arg Ala Thr Gly Ile Pro Ala Arg Phe Ser Gly
     50                  55                  60

Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys
            100                 105

<210> SEQ ID NO 125
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Ile Val Leu Thr Gln Ser Pro Ala Thr Leu Ser Val Ser Pro Gly
  1               5                  10                  15

Glu Arg Ala Thr Leu Ser Cys Arg Ala Ser Gln Ser Val Ser His Asn
             20                  25                  30
```

```
Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
 50                  55                  60

Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 126
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
 50                  55                  60

Ser Gly Ser Gly Thr Glu Phe Thr Leu Ala Ile Ser Ser Leu Gln Ser
 65                  70                  75                  80

Glu Asp Phe Ala Val Tyr Tyr Cys Gln His Tyr Thr Asn Trp Pro Pro
                 85                  90                  95

Arg Leu Thr Phe Gly Gly Gly Ser Lys Val Glu Ile Lys
            100                 105

<210> SEQ ID NO 127
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127
```

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Phe Pro Pro
                85                  90                  95

Arg Leu Thr Phe Gly Gly Gly Ser Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
210                 215

<210> SEQ ID NO 128
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser His Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Phe Pro Pro
                85                  90                  95

Arg Leu Thr Phe Gly Gly Gly Ser Lys Val Glu Ile Lys
            100                 105

<210> SEQ ID NO 129
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
                20                  25                  30

Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Phe Pro Pro
                85                  90                  95

Arg Leu Thr Phe Gly Gly Gly Ser Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215

<210> SEQ ID NO 130
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
                20                  25                  30

Leu Ala Trp Tyr Gln Gln Lys Pro Gly Gln Ala Pro Arg Leu Leu Val
            35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Phe Pro Pro
                85                  90                  95

Arg Leu Thr Phe Gly Gly Gly Ser Lys Val Glu Ile Lys
                100                 105

<210> SEQ ID NO 131
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80

Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 132
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Asp Ser Asn
            20                  25                  30

Leu Ala Trp Tyr Gln Gln Lys Pro Gly Gln Ala Pro Arg Leu Leu Val
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Ala Ile Ser Ser Leu Gln Ser
65                  70                  75                  80
```

```
Glu Asp Phe Ala Val Tyr Tyr Cys Gln His Tyr Thr Asn Tyr Pro Pro
                85                  90                  95

Arg Leu Thr Phe Gly Gly Gly Ser Lys Val Glu Ile Lys
            100                 105

<210> SEQ ID NO 133
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Glu Val Gln Leu Val Gln Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
```

```
                     325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
            355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Phe Phe Leu Tyr Ser
                405                 410                 415
Lys Leu Thr Val Asp Lys Ser Arg Trp Gln Gln Gly Asn Val Phe Ser
            420                 425                 430
Cys Ser Val Met His Glu Ala Leu His Asn His Tyr Thr Gln Lys Ser
            435                 440                 445
Leu Ser Leu Ser Pro Gly Lys
    450                 455

<210> SEQ ID NO 134
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Glu Val Gln Leu Val Gln Ser Gly Gly Gly Val Val Gln Pro Gly Lys
1               5                   10                  15
Ser Leu Arg Leu Ser Cys Ala Ala Ser Gly Leu Thr Phe Ser Ser Tyr
            20                  25                  30
Ala Val His Trp Val Arg Gln Ala Pro Gly Lys Gly Leu Glu Trp Val
        35                  40                  45
Thr Leu Ile Ser Tyr Asp Gly Ala Asn Gln Tyr Tyr Ala Asp Ser Val
    50                  55                  60
Lys Gly Arg Phe Thr Ile Ser Arg Asp Asn Ser Lys Asn Thr Val Tyr
65                  70                  75                  80
Leu Gln Met Asn Ser Leu Arg Pro Glu Asp Thr Ala Val Tyr Tyr Cys
                85                  90                  95
Ala Val Pro Gly Pro Val Phe Gly Ile Phe Pro Pro Trp Ser Tyr Phe
            100                 105                 110
Asp Asn Trp Gly Gln Gly Ile Leu Val Thr Val Ser Ser
        115                 120                 125

<210> SEQ ID NO 135
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Glu Thr Thr Leu Thr Gln Ser Pro Ala Thr Leu Ser Val Ser Pro Gly
1               5                   10                  15
Glu Arg Ala Thr Leu Ser Cys Arg Ala Ser Gln Val Ile Ser His Asn
            20                  25                  30
Leu Ala Trp Tyr Gln Gln Lys Pro Gly Gln Ala Pro Arg Leu Leu Ile
```

```
                35                  40                  45
Tyr Gly Ala Ser Thr Arg Ala Ser Gly Ile Pro Ala Arg Phe Ser Gly
 50                  55                  60

Ser Gly Ser Gly Thr Asp Tyr Thr Leu Thr Ile Thr Ser Leu Gln Ser
 65                  70                  75                  80

Glu Asp Phe Ala Val Tyr Tyr Cys Gln His Tyr Ser Asn Trp Pro Pro
                 85                  90                  95

Arg Leu Thr Phe Gly Gly Gly Thr Lys Val Glu Ile Lys Arg Thr Val
                100                 105                 110

Ala Ala Pro Ser Val Phe Ile Phe Pro Pro Ser Asp Glu Gln Leu Lys
                115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
            210                 215

<210> SEQ ID NO 136
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Glu Thr Thr Leu Thr Gln Ser Pro Ala Thr Leu Ser Val Ser Pro Gly
 1               5                  10                  15

Glu Arg Ala Thr Leu Ser Cys Arg Ala Ser Gln Val Ile Ser His Asn
                 20                  25                  30

Leu Ala Trp Tyr Gln Gln Lys Pro Gly Gln Ala Pro Arg Leu Leu Ile
             35                  40                  45

Tyr Gly Ala Ser Thr Arg Ala Ser Gly Ile Pro Ala Arg Phe Ser Gly
 50                  55                  60

Ser Gly Ser Gly Thr Asp Tyr Thr Leu Thr Ile Thr Ser Leu Gln Ser
 65                  70                  75                  80

Glu Asp Phe Ala Val Tyr Tyr Cys Gln His Tyr Ser Asn Trp Pro Pro
                 85                  90                  95

Arg Leu Thr Phe Gly Gly Gly Thr Lys Val Glu Ile Lys
                100                 105

<210> SEQ ID NO 137
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Glu Ser Gly Gly Gly Val Val Gln Pro Gly Lys
```

```
1               5                   10                  15
Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
            35                  40                  45

Thr Leu Ile Ser Tyr Asp Gly Ala Asn Gln Tyr Tyr Ala Asp Ser Val
50                      55                  60

Lys Gly Arg Phe Thr Ile Ser Arg Asp Asn Ser Lys Asn Thr Val Tyr
65                      70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430
```

```
Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 138
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Gln Val Gln Leu Val Glu Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser
        115                 120                 125

<210> SEQ ID NO 139
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140
```

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
            165                 170                 175

Leu Ser Ser Thr Leu Thr Leu Ser Lys Ala Asp Tyr Glu Lys His Lys
        180                 185                 190

Val Tyr Ala Cys Glu Val Thr His Gln Gly Leu Ser Ser Pro Val Thr
    195                 200                 205

Lys Ser Phe Asn Arg Gly Glu Cys
    210                 215

<210> SEQ ID NO 140
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys
            100                 105

<210> SEQ ID NO 141
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Glu Ser Gly Gly Gly Val Val Gln Pro Gly Lys
1               5                   10                  15

Ser Pro Arg Leu Ser Cys Ala Ala Ser Gly Pro Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
        370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 142
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Gln Val Gln Leu Val Glu Ser Gly Gly Gly Val Val Gln Pro Gly Lys

```
                1               5                   10                  15
            Ser Pro Arg Leu Ser Cys Ala Ala Ser Gly Pro Thr Phe Ser Ser Tyr
                            20                  25                  30

Ala Val His Trp Val Arg Gln Ala Pro Gly Lys Gly Leu Glu Trp Val
                            35                  40                  45

Thr Leu Ile Ser Tyr Asp Gly Ala Asn Gln Tyr Tyr Ala Asp Ser Val
                            50                  55                  60

Lys Gly Arg Phe Thr Ile Ser Arg Asp Asn Ser Lys Asn Thr Val Tyr
             65                 70                  75                  80

Leu Gln Met Asn Ser Leu Arg Pro Glu Asp Thr Ala Val Tyr Tyr Cys
                            85                  90                  95

Ala Val Pro Gly Pro Val Phe Gly Ile Phe Pro Pro Trp Ser Tyr Phe
                            100                 105                 110

Asp Asn Trp Gly Gln Gly Ile Leu Val Thr Val Ser Ser
                            115                 120                 125

<210> SEQ ID NO 143
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Glu Ile Val Leu Thr Gln Ser Pro Ala Thr Leu Ser Val Ser Pro Gly
 1               5                   10                  15

Glu Arg Ala Thr Leu Ser Cys Arg Ala Ser Gln Val Ile Ser His Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Ser Gly Ile Pro Ala Arg Phe Ser Gly
                50                  55                  60

Ser Gly Ser Gly Thr Asp Tyr Thr Leu Thr Ile Thr Ser Leu Gln Pro
 65                 70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys Arg Thr Val
                100                 105                 110

Ala Ala Pro Ser Val Ser Ile Phe Pro Pro Ser Asp Glu Gln Leu Lys
                115                 120                 125

Ser Gly Thr Ala Ser Val Val Cys Leu Leu Asn Asn Phe Tyr Pro Arg
                130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
                210                 215

<210> SEQ ID NO 144
<211> LENGTH: 109
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
50                  55                  60

Ser Gly Ser Gly Thr Asp Tyr Thr Leu Thr Ile Thr Ser Leu Gln Pro
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys
            100                 105

<210> SEQ ID NO 145
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

<210> SEQ ID NO 146
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Trp Pro Pro
                85                  90                  95

Arg Leu Thr Phe Gly Gly Gly Thr Lys Val Glu Ile Lys
            100                 105
```

<210> SEQ ID NO 147
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Glu Val Gln Leu Val Glu Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

Thr Phe Pro Ala Val Leu Gln Ser Ser Gly Leu Tyr Ser Leu Ser Ser
            180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
            450                 455

<210> SEQ ID NO 148
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Glu Val Gln Leu Val Glu Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
    50                  55                  60

Lys Gly Arg Phe Thr Ile Ser Arg Asp Asn Ser Lys Asn Thr Val Tyr
65                  70                  75                  80

```
Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser
        115                 120                 125

<210> SEQ ID NO 149
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
    50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Phe Pro Pro
                85                  90                  95

Arg Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 150
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30
```

-continued

Leu Ala Trp Tyr Gln Gln Lys Pro Gly Gln Ala Pro Arg Leu Leu Ile
            35                  40                  45

Tyr Gly Ala Ser Thr Arg Ala Ser Gly Ile Pro Ala Arg Phe Ser Gly
 50                  55                  60

Ser Gly Ser Gly Thr Asp Tyr Thr Leu Thr Ile Thr Ser Leu Gln Ser
 65                  70                  75                  80

Glu Asp Phe Ala Val Tyr Tyr Cys Gln His Tyr Ser Asn Phe Pro Pro
                 85                  90                  95

Arg Leu Thr Phe Gly Gly Gly Thr Lys Val Glu Ile Lys
            100                 105

<210> SEQ ID NO 151
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Glu Ile Val Leu Thr Gln Ser Pro Ala Thr Leu Ser Val Ser Pro Gly
 1               5                  10                  15

Glu Arg Ala Thr Leu Ser Cys Arg Ala Ser Gln Val Ile Ser His Asn
             20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Ser Gly Ile Pro Ala Arg Phe Ser Gly
 50                  55                  60

Ser Gly Ser Gly Thr Asp Tyr Thr Leu Thr Ile Thr Ser Leu Gln Ser
 65                  70                  75                  80

Glu Asp Phe Ala Val Tyr Tyr Cys Gln His Tyr Ser Asn Tyr Pro Pro
                 85                  90                  95

Arg Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 152
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

```
Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ser Gly Ile Pro Ala Arg Phe Ser Gly
50                  55                  60

Ser Gly Ser Gly Thr Asp Tyr Thr Leu Thr Ile Thr Ser Leu Gln Ser
65                  70                  75                  80

Glu Asp Phe Ala Val Tyr Tyr Cys Gln His Tyr Ser Asn Tyr Pro Pro
                85                  90                  95

Arg Leu Thr Phe Gly Gly Gly Thr Lys Val Glu Ile Lys
            100                 105
```

<210> SEQ ID NO 153
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

```
Glu Val Gln Leu Val Gln Ser Gly Ala Glu Val Lys Lys Pro Gly Ser
1               5                   10                  15

Ser Met Lys Val Ser Cys Lys Ala Ser Gly Ser Ile Phe Ser Asn Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Ala Ala Asn Tyr Ala Gln Lys Phe
50                  55                  60

Gln Gly Arg Val Thr Ile Thr Ala Asp Glu Ser Thr Ser Thr Val Tyr
65                  70                  75                  80

Met Glu Val Arg Ser Leu Arg Ser Glu Asp Thr Ala Val Tyr Tyr Cys
                85                  90                  95

Ala Arg Arg Gln Gln Leu Tyr Lys Gly Tyr Tyr His His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

-continued

```
                245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 154
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Glu Val Gln Leu Val Gln Ser Gly Ala Glu Val Lys Lys Pro Gly Ser
1               5                   10                  15

Ser Met Lys Val Ser Cys Lys Ala Ser Gly Ser Ile Phe Ser Asn Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Val Arg Ser Leu Arg Ser Glu Asp Thr Ala Val Tyr Tyr Cys
                85                  90                  95

Ala Arg Arg Gln Gln Leu Tyr Lys Gly Tyr Tyr His His Trp Gly Gln
            100                 105                 110

Gly Thr Leu Val Thr Val Ser Ser
        115                 120

<210> SEQ ID NO 155
<211> LENGTH: 216
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Ala Asn Asn
            20                  25                  30

Leu Ala Trp Tyr Gln Gln Lys Pro Gly Gln Ser Pro Arg Leu Leu Ile
        35                  40                  45

Tyr Gly Ala Ser Thr Arg Asp Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Met Tyr Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 156
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Ser Val Ala Asn Asn
            20                  25                  30

Leu Ala Trp Tyr Gln Gln Lys Pro Gly Gln Ser Pro Arg Leu Leu Ile
        35                  40                  45

Tyr Gly Ala Ser Thr Arg Asp Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95
```

Met Tyr Thr Phe Gly Gln Gly Thr Lys Leu Glu Ile Lys
            100                 105

<210> SEQ ID NO 157
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Gln Val Gln Leu Val Gln Ser Gly Ala Gly Val Lys Lys Pro Gly Ser
1               5                   10                  15

Ser Met Lys Val Ser Cys Lys Ala Ser Gly Ser Ile Phe Ser Asn Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Ala Ala Asn Tyr Ala Gln Lys Phe
    50                  55                  60

Gln Gly Arg Val Thr Ile Thr Ala Asp Glu Ser Thr Ser Thr Val Tyr
65                  70                  75                  80

Met Glu Val Arg Ser Leu Arg Ser Glu Asp Thr Ala Val Tyr Tyr Cys
                85                  90                  95

Ala Arg Arg Gln Gln Leu Tyr Lys Gly Tyr Tyr His His Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

-continued

```
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450
```

<210> SEQ ID NO 158
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Gln Val Gln Leu Val Gln Ser Gly Ala Gly Val Lys Lys Pro Gly Ser
1               5                   10                  15
Ser Met Lys Val Ser Cys Lys Ala Ser Gly Ser Ile Phe Ser Asn Tyr
            20                  25                  30
Gly Ile Ser Trp Val Arg Gln Ala Pro Gly Gln Gly Leu Glu Trp Met
        35                  40                  45
Gly Gly Ile Ile Pro Ile Phe Gly Ala Ala Asn Tyr Ala Gln Lys Phe
    50                  55                  60
Gln Gly Arg Val Thr Ile Thr Ala Asp Glu Ser Thr Ser Thr Val Tyr
65                  70                  75                  80
Met Glu Val Arg Ser Leu Arg Ser Glu Asp Thr Ala Val Tyr Tyr Cys
                85                  90                  95
Ala Arg Arg Gln Gln Leu Tyr Lys Gly Tyr Tyr His His Trp Gly Gln
            100                 105                 110
Gly Thr Leu Val Thr Val Ser Ser
        115                 120
```

<210> SEQ ID NO 159
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

```
Gln Val Gln Leu Val Gln Ser Gly Ala Glu Leu Lys Arg Pro Gly Ala
1               5                   10                  15
Ser Val Lys Val Ser Cys Lys Thr Ser Gly Tyr Ser Phe Asn Asn Tyr
            20                  25                  30
Gly Ile Asn Trp Val Arg Gln Ala Pro Gly Gln Gly Leu Glu Trp Met
        35                  40                  45
Gly Trp Ile Ser Ala Tyr Thr Gly Asn Thr His Tyr Ala Lys Asn Phe
    50                  55                  60
```

-continued

Glu Gly Arg Val Thr Leu Thr Thr Asp Thr Ser Thr Ser Thr Ala Tyr
65                  70                  75                  80

Met Glu Val Arg Ser Leu Arg Ser Asp Asp Ser Ala Val Tyr Phe Cys
                85                  90                  95

Ala Arg Ala Met Ile Gln Gly Val Val Thr Leu Tyr Leu Arg Pro Gly
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
450                 455

<210> SEQ ID NO 160
<211> LENGTH: 125

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Gln Val Gln Leu Val Gln Ser Gly Ala Glu Leu Lys Arg Pro Gly Ala
1               5                   10                  15

Ser Val Lys Val Ser Cys Lys Thr Ser Gly Tyr Ser Phe Asn Asn Tyr
                20                  25                  30

Gly Ile Asn Trp Val Arg Gln Ala Pro Gly Gln Gly Leu Glu Trp Met
            35                  40                  45

Gly Trp Ile Ser Ala Tyr Thr Gly Asn Thr His Tyr Ala Lys Asn Phe
        50                  55                  60

Glu Gly Arg Val Thr Leu Thr Thr Asp Thr Ser Thr Ser Thr Ala Tyr
65                  70                  75                  80

Met Glu Val Arg Ser Leu Arg Ser Asp Asp Ser Ala Val Tyr Phe Cys
                85                  90                  95

Ala Arg Ala Met Ile Gln Gly Val Val Thr Leu Tyr Leu Arg Pro Gly
            100                 105                 110

Asp Tyr Trp Gly Gln Gly Thr Leu Val Thr Val Ser Ser
        115                 120                 125

<210> SEQ ID NO 161
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Asn Trp
                20                  25                  30

Leu Ala Trp Tyr Gln Gln Lys Pro Gly Lys Ala Pro Lys Leu Leu Ile
            35                  40                  45

Tyr Lys Val Ser Thr Leu Glu Ser Gly Val Pro Ser Arg Phe Ser Gly
        50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Arg Tyr Thr Ser Asn Ser Gln
                85                  90                  95

Gly Phe Thr Phe Gly Gln Gly Thr Lys Leu Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190
```

Val Tyr Ala Cys Glu Val Thr His Gln Gly Leu Ser Ser Pro Val Thr
            195                 200                 205

Lys Ser Phe Asn Arg Gly Glu Cys
    210                 215

<210> SEQ ID NO 162
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Asn Trp
            20                  25                  30

Leu Ala Trp Tyr Gln Gln Lys Pro Gly Lys Ala Pro Lys Leu Leu Ile
        35                  40                  45

Tyr Lys Val Ser Thr Leu Glu Ser Gly Val Pro Ser Arg Phe Ser Gly
50                  55                  60

Ser Gly Ser Gly Thr Glu Phe Thr Leu Thr Ile Asn Ser Leu Gln Pro
65                  70                  75                  80

Asp Asp Phe Ala Thr Tyr Tyr Cys Gln Arg Tyr Thr Ser Asn Ser Gln
                85                  90                  95

Gly Phe Thr Phe Gly Gln Gly Thr Lys Leu Glu Ile Lys
            100                 105

<210> SEQ ID NO 163
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Gln Val Gln Leu Val Gln Ser Gly Ala Glu Val Lys Gln Pro Gly Ala
1               5                   10                  15

Ser Val Lys Val Ser Cys Lys Ala Ser Gly Tyr Thr Phe Asn Ala Tyr
            20                  25                  30

Tyr Ile His Trp Val Arg Gln Ala Pro Gly Gln Gly Leu Glu Trp Met
        35                  40                  45

Gly Trp Ile Asn Pro Asn Phe Gly Gly Thr His Tyr Ala Arg Lys Phe
50                  55                  60

Gln Gly Arg Val Thr Met Thr Arg Asp Ala Ser Ile Asn Thr Ala Tyr
65                  70                  75                  80

Met Glu Leu Asp Arg Leu Ile Ser Asp Thr Ala Val Tyr Tyr Cys
                85                  90                  95

Val Arg Trp Arg Ala Ala Ala Val Ile Met Asp Gln Phe Tyr Lys Met
            100                 105                 110

Asp Val Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

-continued

Pro Val Thr Val Ser Trp Asn Ser Gly Ala Leu Thr Ser Gly Val His
                165                 170                 175
Thr Phe Pro Ala Val Leu Gln Ser Ser Gly Leu Tyr Ser Leu Ser Ser
            180                 185                 190
Val Val Thr Val Pro Ser Ser Ser Leu Gly Thr Lys Thr Tyr Thr Cys
        195                 200                 205
Asn Val Asp His Lys Pro Ser Asn Thr Lys Val Asp Lys Thr Arg Glu
    210                 215                 220
Ser Lys Tyr Gly Pro Pro Cys Pro Ser Cys Pro Ala Pro Glu Phe Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
Gln Glu Asp Pro Glu Val Gln Phe Asn Trp Tyr Val Asp Gly Val Glu
        275                 280                 285
Val His Asn Ala Lys Thr Lys Pro Arg Glu Glu Gln Phe Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Gly Leu Pro Ser Ser
                325                 330                 335
Ile Glu Lys Thr Ile Ser Lys Ala Lys Gly Gln Pro Arg Glu Pro Gln
            340                 345                 350
Val Tyr Thr Leu Pro Pro Ala Gln Glu Glu Met Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Arg Leu Thr
                405                 410                 415
Val Asp Lys Ser Arg Trp Gln Glu Gly Asn Val Phe Ser Cys Ser Val
            420                 425                 430
Met His Glu Ala Leu His Asn His Tyr Thr Gln Lys Ser Leu Ser Leu
        435                 440                 445
Ser Leu Gly Lys
    450

<210> SEQ ID NO 164
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Gln Val Gln Leu Val Gln Ser Gly Ala Glu Val Lys Gln Pro Gly Ala
1               5                   10                  15
Ser Val Lys Val Ser Cys Lys Ala Ser Gly Tyr Thr Phe Asn Ala Tyr
            20                  25                  30
Tyr Ile His Trp Val Arg Gln Ala Pro Gly Gln Gly Leu Glu Trp Met
        35                  40                  45
Gly Trp Ile Asn Pro Asn Phe Gly Gly Thr His Tyr Ala Arg Lys Phe
    50                  55                  60

```
Gln Gly Arg Val Thr Met Thr Arg Asp Ala Ser Ile Asn Thr Ala Tyr
 65                  70                  75                  80

Met Glu Leu Asp Arg Leu Ile Ser Asp Thr Ala Val Tyr Tyr Cys
                 85                  90                  95

Val Arg Trp Arg Ala Ala Ala Val Ile Met Asp Gln Phe Tyr Lys Met
            100                 105                 110

Asp Val Trp Gly Gln Gly Thr Leu Val Thr Val Ser Ser
            115                 120             125

<210> SEQ ID NO 165
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ser Ser Glu Leu Thr Gln Pro Pro Ser Ala Ser Gly Thr Pro Gly Gln
  1               5                  10                  15

Arg Val Thr Ile Ser Cys Ser Gly Ser Thr Ser Asn Ile Gly Tyr Asn
                 20                  25                  30

Pro Val Ser Trp Tyr Gln Gln Val Pro Gly Thr Ala Pro Lys Leu Leu
             35                  40                  45

Ile Tyr Ser Asn Thr Glu Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Thr Leu
                 85                  90                  95

Asn Gly Pro Val Phe Gly Gly Gly Thr Lys Val Thr Val Leu Gly Gln
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 166
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ser Ser Glu Leu Thr Gln Pro Pro Ser Ala Ser Gly Thr Pro Gly Gln
  1               5                  10                  15
```

```
Arg Val Thr Ile Ser Cys Ser Gly Ser Thr Ser Asn Ile Gly Tyr Asn
             20                  25                  30

Pro Val Ser Trp Tyr Gln Gln Val Pro Gly Thr Ala Pro Lys Leu Leu
         35                  40                  45

Ile Tyr Ser Asn Thr Glu Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Thr Leu
                 85                  90                  95

Asn Gly Pro Val Phe Gly Gly Gly Thr Lys Val Thr Val Leu
             100                 105                 110

<210> SEQ ID NO 167
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Leu Ile Gly Thr Gly
             20                  25                  30

Ser Tyr Tyr Trp Gly Trp Ile Arg Gln Thr Pro Gly Lys Gly Met Glu
         35                  40                  45

Trp Ile Gly Ser Ile Ser Tyr Ser Gly Ser Thr Tyr Tyr His Pro Ser
 50                  55                  60

Leu Lys Ser Arg Val Thr Ile Ser Asp Asp Thr Ser Lys Asn Gln Leu
 65                  70                  75                  80

Phe Leu Lys Leu Arg Ser Val Thr Ala Ala Asp Thr Ala Gln Tyr Tyr
                 85                  90                  95

Cys Ala Arg Tyr Asn Trp Gly Ile Arg Tyr Phe Asp Phe Trp Gly Arg
             100                 105                 110

Gly Thr Leu Val Thr Val Ser Ser Ala Ser Thr Lys Gly Pro Ser Val
         115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175

Leu Gln Ser Ser Gly Leu Tyr Ser Leu Ser Ser Val Val Thr Val Pro
             180                 185                 190

Ser Ser Ser Leu Gly Thr Lys Thr Tyr Thr Cys Asn Val Asp His Lys
         195                 200                 205

Pro Ser Asn Thr Lys Val Asp Lys Thr Arg Glu Ser Lys Tyr Gly Pro
210                 215                 220

Pro Cys Pro Ser Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser Gln Glu Asp Pro Glu
```

```
                260                 265                 270
Val Gln Phe Asn Trp Tyr Val Asp Gly Val Glu Val His Asn Ala Lys
                275                 280                 285

Thr Lys Pro Arg Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ala Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
                435                 440                 445

<210> SEQ ID NO 168
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Leu Ile Gly Thr Gly
            20                  25                  30

Ser Tyr Tyr Trp Gly Trp Ile Arg Gln Thr Pro Gly Lys Gly Met Glu
        35                  40                  45

Trp Ile Gly Ser Ile Ser Tyr Ser Gly Ser Thr Tyr Tyr His Pro Ser
    50                  55                  60

Leu Lys Ser Arg Val Thr Ile Ser Asp Asp Thr Ser Lys Asn Gln Leu
65                  70                  75                  80

Phe Leu Lys Leu Arg Ser Val Thr Ala Ala Asp Thr Ala Gln Tyr Tyr
                85                  90                  95

Cys Ala Arg Tyr Asn Trp Gly Ile Arg Tyr Phe Asp Phe Trp Gly Arg
            100                 105                 110

Gly Thr Leu Val Thr Val Ser Ser
        115                 120

<210> SEQ ID NO 169
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 169

```
Asp Ile Gln Leu Thr Gln Ser Pro Leu Ser Pro Val Thr Leu Gly
1               5                   10                  15

Gln Pro Ala Ser Ile Ser Cys Arg Ser Ser Gln Ser Leu Leu Tyr Thr
            20                  25                  30

Asp Gly Phe Thr Tyr Leu Ser Trp Tyr His Gln Arg Pro Gly Gln Ser
            35                  40                  45

Pro Arg Arg Leu Ile Tyr Lys Ile Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Leu Thr Phe Gly Glu Gly Thr Lys Val Glu Ile Lys
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Lys Ser Tyr Ser Cys Gln Val Thr His Glu Gly Ser Thr Val Glu Lys
        195                 200                 205

Thr Val Ala Pro Thr Glu Cys Ser
        210                 215
```

<210> SEQ ID NO 170
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 170

```
Asp Ile Gln Leu Thr Gln Ser Pro Leu Ser Pro Val Thr Leu Gly
1               5                   10                  15

Gln Pro Ala Ser Ile Ser Cys Arg Ser Ser Gln Ser Leu Leu Tyr Thr
            20                  25                  30

Asp Gly Phe Thr Tyr Leu Ser Trp Tyr His Gln Arg Pro Gly Gln Ser
            35                  40                  45

Pro Arg Arg Leu Ile Tyr Lys Ile Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Leu Thr Phe Gly Glu Gly Thr Lys Val Glu Ile Lys
            100                 105                 110
```

<210> SEQ ID NO 171
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Val Ser His
1

<210> SEQ ID NO 172
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Val Asp Ser
1

<210> SEQ ID NO 173
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Val Ser Ser
1

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Val Asp His
1

<210> SEQ ID NO 175
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asn Phe Pro Pro
1

<210> SEQ ID NO 176
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asn Tyr Pro Pro
```

```
<210> SEQ ID NO 177
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asn Trp Pro Pro
1

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Phe Ala Phe His Asn Arg Ala Met His
1               5                   10

<210> SEQ ID NO 179
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Leu Ile Tyr Phe Asp Gly Ser Lys Gln Tyr Tyr Ala Asp Ser Val
1               5                   10                  15

Lys Gly

<210> SEQ ID NO 180
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ala Val Pro Gly Pro Ile Phe Gly Ile Phe Pro Pro Trp Ser Tyr Phe
1               5                   10                  15

Asp His Trp

<210> SEQ ID NO 181
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Val Pro Gly Pro Ile Phe Gly Ile Phe Pro Pro Trp Ser Tyr Phe
1               5                   10                  15

Asp His
```

```
<210> SEQ ID NO 182
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Arg Ala Ser Gln Ser Val Asp Ser Asn Leu Ala
1               5                   10

<210> SEQ ID NO 183
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ala Ser Gln Ser Val Ser His Asn Leu Ala
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Ala Ser Gln Ser Val Ser Ser Asn Leu Ala
1               5                   10

<210> SEQ ID NO 185
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Arg Ala Ser Gln Ser Val Asp His Asn Leu Ala
1               5                   10

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ser Gln Ser Val Asp Ser Asn Leu Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187
```

```
Ser Ala Ser Thr Arg Ala Thr
1               5

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln His Tyr Thr Asn Trp Pro Pro Arg Leu Thr
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gln His Tyr Thr Asn Tyr Pro Pro Arg Leu Thr
1               5                   10

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln His Tyr Thr Asn Phe Pro Pro Arg Leu Thr
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Leu Thr Phe Ser Ser Tyr Ala Val His
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Pro Thr Phe Ser Ser Tyr Ala Val His
1               5                   10

<210> SEQ ID NO 193
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 193

Thr Leu Ile Ser Tyr Asp Gly Ala Asn Gln Tyr Tyr Ala Asp Ser Val
1               5                   10                  15

Lys Gly

<210> SEQ ID NO 194
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ala Val Pro Gly Pro Val Phe Gly Ile Phe Pro Pro Trp Ser Tyr Phe
1               5                   10                  15

Asp Asn

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Ala Ser Gln Val Ile Ser His Asn Leu Ala
1               5                   10

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gly Ala Ser Thr Arg Ala Ser
1               5

<210> SEQ ID NO 197
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Gln His Tyr Ser Asn Trp Pro Pro Arg Leu Thr
1               5                   10

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198
```

Gln His Tyr Ser Asn Phe Pro Pro Arg Leu Thr
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gln His Tyr Ser Asn Tyr Pro Pro Arg Leu Thr
1               5                   10

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Gly Ser Ile Phe Ser Asn Tyr Gly Ile Ser
1               5                   10

<210> SEQ ID NO 201
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Gly Gly Ile Ile Pro Ile Phe Gly Ala Ala Asn Tyr Ala Gln Lys Phe
1               5                   10                  15

Gln Gly

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ala Arg Arg Gln Gln Leu Tyr Lys Gly Tyr Tyr His His
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Ala Ser Gln Ser Val Ala Asn Asn Leu Ala
1               5                   10

<210> SEQ ID NO 204
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Gly Ala Ser Thr Arg Asp Thr
1               5

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gln Gln Tyr Asn Asn Trp Pro Pro Met Tyr Thr
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Tyr Ser Phe Asn Asn Tyr Gly Ile Asn
1               5                   10

<210> SEQ ID NO 207
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Gly Trp Ile Ser Ala Tyr Thr Gly Asn Thr His Tyr Ala Lys Asn Phe
1               5                   10                  15

Glu Gly

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ala Arg Ala Met Ile Gln Gly Val Val Thr Leu Tyr Leu Arg Pro Gly
1               5                   10                  15

Asp Tyr Trp

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 209

Arg Ala Ser Gln Ser Ile Gly Asn Trp Leu Ala
1               5                   10

<210> SEQ ID NO 210
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Lys Val Ser Thr Leu Glu Ser
1               5

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gln Arg Tyr Thr Ser Asn Ser Gln Gly Phe Thr
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Gly Tyr Thr Phe Asn Ala Tyr Tyr Ile His
1               5                   10

<210> SEQ ID NO 213
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Trp Ile Asn Pro Asn Phe Gly Gly Thr His Tyr Ala Arg Lys Phe
1               5                   10                  15

Gln Gly

<210> SEQ ID NO 214
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val Arg Trp Arg Ala Ala Ala Val Ile Met Asp Gln Phe Tyr Lys Met
1               5                   10                  15

Asp Val

```
<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Gly Ser Thr Ser Asn Ile Gly Tyr Asn Pro Val Ser
1               5                   10

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Asn Thr Glu Arg Pro Ser
1               5

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ala Ala Trp Asp Asp Thr Leu Asn Gly Pro Val
1               5                   10

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Gly Leu Ile Gly Thr Gly Ser Tyr Tyr Trp Gly
1               5                   10

<210> SEQ ID NO 219
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Ser Ile Ser Tyr Ser Gly Ser Thr Tyr Tyr His Pro Ser Leu Lys
1               5                   10                  15

Ser

<210> SEQ ID NO 220
<211> LENGTH: 12
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 220

Ala Arg Tyr Asn Trp Gly Ile Arg Tyr Phe Asp Phe
1               5                   10

<210> SEQ ID NO 221
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Arg Ser Ser Gln Ser Leu Leu Tyr Thr Asp Gly Phe Thr Tyr Leu Ser
1               5                   10                  15

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Lys Ile Ser Asn Arg Asp Ser
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Met Gln Ala Thr His Trp Pro Leu Thr
1               5

<210> SEQ ID NO 224
<211> LENGTH: 566
<212> TYPE: PRT
<213> ORGANISM: Influenza A virus
<220> FEATURE:
<221> NAME/KEY: MOD_RES
<222> LOCATION: (239)..(240)
<223> OTHER INFORMATION: Any amino acid

<400> SEQUENCE: 224

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
        50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95
```

```
Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
            130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
            210                 215                 220

Lys Lys Phe Lys Pro Glu Ile Ala Ile Arg Pro Lys Val Arg Xaa Xaa
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
            370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
            450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510
```

-continued

```
Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 225
<211> LENGTH: 562
<212> TYPE: PRT
<213> ORGANISM: Influenza A virus

<400> SEQUENCE: 225

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Met Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Leu Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320
```

```
Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Thr Gly Thr
                485                 490                 495

Tyr Asp Tyr Pro Lys Tyr Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 226
<211> LENGTH: 566
<212> TYPE: PRT
<213> ORGANISM: Influenza A virus

<400> SEQUENCE: 226

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125
```

```
Ala Ser Ser Gly Thr Leu Glu Phe Asn Asn Glu Ser Phe Asn Trp Thr
        130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Arg Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540
```

-continued

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 227
<211> LENGTH: 568
<212> TYPE: PRT
<213> ORGANISM: Influenza A virus

<400> SEQUENCE: 227

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Lys Arg Gly Leu Phe Gly Ala Ile
            340                 345                 350

```
Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
        450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
            530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 228
<211> LENGTH: 562
<212> TYPE: PRT
<213> ORGANISM: Influenza A virus

<400> SEQUENCE: 228

Met Asn Thr Arg Ile Leu Ile Leu Thr Leu Thr Ala Val Ile His Thr
1               5                   10                  15

Asn Ala Asp Lys Ile Cys Leu Gly His His Ala Val Ser Asn Gly Thr
                20                  25                  30

Lys Val Asn Thr Leu Thr Glu Arg Gly Val Glu Val Val Asn Ala Thr
            35                  40                  45

Glu Thr Val Glu Gln Met Asn Ile Pro Arg Ile Cys Thr Lys Gly Lys
        50                  55                  60

Lys Ala Ile Asp Leu Gly Gln Cys Gly Leu Leu Gly Ile Val Thr Gly
65                  70                  75                  80

Pro Pro Gln Cys Asp Gln Phe Leu Glu Phe Thr Ala Asp Leu Ile Ile
                85                  90                  95

Glu Arg Arg Glu Gly Asn Asp Val Cys Tyr Pro Gly Lys Phe Val Asn
            100                 105                 110

Glu Glu Ala Leu Arg Gln Ile Leu Arg Gly Ser Gly Ile Asn Lys
        115                 120                 125

Glu Thr Thr Gly Phe Thr Tyr Ser Gly Ile Arg Thr Asn Gly Val Thr
        130                 135                 140

Ser Ala Cys Arg Arg Ser Glu Ser Ser Phe Tyr Ala Glu Met Lys Trp
```

```
            145                 150                 155                 160
Leu Leu Ser Asn Thr Asp Asn Ala Ala Phe Pro Gln Met Thr Lys Ser
                165                 170                 175

Tyr Lys Asn Thr Arg Asn Glu Pro Ala Leu Ile Val Trp Gly Ile His
                180                 185                 190

His Ser Gly Ser Thr Thr Glu Gln Thr Lys Leu Tyr Gly Ser Gly Ser
                195                 200                 205

Lys Leu Ile Thr Val Gly Ser Ser Asn Tyr Gln Gln Ser Phe Val Pro
    210                 215                 220

Ser Pro Gly Ala Arg Pro Gln Val Asn Gly Gln Ser Gly Arg Ile Asp
225                 230                 235                 240

Phe His Trp Leu Ile Leu Asn Pro Asn Asp Thr Val Thr Phe Ser Phe
                245                 250                 255

Asn Gly Ala Phe Val Ala Pro Asp Arg Val Ser Phe Phe Lys Gly Glu
                260                 265                 270

Ser Thr Gly Ile Gln Ser Glu Val Pro Val Asp Ala Asn Cys Glu Gly
                275                 280                 285

Glu Cys Tyr His Ser Gly Gly Thr Ile Thr Ser Asn Leu Pro Phe Gln
                290                 295                 300

Asn Val Asn Ser Arg Ala Val Gly Lys Cys Pro Lys Tyr Val Lys Gln
305                 310                 315                 320

Lys Ser Leu Leu Leu Ala Thr Gly Met Lys Asn Val Pro Glu Ile Pro
                325                 330                 335

Arg Lys Arg Lys Arg Gly Leu Phe Gly Ala Ile Ala Gly Phe Ile Glu
                340                 345                 350

Asn Gly Trp Glu Gly Leu Val Asp Gly Trp Tyr Gly Phe Arg His Gln
                355                 360                 365

Asn Ser Gln Gly Glu Gly Thr Ala Ala Asp Tyr Lys Ser Thr Gln Ser
                370                 375                 380

Ala Ile Asp Gln Ile Thr Gly Lys Leu Asn Arg Leu Ile Glu Lys Thr
385                 390                 395                 400

Asn Gln Gln Phe Glu Leu Ile Asp Asn Glu Phe Asn Glu Val Glu Lys
                405                 410                 415

Gln Ile Gly Asn Val Ile Asn Trp Thr Arg Asp Ser Ile Thr Glu Val
                420                 425                 430

Trp Ser Tyr Asn Ala Glu Leu Leu Val Ala Met Glu Asn Gln His Thr
                435                 440                 445

Ile Asp Leu Ala Asp Ser Glu Met Asn Lys Leu Tyr Glu Arg Val Arg
                450                 455                 460

Arg Gln Leu Arg Glu Asn Ala Glu Glu Asp Gly Thr Gly Cys Phe Glu
465                 470                 475                 480

Ile Phe His Lys Cys Asp Asp Cys Met Ala Ser Ile Arg Asn Asn
                485                 490                 495

Thr Tyr Asp His Ser Thr Tyr Arg Glu Glu Ala Met Gln Asn Arg Leu
                500                 505                 510

Lys Ile Asp Pro Val Lys Leu Ser Ser Gly Tyr Lys Asp Val Ile Leu
                515                 520                 525

Trp Phe Ser Phe Gly Ala Ser Cys Phe Leu Leu Leu Ala Ile Ala Met
                530                 535                 540

Gly Leu Gly Phe Ile Cys Val Lys Asn Gly Asn Met Arg Cys Thr Ile
545                 550                 555                 560

Cys Ile
```

<210> SEQ ID NO 229
<211> LENGTH: 566
<212> TYPE: PRT
<213> ORGANISM: Influenza A virus

<400> SEQUENCE: 229

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
        275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
        355                 360                 365

His His Gln Asn Glu Gln Gly Ser Gly Tyr Ala Ala Asp Leu Lys Ser
370                 375                 380

-continued

```
Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
            405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 230
<211> LENGTH: 565
<212> TYPE: PRT
<213> ORGANISM: Influenza A virus

<400> SEQUENCE: 230

Met Lys Ala Lys Leu Leu Val Leu Leu Tyr Ala Phe Val Ala Thr Asp
1               5                   10                  15

Ala Asp Thr Ile Cys Ile Gly Tyr His Ala Asn Asn Ser Thr Asp Thr
            20                  25                  30

Val Asp Thr Ile Phe Glu Lys Asn Val Ala Val Thr His Ser Val Asn
            35                  40                  45

Leu Leu Glu Asp Arg His Asn Gly Lys Leu Cys Lys Leu Lys Gly Ile
50                  55                  60

Ala Pro Leu Gln Leu Gly Lys Cys Asn Ile Thr Gly Trp Leu Leu Gly
65                  70                  75                  80

Asn Pro Glu Cys Asp Ser Leu Leu Pro Ala Arg Ser Trp Ser Tyr Ile
                85                  90                  95

Val Glu Thr Pro Asn Ser Glu Asn Gly Ala Cys Tyr Pro Gly Asp Phe
            100                 105                 110

Ile Asp Tyr Glu Glu Leu Arg Glu Gln Leu Ser Ser Val Ser Ser Leu
            115                 120                 125

Glu Arg Phe Glu Ile Phe Pro Lys Glu Ser Ser Trp Pro Asn His Thr
130                 135                 140

Phe Asn Gly Val Thr Val Ser Cys Ser His Arg Gly Lys Ser Ser Phe
145                 150                 155                 160

Tyr Arg Asn Leu Leu Trp Leu Thr Lys Lys Gly Asp Ser Tyr Pro Lys
                165                 170                 175

Leu Thr Asn Ser Tyr Val Asn Asn Lys Gly Lys Glu Val Leu Val Leu
```

```
              180                 185                 190
Trp Gly Val His His Pro Ser Ser Ser Asp Glu Gln Gln Ser Leu Tyr
        195                 200                 205

Ser Asn Gly Asn Ala Tyr Val Ser Val Ala Ser Ser Asn Tyr Asn Arg
    210                 215                 220

Arg Phe Thr Pro Glu Ile Ala Ala Arg Pro Lys Val Lys Asp Gln His
225                 230                 235                 240

Gly Arg Met Asn Tyr Tyr Trp Thr Leu Leu Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Glu Ser Gly Ile Ile Thr Ser Asn Ala Ser Met
        275                 280                 285

His Glu Cys Asn Thr Lys Cys Gln Thr Pro Gln Gly Ser Ile Asn Ser
    290                 295                 300

Asn Leu Pro Phe Gln Asn Ile His Pro Val Thr Ile Gly Glu Cys Pro
305                 310                 315                 320

Lys Tyr Val Arg Ser Thr Lys Leu Arg Met Val Thr Gly Leu Arg Asn
                325                 330                 335

Ile Pro Ser Ile Gln Tyr Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Leu Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 231
<211> LENGTH: 566
<212> TYPE: PRT
<213> ORGANISM: Influenza A virus
```

<400> SEQUENCE: 231

```
Met Lys Thr Ile Ile Ala Leu Ser Tyr Ile Phe Cys Leu Ala Leu Gly
 1               5                  10                  15

Gln Asp Leu Pro Gly Asn Asp Asn Ser Thr Ala Thr Leu Cys Leu Gly
             20                  25                  30

His His Ala Val Pro Asn Gly Thr Leu Val Lys Thr Ile Thr Asp Asp
         35                  40                  45

Gln Ile Glu Val Thr Asn Ala Thr Glu Leu Val Gln Ser Ser Ser Thr
 50                  55                  60

Gly Lys Ile Cys Asn Asn Pro His Arg Ile Leu Asp Gly Ile Asp Cys
 65                  70                  75                  80

Thr Leu Ile Asp Ala Leu Leu Gly Asp Pro His Cys Asp Val Phe Gln
                 85                  90                  95

Asn Glu Thr Trp Asp Leu Phe Val Glu Arg Ser Lys Ala Phe Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Ile Thr Glu Gly Phe Thr Trp Thr
130                 135                 140

Gly Val Thr Gln Asn Gly Gly Ser Asn Ala Cys Lys Arg Gly Pro Gly
145                 150                 155                 160

Asn Gly Phe Phe Ser Arg Leu Asn Trp Leu Thr Lys Ser Gly Ser Thr
                165                 170                 175

Tyr Pro Val Leu Asn Val Thr Met Pro Asn Asn Asp Asn Phe Asp Lys
            180                 185                 190

Leu Tyr Ile Trp Gly Val His His Pro Ser Thr Asn Gln Glu Gln Thr
        195                 200                 205

Ser Leu Tyr Val Gln Glu Ser Gly Arg Val Thr Val Ser Thr Arg Arg
210                 215                 220

Ser Gln Gln Ser Ile Ile Pro Asn Ile Gly Ser Arg Pro Trp Val Arg
225                 230                 235                 240

Gly Gln Ser Ser Arg Ile Ser Ile Tyr Trp Thr Ile Val Lys Pro Gly
                245                 250                 255

Asp Val Leu Val Ile Asn Ser Asn Gly Asn Leu Ile Ala Pro Arg Gly
            260                 265                 270

Tyr Phe Lys Met Arg Thr Gly Lys Ser Ser Ile Met Ser Ser Asp Ala
        275                 280                 285

Pro Ile Asp Thr Cys Ile Ser Glu Cys Ile Thr Pro Asn Gly Ser Ile
290                 295                 300

Pro Asn Asp Lys Pro Phe Gln Asn Val Asn Lys Ile Thr Tyr Gly Ala
305                 310                 315                 320

Cys Pro Lys Tyr Val Lys Gln Asn Thr Leu Lys Leu Ala Thr Gly Met
                325                 330                 335

Arg Asn Val Pro Glu Lys Gln Thr Arg Gly Leu Phe Gly Ala Ile Ala
            340                 345                 350

Gly Phe Ile Glu Asn Gly Trp Glu Gly Met Ile Asp Gly Trp Tyr Gly
        355                 360                 365

Phe Arg His Gln Asn Ser Glu Gly Thr Gly Gln Ala Ala Asp Leu Lys
370                 375                 380

Ser Thr Gln Ala Ala Ile Asp Gln Ile Asn Gly Lys Leu Asn Arg Val
385                 390                 395                 400

Ile Glu Lys Thr Asn Glu Lys Phe His Gln Ile Glu Lys Glu Phe Ser
```

-continued

```
                    405                 410                 415
Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
465                 470                 475                 480

Gly Cys Phe Lys Ile Tyr His Lys Cys Asp Asn Ala Cys Ile Glu Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 232
<211> LENGTH: 562
<212> TYPE: PRT
<213> ORGANISM: Influenza A virus

<400> SEQUENCE: 232

Met Asn Thr Gln Ile Leu Val Phe Ala Leu Val Ala Ser Ile Pro Thr
1               5                   10                  15

Asn Ala Asp Lys Ile Cys Leu Gly His His Ala Val Ser Asn Gly Thr
            20                  25                  30

Lys Val Asn Thr Leu Thr Glu Arg Gly Val Glu Val Val Asn Ala Thr
        35                  40                  45

Glu Thr Val Glu Arg Thr Asn Val Pro Arg Ile Cys Ser Lys Gly Lys
    50                  55                  60

Arg Thr Val Asp Leu Gly Gln Cys Gly Leu Leu Gly Thr Ile Thr Gly
65                  70                  75                  80

Pro Pro Gln Cys Asp Gln Phe Leu Glu Phe Ser Ala Asp Leu Ile Ile
                85                  90                  95

Glu Arg Arg Glu Gly Ser Asp Val Cys Tyr Pro Gly Lys Phe Val Asn
            100                 105                 110

Glu Glu Ala Leu Arg Gln Ile Leu Arg Glu Ser Gly Gly Ile Asp Lys
        115                 120                 125

Glu Thr Met Gly Phe Thr Tyr Ser Gly Ile Arg Thr Asn Gly Thr Thr
    130                 135                 140

Ser Ala Cys Arg Arg Ser Gly Ser Ser Phe Tyr Ala Glu Met Lys Trp
145                 150                 155                 160

Leu Leu Ser Asn Thr Asp Asn Ala Ala Phe Pro Gln Met Thr Lys Ser
                165                 170                 175

Tyr Lys Asn Thr Arg Lys Asp Pro Ala Leu Ile Ile Trp Gly Ile His
            180                 185                 190

His Ser Gly Ser Thr Thr Glu Gln Thr Lys Leu Tyr Gly Ser Gly Asn
        195                 200                 205
```

```
Lys Leu Ile Thr Val Gly Ser Ser Asn Tyr Gln Gln Ser Phe Val Pro
    210                 215                 220
Ser Pro Gly Ala Arg Pro Gln Val Asn Gly Gln Ser Gly Arg Ile Asp
225                 230                 235                 240
Phe His Trp Leu Ile Leu Asn Pro Asn Asp Thr Val Thr Phe Ser Phe
                245                 250                 255
Asn Gly Ala Phe Ile Ala Pro Asp Arg Ala Ser Phe Leu Arg Gly Lys
            260                 265                 270
Ser Met Gly Ile Gln Ser Glu Val Gln Val Asp Ala Asn Cys Glu Gly
        275                 280                 285
Asp Cys Tyr His Ser Gly Gly Thr Ile Ile Ser Asn Leu Pro Phe Gln
    290                 295                 300
Asn Ile Asn Ser Arg Ala Val Gly Lys Cys Pro Arg Tyr Val Lys Gln
305                 310                 315                 320
Glu Ser Leu Leu Leu Ala Thr Gly Met Lys Asn Val Pro Glu Ile Pro
                325                 330                 335
Lys Arg Arg Arg Arg Gly Leu Phe Gly Ala Ile Ala Gly Phe Ile Glu
            340                 345                 350
Asn Gly Trp Glu Gly Leu Ile Asp Gly Trp Tyr Gly Phe Arg His Gln
        355                 360                 365
Asn Ala Gln Gly Glu Gly Thr Ala Ala Asp Tyr Lys Ser Thr Gln Ser
    370                 375                 380
Ala Ile Asp Gln Ile Thr Gly Lys Leu Asn Arg Leu Ile Glu Lys Thr
385                 390                 395                 400
Asn Gln Gln Phe Glu Leu Ile Asp Asn Glu Phe Thr Glu Val Glu Arg
                405                 410                 415
Gln Ile Gly Asn Val Ile Asn Trp Thr Arg Asp Ser Met Thr Glu Val
            420                 425                 430
Trp Ser Tyr Asn Ala Glu Leu Leu Val Ala Met Glu Asn Gln His Thr
        435                 440                 445
Ile Asp Leu Ala Asp Ser Glu Met Asn Lys Leu Tyr Glu Arg Val Lys
    450                 455                 460
Arg Gln Leu Arg Glu Asn Ala Glu Glu Asp Gly Thr Gly Cys Phe Glu
465                 470                 475                 480
Ile Phe His Lys Cys Asp Asp Cys Met Ala Ser Ile Arg Asn Asn
                485                 490                 495
Thr Tyr Asp His Ser Lys Tyr Arg Glu Glu Ala Ile Gln Asn Arg Ile
            500                 505                 510
Gln Ile Asp Pro Val Lys Leu Ser Ser Gly Tyr Lys Asp Val Ile Leu
        515                 520                 525
Trp Phe Ser Phe Gly Ala Ser Cys Phe Ile Leu Leu Ala Ile Ala Met
    530                 535                 540
Gly Leu Val Phe Ile Cys Val Lys Asn Gly Asn Met Arg Cys Thr Ile
545                 550                 555                 560
Cys Ile

<210> SEQ ID NO 233
<211> LENGTH: 566
<212> TYPE: PRT
<213> ORGANISM: Influenza A virus

<400> SEQUENCE: 233

Met Glu Ala Arg Leu Leu Val Leu Leu Cys Ala Phe Ala Ala Thr Asn
1               5                   10                  15
```

-continued

Ala Asp Thr Ile Cys Ile Gly Tyr His Ala Asn Asn Ser Thr Asp Thr
              20                  25                  30

Val Asp Thr Val Leu Glu Lys Asn Val Thr Val Thr His Ser Val Asn
          35                  40                  45

Leu Leu Glu Asp Ser His Asn Gly Lys Leu Cys Lys Leu Lys Gly Ile
      50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
              100                 105                 110

Ile Asp Tyr Glu Glu Leu Arg Glu Gln Leu Ser Ser Val Ser Ser Phe
          115                 120                 125

Glu Lys Phe Glu Ile Phe Pro Lys Thr Ser Ser Trp Pro Asn His Glu
      130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
              165                 170                 175

Lys Leu Ser Lys Ser Tyr Val Asn Asn Lys Gly Lys Glu Val Leu Val
          180                 185                 190

Leu Trp Gly Val His His Pro Pro Thr Gly Thr Asp Gln Gln Ser Leu
      195                 200                 205

Tyr Gln Asn Ala Asp Ala Tyr Val Ser Val Gly Ser Ser Lys Tyr Asn
210                 215                 220

Arg Arg Phe Thr Pro Glu Ile Ala Ala Arg Pro Lys Val Arg Asp Gln
225                 230                 235                 240

Ala Gly Arg Met Asn Tyr Tyr Trp Thr Leu Leu Glu Pro Gly Asp Thr
              245                 250                 255

Ile Thr Phe Glu Ala Thr Gly Asn Leu Ile Ala Pro Trp Tyr Ala Phe
          260                 265                 270

Ala Leu Asn Arg Gly Ser Gly Ser Gly Ile Ile Thr Ser Asp Ala Pro
      275                 280                 285

Val His Asp Cys Asn Thr Lys Cys Gln Thr Pro His Gly Ala Ile Asn
      290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Ala Thr Gly Leu Arg
              325                 330                 335

Asn Ile Pro Ser Ile Gln Ser Arg Gly Leu Phe Gly Ala Ile Ala Gly
          340                 345                 350

Phe Ile Glu Gly Gly Trp Thr Gly Met Ile Asp Gly Trp Tyr Gly Tyr
      355                 360                 365

His His Gln Asn Glu Gln Gly Ser Gly Tyr Ala Ala Asp Gln Lys Ser
      370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
              405                 410                 415

Leu Glu Arg Arg Ile Glu Asn Leu Asn Lys Lys Val Asp Asp Gly Phe
          420                 425                 430

Leu Asp Ile Trp Thr Tyr Asn Ala Glu Leu Leu Val Leu Leu Glu Asn

```
                    435                 440                 445
Glu Arg Thr Leu Asp Phe His Asp Ser Asn Val Arg Asn Leu Tyr Glu
        450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asp Asp Ala Cys Met Glu Ser Val
                485                 490                 495

Arg Asn Gly Thr Tyr Asp Tyr Pro Lys Tyr Ser Glu Ser Lys Leu
            500                 505                 510

Asn Arg Glu Glu Ile Asp Gly Val Lys Leu Glu Ser Met Gly Val Tyr
                515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 234
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Val Glu Ser Gly Gly Gly Val Val Gln Pro Gly Lys
1               5                   10                  15

Ser Leu Arg Leu Ser Cys Ala Ala Ser Gly Leu Thr Phe Ser Ser Tyr
            20                  25                  30

Ala Val His Trp Val Arg Gln Ala Pro Gly Lys Gly Leu Glu Trp Val
        35                  40                  45

Thr Leu Ile Ser Tyr Asp Gly Ala Asn Gln Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Val Pro Gly Pro Val Phe Gly Ile Phe Pro Pro Trp Ser Tyr Phe
            100                 105                 110

Asp Asn Trp Gly Gln Gly Ile Leu Val Thr Val Ser Ser
        115                 120                 125

<210> SEQ ID NO 235
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Val Ile Ser His Asn
            20                  25                  30

Leu Ala Trp Tyr Gln Gln Lys Pro Gly Gln Ala Pro Arg Leu Leu Ile
```

35                  40                  45

Tyr Gly Ala Ser Thr Arg Ala Ser Gly Ile Pro Ala Arg Phe Ser Gly
 50                  55                  60

Ser Gly Ser Gly Thr Asp Tyr Thr Leu Thr Ile Thr Ser Leu Gln Ser
 65                  70                  75                  80

Glu Asp Phe Ala Val Tyr Tyr Cys Gln His Tyr Ser Asn Trp Pro Pro
                 85                  90                  95

Arg Leu Thr Phe Gly Gly Gly Thr Lys Val Glu Ile Lys
                100                 105

<210> SEQ ID NO 236
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Leu
                 85                  90                  95

Thr Phe Gly Gly Gly Thr Lys Val Glu Ile Lys
                100                 105

<210> SEQ ID NO 237
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
                35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Gln His Trp Gly Gln Gly Thr Leu Val Thr Val Ser Ser
                100                 105                 110

```
<210> SEQ ID NO 238
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Phe Gln His Trp Gly Gln Gly Thr Leu Val Thr Val Ser Ser
            100                 105                 110

<210> SEQ ID NO 239
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 240
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Phe Gln His Trp Gly Gln Gly Thr Leu Val Thr Val Ser Ser
            100                 105                 110

<210> SEQ ID NO 241
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Tyr Val Phe Gly Thr Gly Thr Lys Val Thr Val Leu
            100                 105                 110

<210> SEQ ID NO 242
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Met Asp Val Trp Gly Gln Gly Thr Thr Val Thr Val Ser Ser
            100                 105                 110

<210> SEQ ID NO 243
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Leu Thr Phe Gly Gly Gly Thr Lys Val Glu Ile Lys
            100                 105                 110

<210> SEQ ID NO 244
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Phe Asp Leu Trp Gly Arg Gly Thr Leu Val Thr Val Ser
            100                 105                 110

Ser

<210> SEQ ID NO 245
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Val Glu Ser Gly Gly Gly Val Val Gln Pro Gly Arg

-continued

```
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Phe Asp Tyr Trp Gly Gln Gly Thr Leu Val Thr Val Ser Ser
            100                 105                 110
```